US012656151B2

(12) United States Patent (10) Patent No.: US 12,656,151 B2
Seward et al. (45) Date of Patent: Jun. 16, 2026

(54) LIQUID DETECTION SENSOR

(71) Applicant: INSULET CORPORATION, Acton, MA (US)

(72) Inventors: David Seward, Seattle, WA (US); Ehsan Hajisaeid, Windham, NH (US); Kyle Breingan, Lowell, MA (US); Ayden Henson, Arlington, MA (US)

(73) Assignee: INSULET CORPORATION, Acton, MA (US)

( * ) Notice: Subject to any disclaimer, the term of this patent is extended or adjusted under 35 U.S.C. 154(b) by 0 days.

(21) Appl. No.: 18/625,827

(22) Filed: Apr. 3, 2024

(65) Prior Publication Data

US 2024/0337508 A1 Oct. 10, 2024

Related U.S. Application Data

(60) Provisional application No. 63/612,734, filed on Dec. 20, 2023, provisional application No. 63/494,407, filed on Apr. 5, 2023.

(51) Int. Cl.
 *G01D 5/165* (2006.01)
 *A61M 5/315* (2006.01)
 *G16H 20/13* (2018.01)

(52) U.S. Cl.
 CPC ......... *G01D 5/165* (2013.01); *A61M 5/31568* (2013.01); *G16H 20/13* (2018.01)

(58) Field of Classification Search
 CPC . G01D 5/165; A61M 5/31568; A61M 5/1684; A61M 5/1452; A61M 2205/3306;
 (Continued)

(56) References Cited

U.S. PATENT DOCUMENTS 441,663 A 12/1890 Hofbauer
955,911 A 4/1910 Saegmuller
 (Continued)

FOREIGN PATENT DOCUMENTS

CA 2863379 A1 8/2013
CN 201134101 Y 10/2008
 (Continued)

OTHER PUBLICATIONS

Yetisen AK, Martinez-Hurtado JL, Ünal B, Khademhosseini A, Butt H. Wearables in Medicine. Adv Mater. Jun. 11, 2018;30(33):e1706910. doi: 10.1002/adma.201706910. Epub ahead of print. PMID: 29893068; PMCID: PMC6541866. (Year: 2018).*
 (Continued)

*Primary Examiner* — Sun M Li
(74) *Attorney, Agent, or Firm* — GOODWIN PROCTER LLP

(57) ABSTRACT

In an aspect, a system for determining a liquid level in a drug delivery device is presented. The system includes a first spring and a second spring positioned adjacent the first spring. The system includes a rod configured to compress at least the first spring and contact the second spring. The system includes a sensing element in communication with the first spring and the second spring. The sensing element is configured to detect a difference in voltage of at least the first spring. A difference in voltage of at least the first spring corresponds to an amount of liquid drug of the drug delivery device.

20 Claims, 32 Drawing Sheets

(58) Field of Classification Search

CPC ...... A61M 2205/3317; A61M 5/14248; G16H 20/13

See application file for complete search history.

(56) References Cited

U.S. PATENT DOCUMENTS

| 2,911,008 | A | 11/1959 | Du Bois |
| 4,206,401 | A | 6/1980 | Meyer |
| 4,237,878 | A | 12/1980 | Kobayashi et al. |
| 4,277,226 | A | 7/1981 | Archibald |
| 4,307,713 | A | 12/1981 | Galkin et al. |
| 4,398,542 | A | 8/1983 | Cunningham et al. |
| 4,560,979 | A | 12/1985 | Rosskopf |
| 4,587,850 | A | 5/1986 | Moser |
| 4,801,957 | A | 1/1989 | Vandemoere |
| 4,836,752 | A | 6/1989 | Burkett |
| 4,850,954 | A | 7/1989 | Charvin |
| 4,882,600 | A | 11/1989 | Van de Moere |
| 4,961,055 | A | 10/1990 | Habib et al. |
| 4,973,998 | A | 11/1990 | Gates |
| 4,991,743 | A | 2/1991 | Walker |
| 5,045,871 | A | 9/1991 | Reinholdson |
| 5,135,485 | A | 8/1992 | Cohen et al. |
| 5,239,326 | A | 8/1993 | Takai |
| 5,368,570 | A | 11/1994 | Thompson et al. |
| 5,452,033 | A | 9/1995 | Balling et al. |
| 5,563,584 | A | 10/1996 | Rader et al. |
| 5,575,770 | A | 11/1996 | Melsky et al. |
| 5,576,781 | A | 11/1996 | Deleeuw |
| 5,585,733 | A | 12/1996 | Paglione |
| 5,586,553 | A | 12/1996 | Halili et al. |
| 5,647,853 | A | 7/1997 | Feldmann et al. |
| 5,660,163 | A | 8/1997 | Schulman et al. |
| 5,726,404 | A | 3/1998 | Brody |
| 5,726,751 | A | 3/1998 | Altendorf et al. |
| 5,785,681 | A | 7/1998 | Indravudh et al. |
| 5,800,420 | A | 9/1998 | Gross et al. |
| 5,814,020 | A | 9/1998 | Gross |
| 5,830,999 | A | 11/1998 | Dunn |
| 5,867,688 | A | 2/1999 | Simmon et al. |
| 5,876,377 | A | 3/1999 | Kriesel |
| 5,899,882 | A | 5/1999 | Waksman et al. |
| 5,906,592 | A | 5/1999 | Kriesel et al. |
| 6,045,533 | A | 4/2000 | Kriesel et al. |
| 6,152,898 | A | 11/2000 | Olsen |
| 6,171,264 | B1 | 1/2001 | Bader |
| 6,206,850 | B1 | 3/2001 | ONeil |
| 6,210,368 | B1 | 4/2001 | Rogers |
| 6,381,029 | B1 | 4/2002 | Tipirneni |
| 6,666,852 | B2 | 12/2003 | Niedospial, Jr. |
| 6,685,452 | B2 | 2/2004 | Christiansen et al. |
| 6,740,059 | B2 | 5/2004 | Flaherty |
| 6,768,319 | B2 | 7/2004 | Wang |
| 6,830,558 | B2 | 12/2004 | Flaherty et al. |
| 7,018,360 | B2 | 3/2006 | Flaherty et al. |
| 7,128,727 | B2 | 10/2006 | Flaherty et al. |
| 7,137,964 | B2 | 11/2006 | Flaherty |
| 7,144,384 | B2 | 12/2006 | Gorman et al. |
| 7,182,726 | B2 | 2/2007 | Williams et al. |
| 7,220,245 | B2 | 5/2007 | Kriesel |
| 7,303,073 | B2 | 12/2007 | Raynal-Olive et al. |
| 7,303,549 | B2 | 12/2007 | Flaherty |
| 8,056,719 | B2 | 11/2011 | Porret et al. |
| 8,105,282 | B2 | 1/2012 | Susi et al. |
| 8,285,487 | B2 | 10/2012 | Bergstrom et al. |
| 8,454,557 | B1 | 6/2013 | Qi et al. |
| 8,461,561 | B2 | 6/2013 | Freeman et al. |
| 8,613,724 | B2 | 12/2013 | Lanier, Jr. et al. |
| 8,727,117 | B2 | 5/2014 | Maasarani |
| 8,734,396 | B2 | 5/2014 | Wyss |
| 8,758,308 | B2 | 6/2014 | Alferness et al. |
| 9,005,166 | B2 | 4/2015 | Uber, III et al. |
| 9,248,229 | B2 | 2/2016 | Devouassoux et al. |
| 9,427,710 | B2 | 8/2016 | Jansen |
| 9,598,195 | B2 | 3/2017 | Deutschle et al. |

| 9,862,519 | B2 | 1/2018 | Deutschle et al. |
| 10,046,114 | B1 | 8/2018 | Biederman et al. |
| 10,086,131 | B2 | 10/2018 | Okihara |
| 10,342,926 | B2 | 7/2019 | Nazzaro et al. |
| 10,441,717 | B2 | 10/2019 | Schmid et al. |
| 11,724,027 | B2 * | 8/2023 | Allis .................. A61M 5/1452 |
| | | | 604/500 |
| 2001/0034502 | A1 | 10/2001 | Moberg et al. |
| 2002/0032374 | A1 | 3/2002 | Holker et al. |
| 2002/0066715 | A1 | 6/2002 | Niedospial |
| 2002/0161307 | A1 | 10/2002 | Yu et al. |
| 2003/0073952 | A1 | 4/2003 | Flaherty et al. |
| 2003/0120262 | A1 | 6/2003 | Weiland et al. |
| 2003/0136189 | A1 | 7/2003 | Lauman et al. |
| 2003/0139774 | A1 | 7/2003 | Epstein et al. |
| 2003/0198558 | A1 | 10/2003 | Nason et al. |
| 2004/0010207 | A1 | 1/2004 | Flaherty et al. |
| 2004/0010507 | A1 | 1/2004 | Bellew |
| 2004/0085215 | A1 | 5/2004 | Moberg et al. |
| 2004/0115068 | A1 | 6/2004 | Hansen et al. |
| 2004/0215492 | A1 | 10/2004 | Choi |
| 2005/0055242 | A1 | 3/2005 | Bello et al. |
| 2005/0238507 | A1 * | 10/2005 | Dilanni .................... F04B 9/08 |
| | | | 417/415 |
| 2006/0086909 | A1 | 4/2006 | Schaber |
| 2006/0092569 | A1 | 5/2006 | Che et al. |
| 2006/0253088 | A1 | 11/2006 | Chow et al. |
| 2006/0264926 | A1 | 11/2006 | Kochamba |
| 2006/0282290 | A1 | 12/2006 | Flaherty et al. |
| 2007/0025811 | A1 | 2/2007 | Wilhelm |
| 2007/0027370 | A1 | 2/2007 | Brauker et al. |
| 2007/0078784 | A1 | 4/2007 | Donovan et al. |
| 2007/0112332 | A1 | 5/2007 | Harding et al. |
| 2007/0118405 | A1 | 5/2007 | Campbell et al. |
| 2007/0179885 | A1 | 8/2007 | Bird et al. |
| 2007/0191770 | A1 * | 8/2007 | Moberg ............ A61M 5/14244 |
| | | | 604/131 |
| 2007/0233051 | A1 | 10/2007 | Hohl et al. |
| 2007/0255260 | A1 | 11/2007 | Haase |
| 2008/0001737 | A1 | 1/2008 | Metry |
| 2008/0004515 | A1 | 1/2008 | Jennewine |
| 2008/0027371 | A1 | 1/2008 | Higuchi et al. |
| 2008/0033272 | A1 | 2/2008 | Gough et al. |
| 2008/0051765 | A1 | 2/2008 | Mounce |
| 2008/0065000 | A1 | 3/2008 | Bidinger et al. |
| 2008/0077081 | A1 | 3/2008 | Mounce et al. |
| 2008/0119790 | A1 | 5/2008 | Hawkins et al. |
| 2008/0173073 | A1 | 7/2008 | Downie et al. |
| 2008/0249508 | A1 | 10/2008 | Lopez et al. |
| 2008/0255438 | A1 | 10/2008 | Saidara et al. |
| 2008/0269723 | A1 | 10/2008 | Mastrototaro et al. |
| 2008/0281290 | A1 | 11/2008 | Yodfat et al. |
| 2009/0048556 | A1 | 2/2009 | Durand |
| 2009/0062767 | A1 | 3/2009 | Van Antwerp et al. |
| 2009/0069787 | A1 | 3/2009 | Estes et al. |
| 2009/0112769 | A1 | 4/2009 | Dicks et al. |
| 2009/0177142 | A1 | 7/2009 | Blomquist et al. |
| 2009/0254041 | A1 | 10/2009 | Krag et al. |
| 2010/0076275 | A1 | 3/2010 | Chu et al. |
| 2010/0094251 | A1 | 4/2010 | Estes |
| 2010/0114026 | A1 | 5/2010 | Karratt et al. |
| 2010/0137784 | A1 | 6/2010 | Cefai et al. |
| 2010/0145272 | A1 | 6/2010 | Cefai et al. |
| 2010/0185175 | A1 | 7/2010 | Kamen et al. |
| 2010/0286997 | A1 | 11/2010 | Srinivasan |
| 2011/0108158 | A1 | 5/2011 | Huwiler et al. |
| 2011/0124996 | A1 | 5/2011 | Reinke et al. |
| 2011/0130742 | A1 | 6/2011 | Hawkins et al. |
| 2011/0142688 | A1 | 6/2011 | Chappel et al. |
| 2011/0152658 | A1 | 6/2011 | Peyser et al. |
| 2011/0213306 | A1 | 9/2011 | Hanson et al. |
| 2011/0218495 | A1 | 9/2011 | Remebe |
| 2011/0225024 | A1 | 9/2011 | Seyer et al. |
| 2011/0231204 | A1 | 9/2011 | De La Huerga |
| 2011/0246235 | A1 | 10/2011 | Powell et al. |
| 2011/0313680 | A1 | 12/2011 | Doyle, III |
| 2011/0316562 | A1 | 12/2011 | Cefai et al. |
| 2011/0319814 | A1 | 12/2011 | Sullivan et al. |
| 2012/0029941 | A1 | 2/2012 | Malave et al. |

(56) References Cited

U.S. PATENT DOCUMENTS

| | | | |
|---|---|---|---|
| 2012/0050046 A1 | 3/2012 | Satorius et al. | |
| 2012/0054841 A1 | 3/2012 | Schultz et al. | |
| 2012/0056000 A1 | 3/2012 | Shores | |
| 2012/0153936 A1 | 6/2012 | Romani et al. | |
| 2012/0182939 A1 | 7/2012 | Rajan et al. | |
| 2012/0184909 A1 | 7/2012 | Gyrn | |
| 2012/0203085 A1 | 8/2012 | Tsukamoto | |
| 2012/0232520 A1 | 9/2012 | Sloan et al. | |
| 2012/0265166 A1 | 10/2012 | Yodfat | |
| 2012/0277667 A1 | 11/2012 | Yodat et al. | |
| 2013/0030841 A1 | 1/2013 | Bergstrom et al. | |
| 2013/0036100 A1 | 2/2013 | Nagpal et al. | |
| 2013/0060194 A1 | 3/2013 | Rostein | |
| 2013/0080832 A1 | 3/2013 | Dean et al. | |
| 2013/0138452 A1 | 5/2013 | Cork et al. | |
| 2013/0173473 A1 | 7/2013 | Birtwhistle et al. | |
| 2013/0245545 A1 | 9/2013 | Arnold et al. | |
| 2013/0274576 A1 | 10/2013 | Amirouche et al. | |
| 2014/0114277 A1 | 4/2014 | Eggert et al. | |
| 2014/0163664 A1 | 6/2014 | Goldsmith | |
| 2014/0180203 A1 | 6/2014 | Budiman et al. | |
| 2014/0324018 A1* | 10/2014 | Bazargan | A61M 5/1456 604/151 |
| 2015/0038898 A1 | 2/2015 | Palmer et al. | |
| 2015/0057913 A1 | 2/2015 | Benhammou | |
| 2015/0119666 A1 | 4/2015 | Brister et al. | |
| 2015/0157537 A1 | 6/2015 | Lanigan et al. | |
| 2015/0290391 A1 | 10/2015 | Schmid et al. | |
| 2016/0008536 A1 | 1/2016 | Gravesen et al. | |
| 2016/0022905 A1 | 1/2016 | Nagar et al. | |
| 2016/0144105 A1 | 5/2016 | Hooven et al. | |
| 2016/0184517 A1 | 6/2016 | Baek et al. | |
| 2016/0296695 A1 | 10/2016 | Hassman et al. | |
| 2016/0339172 A1 | 11/2016 | Michaud et al. | |
| 2017/0173261 A1 | 6/2017 | O'Connor et al. | |
| 2017/0290975 A1* | 10/2017 | Barmaimon | F03G 7/0646 |
| 2017/0340811 A1 | 11/2017 | Pananen | |
| 2018/0008767 A1 | 1/2018 | Lambert | |
| 2018/0040255 A1 | 2/2018 | Freeman et al. | |
| 2018/0280609 A1 | 10/2018 | Nishimura et al. | |
| 2018/0296757 A1 | 10/2018 | Finan et al. | |
| 2019/0001057 A1 | 1/2019 | Tsoukalis et al. | |
| 2019/0365990 A1* | 12/2019 | Phillips | A61M 5/14248 |
| 2020/0338264 A1* | 10/2020 | Allis | A61M 5/14248 |
| 2020/0353173 A1* | 11/2020 | Holmquist | A61M 5/20 |
| 2022/0390258 A1 | 12/2022 | Cardinali et al. | |
| 2023/0055226 A1* | 2/2023 | Kamrava | A61M 5/1452 |
| 2023/0120570 A1* | 4/2023 | Mccaffrey | A61M 5/145 604/131 |
| 2023/0211077 A1* | 7/2023 | Mccaffrey | G16H 20/17 604/132 |

FOREIGN PATENT DOCUMENTS

| | | | |
|---|---|---|---|
| CN | 107096091 A | 8/2017 | |
| EP | 0789146 A1 | 8/1997 | |
| EP | 1065378 A2 | 1/2001 | |
| EP | 1762263 A1 | 3/2007 | |
| EP | 1839694 A1 | 10/2007 | |
| EP | 1852703 A1 | 11/2007 | |
| EP | 2099384 A1 | 9/2009 | |
| EP | 2229970 A1 | 9/2010 | |
| EP | 2353628 A2 | 8/2011 | |
| EP | 2556815 A1 | 2/2013 | |
| EP | 1874390 B1 | 10/2014 | |
| EP | 3068290 A1 | 9/2016 | |
| EP | 3187201 A1 | 7/2017 | |
| EP | 3598942 A1 | 1/2020 | |
| EP | 3607985 A1 | 2/2020 | |
| ES | 2559866 T3 | 2/2016 | |
| GB | 1401588 A | 7/1975 | |
| GB | 2176595 A | 12/1986 | |
| GB | 2443260 A | 4/2008 | |
| GB | 2443261 A | 4/2008 | |
| GB | 2461086 A | 12/2009 | |
| GB | 2495014 A | 3/2013 | |
| GB | 2524717 A | 10/2015 | |
| GB | 2525149 A | 10/2015 | |
| JP | 2001190659 A | 7/2001 | |
| JP | 2003154190 A | 5/2003 | |
| JP | 2007144141 A1 | 6/2007 | |
| JP | 2007307359 A | 11/2007 | |
| JP | 2008536625 A | 9/2008 | |
| JP | 2008242502 A | 10/2008 | |
| JP | 2010510027 A | 4/2010 | |
| JP | 2012210441 A | 11/2012 | |
| KR | 101828049 B1 | 2/2018 | |
| KR | 20220032391 A | 3/2022 | |
| WO | 9801071 A1 | 1/1998 | |
| WO | 9819145 A1 | 5/1998 | |
| WO | 9824495 A1 | 6/1998 | |
| WO | 9841267 A1 | 9/1998 | |
| WO | 0010628 A2 | 3/2000 | |
| WO | 0013580 A1 | 3/2000 | |
| WO | 0019887 A1 | 4/2000 | |
| WO | 0061215 A1 | 10/2000 | |
| WO | 0078210 A1 | 12/2000 | |
| WO | 2005031631 A2 | 4/2005 | |
| WO | 2006060668 A2 | 6/2006 | |
| WO | 2007112034 A2 | 10/2007 | |
| WO | 2008024814 A2 | 2/2008 | |
| WO | 2009023634 A2 | 2/2009 | |
| WO | 2009032399 A1 | 3/2009 | |
| WO | 2009070731 A1 | 6/2009 | |
| WO | 2010025433 A1 | 3/2010 | |
| WO | 2010078434 A2 | 7/2010 | |
| WO | 2010146579 A1 | 12/2010 | |
| WO | 2011012465 A1 | 2/2011 | |
| WO | 2011133823 A1 | 10/2011 | |
| WO | 2012065780 A2 | 5/2012 | |
| WO | 2013149186 A1 | 10/2013 | |
| WO | 2014136105 A1 | 9/2014 | |
| WO | 2014154777 A1 | 10/2014 | |
| WO | 2014204894 A2 | 12/2014 | |
| WO | 2015061690 A1 | 4/2015 | |
| WO | 2015177652 A1 | 11/2015 | |
| WO | 2015187793 A1 | 12/2015 | |
| WO | 2016041873 A1 | 3/2016 | |
| WO | 2016162755 A2 | 10/2016 | |
| WO | 2016181384 A2 | 11/2016 | |
| WO | 2017089289 A1 | 6/2017 | |
| WO | 2017205816 A1 | 11/2017 | |
| WO | 2019043702 A1 | 3/2019 | |
| WO | 2019094440 A1 | 5/2019 | |
| WO | 2020124058 A1 | 6/2020 | |

OTHER PUBLICATIONS

S. Das and B. Chakraborty, "A Pencil Drawn Capacitive Sensor used for Liquid Drug Volume Measurement in Syringe Pump," 2020 IEEE Applied Signal Processing Conference (ASPCON), Kolkata, India, 2020, pp. 85-88, doi: 10.1109/ASPCON49795.2020.9276687. (Year: 2020).*

H. Ren, B. S. Yeow, J. Sun and J. V. Iyer, "Electromagnetic Needleless Injector With Halbach Array Towards Intravitreal Delivery," in IEEE Access, vol. 6, pp. 1267-1276, 2018, doi: 10.1109/ACCESS.2017.2778193. (Year: 2017).*

H. Wang, T. Wang and C. Lee, "Self-powered liquid volume sensor aiming at lab-on-chip applications," 2016 IEEE 11th Annual International Conference on Nano/Micro Engineered and Molecular Systems (NEMS), Sendai, Japan, 2016, pp. 34-37, doi: 10.1109/NEMS.2016.7758194. (Year: 2016).*

Y. Yao, J. Ma and H. Liu, "Application of Pressure Liquid Level Detection Technology in the Automatic Micropipette Module," 2018 2nd International Conference on Robotics and Automation Sciences (ICRAS), Wuhan, China, 2018, pp. 1-5, doi: 10.1109/ICRAS.2018.8442348. (Year: 2018).*

European Search Report for the European Patent Application No. EP03743667, dated Jul. 22, 2008.

(56) References Cited

OTHER PUBLICATIONS

International Search Report and Written Opinion mailed Sep. 9, 2016, issued in PCT Patent Application No. PCT/US2016/037189, 12 pages.

Preliminary Report on Patentability mailed Dec. 21, 2017, issued in PCT Patent Application No. PCT/US2016/037189.

U.K. Intellectual Property Office, GB Application No. GB 1401587. 9, "Search Report under Section 17(5)" Aug. 11, 2015, 1 page.

International Search Report and Written Opinion for PCT Application No. PCT/GB2015/050247, May 8, 2015, 14 pages.

Extended Search Report mailed Nov. 24, 2017, issued in European Patent Application No. 15779465.2, 10 pages.

International Search Report and Written Opinion for PCT Application No. PCT/US15/26875, mailed Jan. 18, 2016, 10 pages.

U.K. Intellectual Property Office, GB Application No. GB 1401588. 7, "Search Report under Section 17(5)" Aug. 17, 2015, 1 page.

U.K. Intellectual Property Office, GB Application No. GB 1401589. 5, "Search Report under Section 17" Jul. 27, 2015, 1 page.

International Search Report and Written Opinion for PCT Application No. PCT/GB2015/050250, May 7, 2015, 9 pages.

3GPP TS 23.003 V10.0.0.0 Numbering, addressing and identification. Dec. 2010.

International Search Report and Written Opinion for PCT Application No. PCT/GB2015/050251, Jun. 12, 2015, 9 pages.

European Search Report for the European Patent Application No. EP19194241, dated Oct. 22, 2019, 6 pages.

International Preliminary Report on Patentability for PCT/US2017/061095, issued on May 14, 2019, 6 pages.

International Search Report and Written Opinion for PCT/US18/52468, mailed on Feb. 26, 2019, 16 pages.

International Search Report and Written Opinion for PCT/US2017/061095, mailed on Feb. 20, 2018, 8 pages.

International Search Report and Written Opinion for the International Patent Application No. PCT/US2021/047690, mailed Jan. 14, 2022, 13 pages.

International Search Report and Written Opinion for the International Patent Application No. PCT/US2022/055745, mailed Feb. 14, 2022, 13 pages.

International Search Report and Written Opinion for the International Patent Application No. PCT/US2021/053162, mailed Mar. 28, 2022, 18 pages.

International Search Report and Written Opinion for the International Patent Application No. PCT/US2021/064041, mailed Apr. 29, 2022, 11 pages.

International Search Report and Written Opinion for the International Patent Application No. PCT/US2022/015809, mailed Jun. 20, 2022, 15 pages.

International Search Report and Written Opinion for International Patent Application No. PCT/US2022/029012, mailed Aug. 19, 2022, 12 pages.

European Search Report and Written Opinion, Application No. EP02768908, dated Apr. 30, 2010.

International Search Report and Written Opinion, Application No. PCT/US2019/042233, mailed Jan. 3, 2020, 14 pages.

International Search Report and Written Opinion, Application No. PCT/US2021/060148, mailed Mar. 17, 2022, 17 pages.

International Search Report and Written Opinion, Application No. PCT/US2022/016713, mailed Aug. 5, 2022, 19 pages.

European Search Report and Written Opinion for the EP Application No. EP17736272, dated Oct. 7, 2019.

International Search Report and Written Opinion dated Feb. 13, 2009 issued in related International Patent Application No. PCT/US08/84971, 6 pages.

Novolog, "NovoLog Flex Pen", available at http://www.novolog.com/devices-flexpen.asp; retrieved on Sep. 11, 2007.

International Search Report and Written Opinion dated Mar. 27, 2020 issued in International Patent Application No. PCT/US19/42408, 18 pages.

International Search Report and Written Opinion for Application No. PCT/US17/12207, mailed May 26, 2017, 10 pages.

International Search Report and Written Opinion for Application No. PCT/US2024/022820, mailed Jul. 11, 2024, 14 pages.

* cited by examiner

1000

1004

1008

1024

1028

1032

1012

1020

1016

1704

1708

1700

1712

LIQUID DETECTION SENSOR

CROSS-REFERENCE TO RELATED APPLICATIONS

This application claims priority to and the benefit of U.S. Provisional Application No. 63/612,734, filed Dec. 20, 2023, and U.S. Provisional Application No. 63/494,407, filed Apr. 5, 2023 the entirety of which are incorporated herein by reference.

TECHNICAL FIELD

The present disclosure is related to devices, systems, methods, and kits for determining the liquid level in a wearable medical device. More particularly, the present disclosure is related to a sensor for detecting a liquid level in a wearable drug delivery device.

BACKGROUND

Current drawn fill tubes of wearable medical devices have a large footprint which can limit the potential for device size and minimum fill requirement reduction. They also present manufacturing challenges. Additionally, systems and methods for measuring fluid amounts dispensed by wearable medical devices can be cumbersome. Accordingly, wearable medical devices can be improved.

SUMMARY

In an aspect, a system for determining a liquid level in a drug delivery device is presented. The system includes a first spring and a second spring positioned adjacent the first spring. The system includes a rod configured to compress at least the first spring and contact the second spring. The system includes a sensing element in communication with the first spring and the second spring. The sensing element is configured to detect a difference in voltage of at least the first spring. A difference in voltage of at least the first spring corresponds to an amount of liquid drug of the drug delivery device.

In another aspect, an apparatus for a fluid gauge of a drug delivery device is presented. The apparatus includes a rod extending from a plunger end of a drug delivery device, The rod has a first plurality of teeth. The apparatus includes a gear positioned under the rod and having a second plurality of teeth. The first plurality of teeth and the second plurality of teeth are configured to interface with each other. The apparatus includes an encoder, wherein the encoder is configured to correlate a degree of rotation of the gear to an amount of liquid drug dispensed.

In another aspect, a method for fuel gauging of a drug delivery device is presented. The method includes moving a rod of a drug delivery device into contact with a first spring. The method includes contacting, by the rod, a second spring, wherein contacting the second spring produces an electric circuit between the first spring and the second spring. The method includes sensing, by a sensing element in communication with the first spring and the second spring, a difference in voltage of at least the first spring. The method includes calculating, by a processor in communication with the sensing element, an amount of liquid drug od the drug delivery device based on the difference in voltage of a ta least the first spring.

DETAILED DESCRIPTION

Figure 1A:
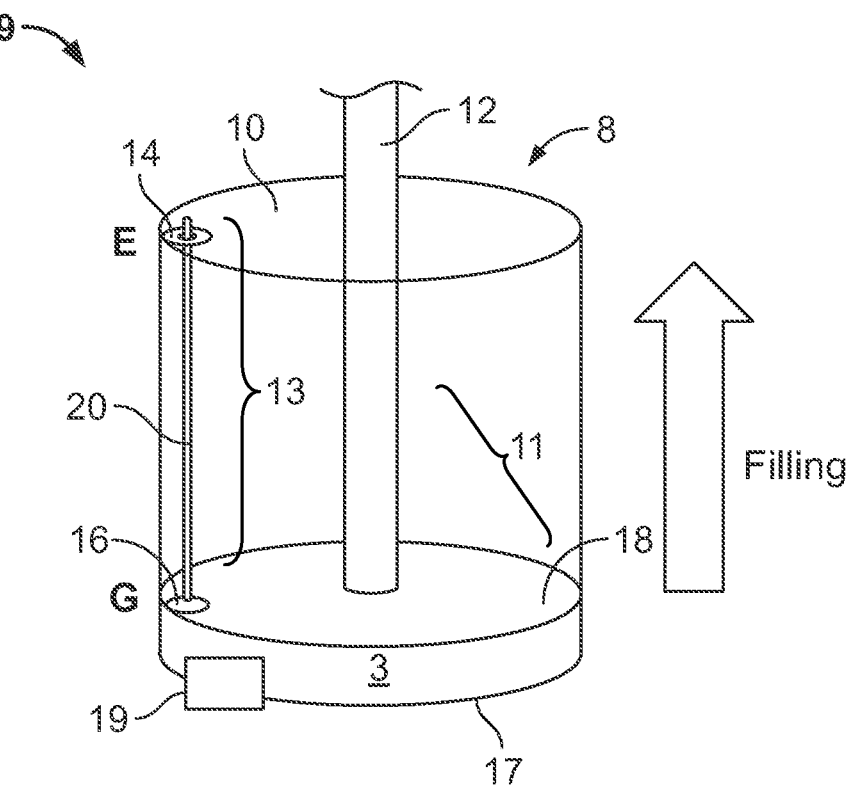
FIGS. 1A-1E illustrate an exemplary embodiment of a reservoir with different levels of liquid suitable for use in a wearable drug delivery device.

This disclosure presents various systems, components, and methods related to a sensor for detecting liquid levels in a reservoir of a medical device, such as a wearable drug delivery device. Each of the systems, components, and methods disclosed herein provides one or more advantages over traditional systems, components, and methods. Various embodiments of sensors for detecting reservoir liquid levels, wearable drug delivery device systems, components, and methods are disclosed herein.

Software related implementations of the techniques described herein may include, but are not limited to, firmware, application specific software, or any other type of computer readable instructions that may be executed by one or more processors.

Hardware related implementations of the techniques described herein may include, but are not limited to, integrated circuits (Ics), application specific Ics (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

As described herein the term "plunger end" refers to the end of a reservoir located adjacent to the plunger when the reservoir is in a full state. For example, the plunger end of the reservoir may abut a plunger seal when the reservoir is full of a liquid. In another example, the plunger end is the end of the reservoir through which the plunger shaft passes therethrough.

As described herein aspects of the current disclosure are related to a sensor for determining a liquid level in reservoir of a wearable drug delivery device. The liquid level may, for example, be the amount of liquid drug remaining in the reservoir of the device. The amount of liquid drug remaining in the reservoir of the wearable drug delivery device may be used by the user, or a processor of the wearable drug delivery device, to determine when the wearable drug delivery device needs to be replaced or refilled. The sensor may determine the liquid level by deterring an electrical resistance or other characteristic based on the location of a plunger in the wearable drug delivery device.

FIGS. 1A-1E illustrate exemplary embodiments of a reservoir system and other components of a wearable drug delivery device incorporating a liquid level sensor. The reservoir system 9 of a wearable drug delivery device may have at least a reservoir 8, plunger 11, and a liquid level sensor 13. The reservoir 8 may include a plunger end 10 as well as a leakproof reservoir base 17. An inlet port 19 may be coupled to and through the leakproof reservoir base 17. The inlet port 19 is operable for filling the reservoir 8 and may include a one-way valve or septum to prevent leakage of the liquid drug 3 from the reservoir 8. The plunger 11 may have a plunger shaft 12 and a plunger seal end 18. The plunger seal end 18 is configured to fit within the reservoir 8 to form a leak proof seal between it and the leakproof reservoir base 17. The plunger shaft 12 is coupled to the plunger seal end 18 and to a drive mechanism coupling (not shown).

The sensor 13 may include a first electrical contact 14, a second electrical contact 16, and a conductive strip 20. In some embodiments, the first electrical contact 14 is located at the plunger end 10 of the reservoir 8. In an example, the first electrical contact 14 is positioned on the exterior of the plunger end 10 of the reservoir 8, while, in another example, the first electrical contact 14 is positioned on the interior of the plunger end 10 of the reservoir 8. In yet another example, the first electrical contact 14 is positioned through the plunger end 10 of the reservoir 8.

In the example of FIGS. 1A-1E, the conductive strip 20 makes contact with the second electrical contact 16, which is located on the plunger seal end 18. The plunger shaft 12 extends from the plunger seal end 18 to a location beyond the plunger end 10 of reservoir 8. The conductive strip 20, for example, may extend from the second electrical contact 16 at least to the first electrical contact 14. In this example, the conductive strip 20 is operable to slide back and forth past the first electrical contact 14 as the plunger 13 moves while the reservoir 8 is filled and unfilled with the liquid drug 3.

Figure 1B:
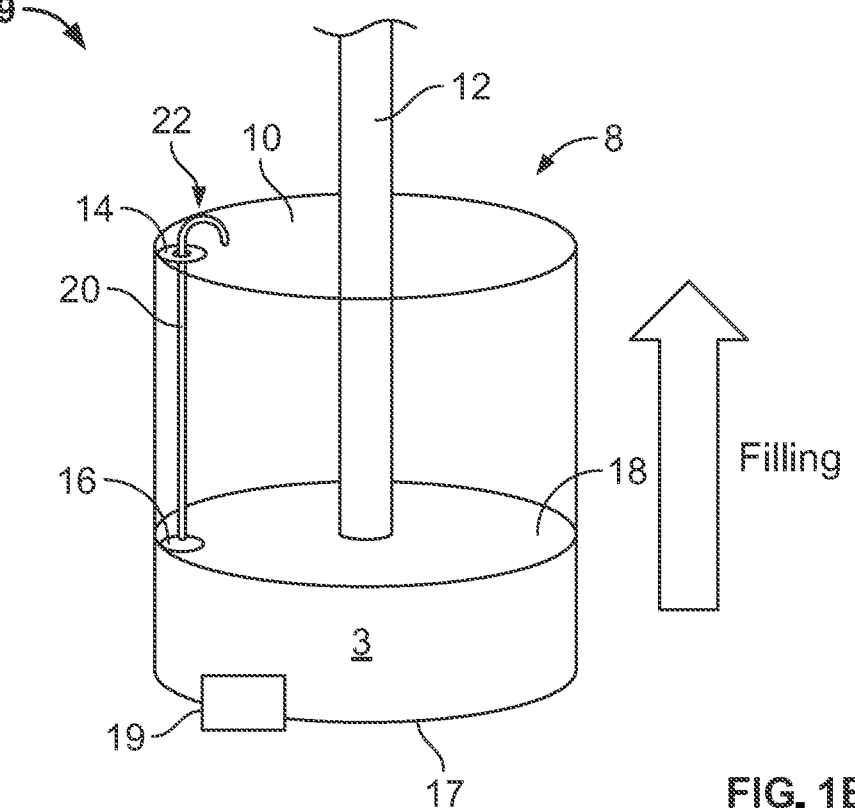
Figure 1C:
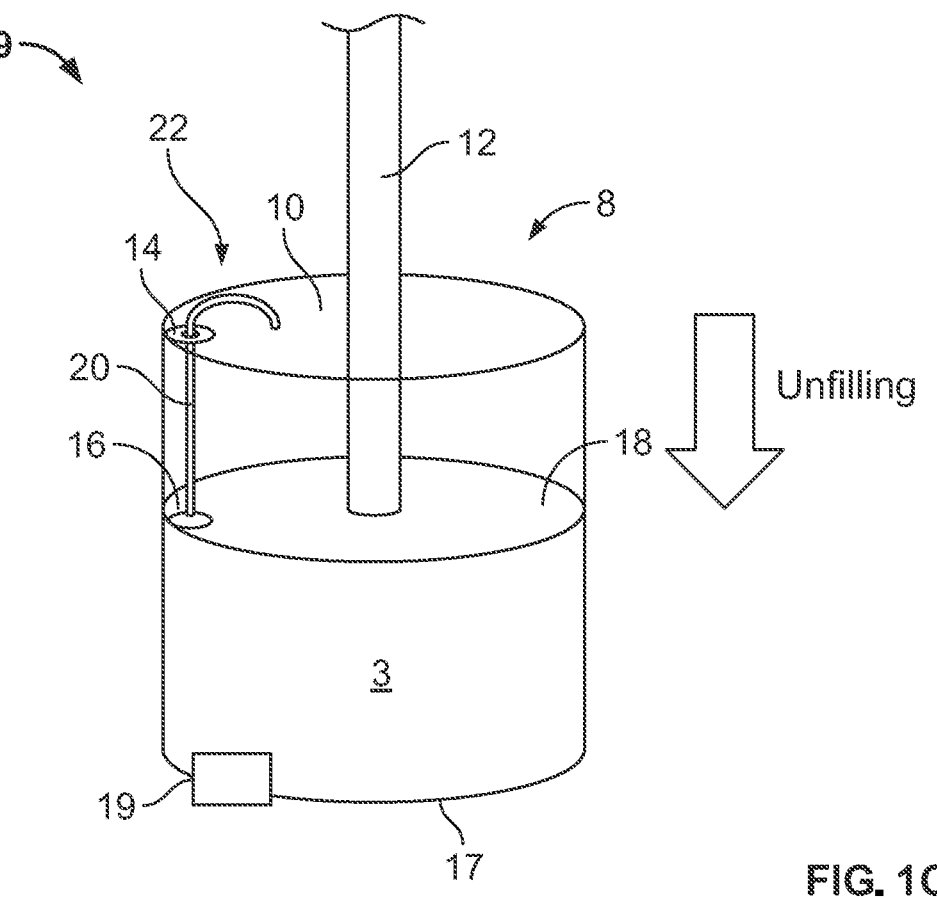
Figure 1D:
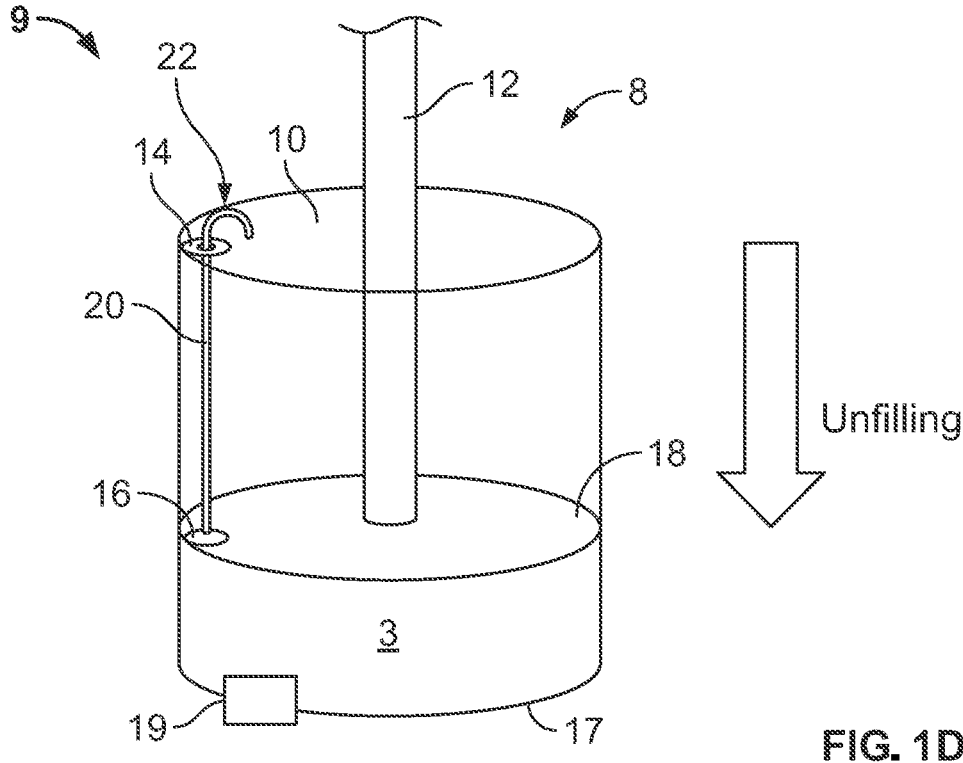

In some embodiments, a portion of conductive strip 20, referred to herein as an overhang portion 22, may, depending upon movement of the plunger 13 extend beyond the first electrical contact 14 as shown, for example, in FIGS. 1B-1D. For example, the overhang portion 22 is longer in the reservoir 8 filled with more liquid in FIG. 1C than the reservoir 8 illustrated in FIG. 1D.

The overhang portion 22 of the conductive strip 20 may be longer when the reservoir 8 is filled with the liquid drug 3. For example, the conductive strip 20 may slide beyond first electrical contact 14 to form an overhang portion 22 as the plunger seal end 18 moves towards the plunger end 10 of reservoir 8 to accommodate the influx of the liquid drug 3 into the reservoir 8.

The conductive strip 20, for example, may be made of a metal material, graphene, carbon nanotubes, or combinations thereof, and may, as an alternative to a strip, also be in the form of a wire, or the like. In some embodiments, the conductive strip 20 is a wire. In some embodiments, as the reservoir 8 fills with the liquid drug 3 through the inlet port 19 the plunger seal end 18 and plunger shaft 12 move towards the plunger end 10 of the reservoir to allow the liquid drug 3 to fill the reservoir 8.

Figure 1E:
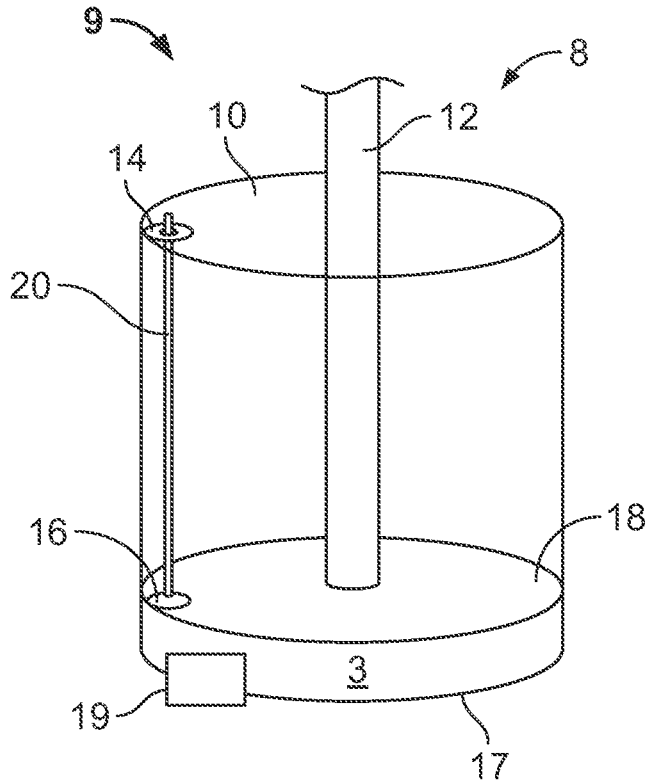

FIGS. 1A-1C illustrate a progression of the liquid drug 3 level within the reservoir 8 as the reservoir is filled. FIG. 1C illustrates a last amount of liquid drug in the reservoir 8 and the response of the liquid level sensor 13 based on the filling examples illustrated in FIGS. 1A and 1B. For example, FIG. 1B illustrates a reservoir 8 filled with more liquid than the reservoir 8 illustrated in FIG. 1A. FIGS. 1C-1E show a progression of the expulsion reservoir 8 with progressively lesser amounts of the liquid drug and the respective response of liquid level sensor 13. For example, the liquid drug 3 may be expelled in response to the plunger 11 being depressed to expel the liquid drug from the reservoir 8.

As the liquid drug level in the reservoir 8 increases as shown by the change in position of the plunger 11 from FIG. 1A to FIG. 1C, the length of overhang portion 22 of the conductive strip 20 may increase. As the liquid level in the reservoir 8 increases, the distance between the first electrical contact 14 and the second electrical contact 16 may decrease because the plunger seal end 18 moves closer to plunger end 10. In some embodiments, a tensioner (not shown in this example) is connected to the first electrical contact 14 to maintain tension in the conductive strip 20.

The example of FIGS. 1A-1E shows how the conductive strip 20 configured to slide past the first electrical contact 14 and the second electrical contact, wherein the conductive strip is in electrical communication with the first electrical contact 14 and the second electrical contact 16. As shown in a later example, the first electrical contact 14 and the second electrical contact 16 may be further coupled to sensor circuitry as described in more detail with reference to a later example.

Figure 2:
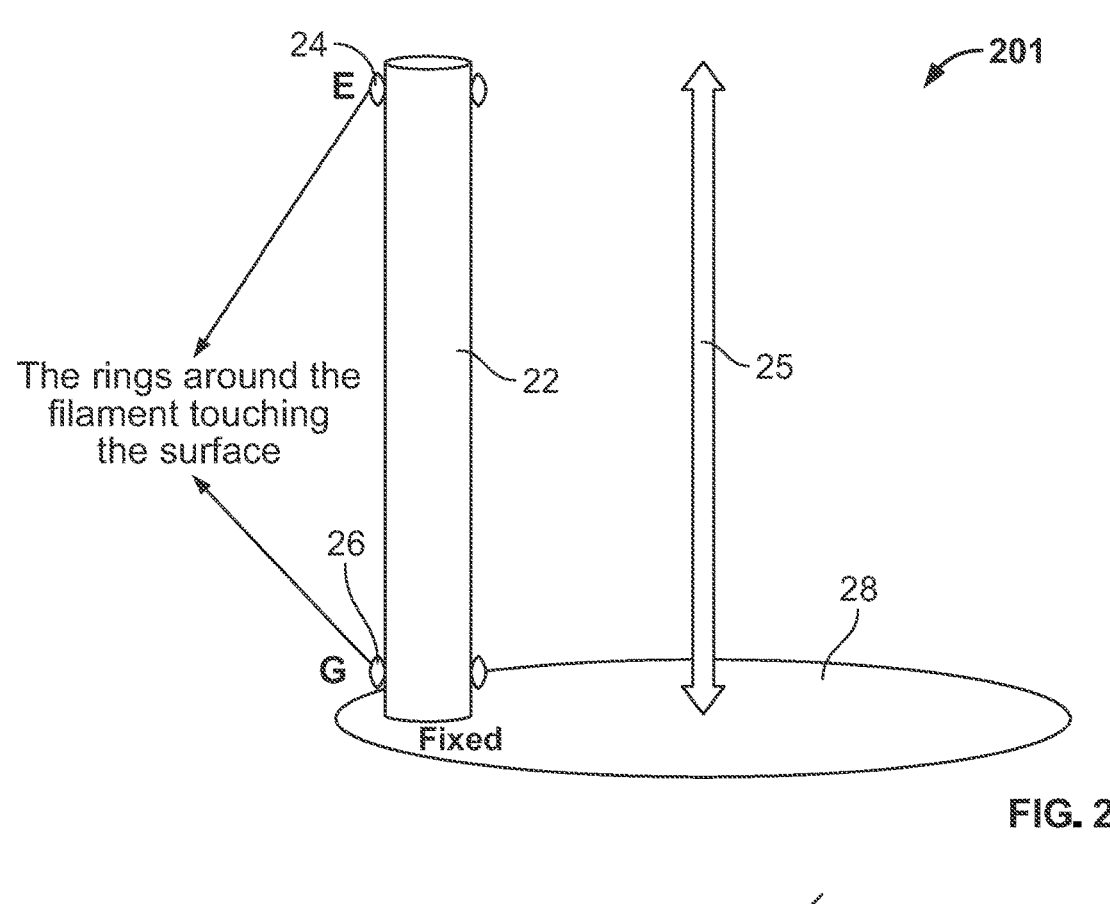
FIG. 2 illustrates an exemplary embodiment of a sensor for use with a reservoir of a wearable drug delivery device.

FIG. 2 illustrates another exemplary embodiment of a liquid level sensor arrangement within a reservoir of a wearable drug delivery device. The liquid level sensor arrangement 201 may include a first electrical contact 24, a second electrical contact 26, and a conductive strip 28. The second electrical contact 26 may be positioned at a plunger seal end 28. The plunger seal end 28 may move upwards towards first electrical contact 24 or downwards away from the first electrical contact 24 in the directions as shown by the arrow 25. In an example, the second electrical contact 26 may be fixed to the plunger seal end 28. In some embodiments, the conductive strip 22 may extend from the first electrical contact 24 to the second electrical contact 26. The conductive strip 24 may be configured similar to the conductive strip 20 as in the example of FIGS. 1A-1E. In the example of FIG. 2, the first electrical contact 24 and the second electrical contact 26 may have rings around the conductive strip 28 or be a filament within a ring touching a surface of conductive strip 22. Alternatively, the first electrical contact 24 and the second electrical contact 26 may be respectively have a generally ring-like structure. The first electrical contact 24 and the second electrical contact 26 are made of a high conductivity material that minimizes undesirable resistance. In an example, the conductive strip 22 may pass through or roll through a ring coupled to the first electrical contact 24. For example, one or more wires may be soldered, glued, or otherwise connected to one or more rings to connect the first electrical contact 24 and the second electrical contact 26 to a sensor processing component.

Figure 3:
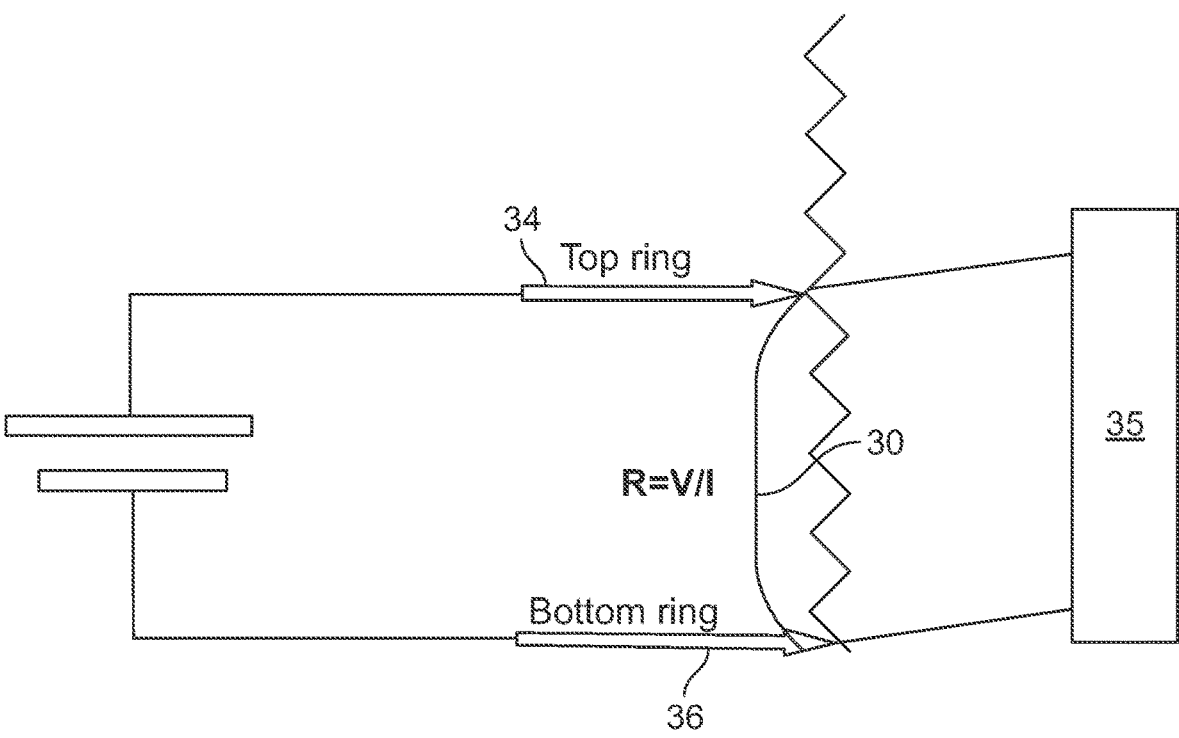
FIG. 3 illustrates an exemplary electrical circuit useful for explaining operation of a sensor for determining liquid levels in the examples described herein.

FIG. 3 illustrates an exemplary electrical circuit representation suitable for use in determining a liquid level in a reservoir of a wearable drug delivery device. In some embodiments, a sensor 310 detects a variation of an electrical characteristic, such as electrical resistance, between a first electrical contact 34 and second electrical contact 36. The variable electrical characteristic (e.g., electrical current or voltage) may be detected along an electric path extending from the first electrical contact 34 (also referred to as top ring, such as 24 in FIG. 2) through conductive strip 30 to second electrical contact 36 (also referred to as bottom ring, such as 26 in FIG. 2). The variable electrical characteristic may be used to determine a resistance (e.g., the R in Ohm's law R=V/I, where V is voltage, and I is current). For example, a current (I) may flow from at least the first electrical contact 34 through the conductive strip 30 to the second electrical contact 36. The current from the first electrical contact 34 through the conductive strip 30 to the second electrical contact 36 may be a low current (e.g., tenths of milliamperes, microamperes or the like). In some embodiments, a sensor 35 may have circuitry that is operable to detect changes in voltage between the first electrical contact 34 and the second electrical contact 36 while the current is known. With the detected value of the voltage, or the detected change in the value of the voltage, the resistance may be determined according to Ohm's law by the circuitry in the sensor 35.

In an example, the electrical resistance between the first electrical contact 34 and the second electrical contact 36 may increase as the length of conductive strip 30 increases between the first electrical contact 34 and the second electrical contact 36. Alternatively, the electrical resistance between the first electrical contact 34 and the second electrical contact 36 may decrease as the length of conductive strip 30 decreases between the first electrical contact 34 and the second electrical contact 36.

Additionally, or alternatively, a voltage may be detected between the first electrical contact 34 and the second electrical contact 36 that changes based on the length of the conductive strip 30. In such an example, the resistance may be determined by multiplying the resistivity of the material forming the conductive strip 30 by the length of the conductive strip 30 and dividing the result by the area of the conductive strip 30, or the like. Alternatively, a lookup table may be established having reference values, such as a reference resistance, a reference voltage, a reference current, a reference conductive strip length, some other reference value, or a combination of the reference values, which correspond to an amount of a liquid drug that is remaining in the reservoir or that has been expelled from the reservoir. The look up table may be stored in a memory coupled to the sensor circuitry 35, to a processor coupled to the sensor circuitry 35, or the like.

Figures 4A, 4B:
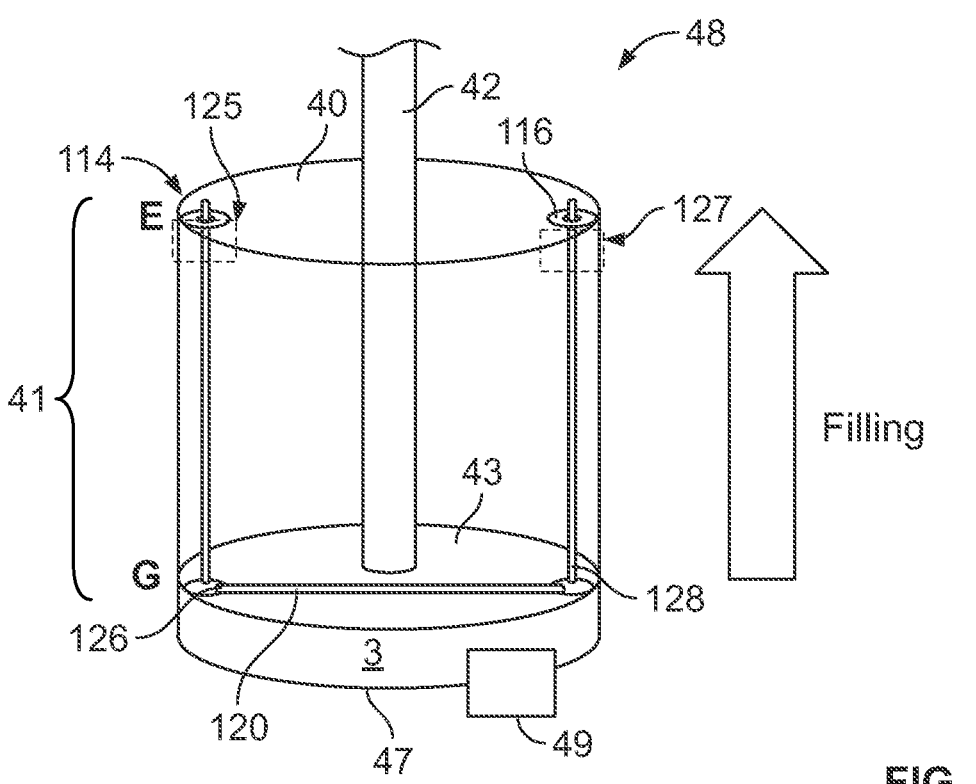
FIGS. 4A-4E illustrate an exemplary embodiment of another sensor suitable for identifying different levels of liquid in a reservoir of a drug delivery device.

FIGS. 4A-4E illustrate another exemplary embodiment of a sensor arrangement for a reservoir of wearable drug delivery devices. The reservoir 48 of a wearable drug delivery device may have a plunger end 40 and a leakproof reservoir base 47. A plunger 41 may include a plunger shaft 42, and a plunger seal end 43. The plunger seal end 43 is configured to fit within the reservoir 48 to form a leak proof seal between it and the leakproof reservoir base 47. The plunger shaft 42 is coupled to the plunger seal end 43 and to a drive mechanism coupling (not shown). The reservoir 48 may include a first electrical contact 114, a second electrical contact 116, a conductive strip 120, a first aligning member 126, and a second aligning member 128. As shown in FIG. 4A, for example, the first electrical contact 114 may be fixed to the plunger end 40. An inlet port 49 may be coupled to and through the leakproof reservoir base 47. The inlet port 49 is operable for filling the reservoir 48 and may include a one-way valve or septum to prevent leakage of the liquid drug 3 from the reservoir 48.

The sensor arrangement may include a configuration in which the second electrical contact 116 may be fixed to the other side of the plunger end 40. For example, a first aligning member 126 may be attached to a first portion of the plunger seal end 43. A second aligning member 128 may be attached to a second portion of the plunger seal end 43. When the first aligning member 126 and the second aligning member 128 are present, the conductive strip 120 extends down from the first electrical contact 114 to the first aligning member 126 across a part of the plunger seal end 43 to the second aligning member 128 and up to the second aligning member 128. Additionally, the conductive strip 120 may be held in a preset state of tension between the first electrical contact 114 and the second electrical contact 116 by a tensioner (shown in a later example). Additionally, or alternatively, the conductive strip 120 may be held by one or more tensioners (shown in a later example) in a preset state of tension between the first electrical contact 114, the first aligning member 126, the second aligning member 128, and the second electrical contact 116.

In a further example, the conductive strip 120 may be configured slide past at least one of the first electrical contact 114, the second electrical contact 116, or both the first electrical contact 114 and the second electrical contact 116. When the plunger seal end 43 moves towards the plunger end 40 as the reservoir 48 fills with liquid, the conductive strip 120 may have a first loose end 122 and a second loose end 124 extending from the first electrical contact 114 and the second electrical contact 116, respectively, as shown, for example, in FIG. 4B. In some embodiments, the variable electrical characteristic detected between the first electrical contact 114 and the second electrical contact 116 excludes any contribution from the first loose end 122 and the second loose end 124 of the conductive strip 120 as the length of conductive strip 120 that forms the respective first loose end 122 and the second loose end 124 is an open circuit.

In another embodiment, an optional first tensioner 125 may be coupled to the first electrical contact 114 and an optional second tensioner 127 may be coupled to the second electrical contact 116. The optional first tensioner 125 and the optional second tensioner 127 are only shown in FIG. 4A for case of illustration, but it should be understood that the optional first tensioner 125 and the optional second tensioner 127 may appear in FIGS. 4B-4E as well. The first and second tensioners 125, 127 may be configured to hold conductive strip 120 in a preset state of minimal tension. The preset state of minimal tension may be maintained as the plunger seal end 43 moves up and down within the reservoir 48, filling the reservoir 48 with the liquid drug (not shown in FIG. 4A) and expelling the liquid drug from the reservoir 48.

Figures 4C, 4D:
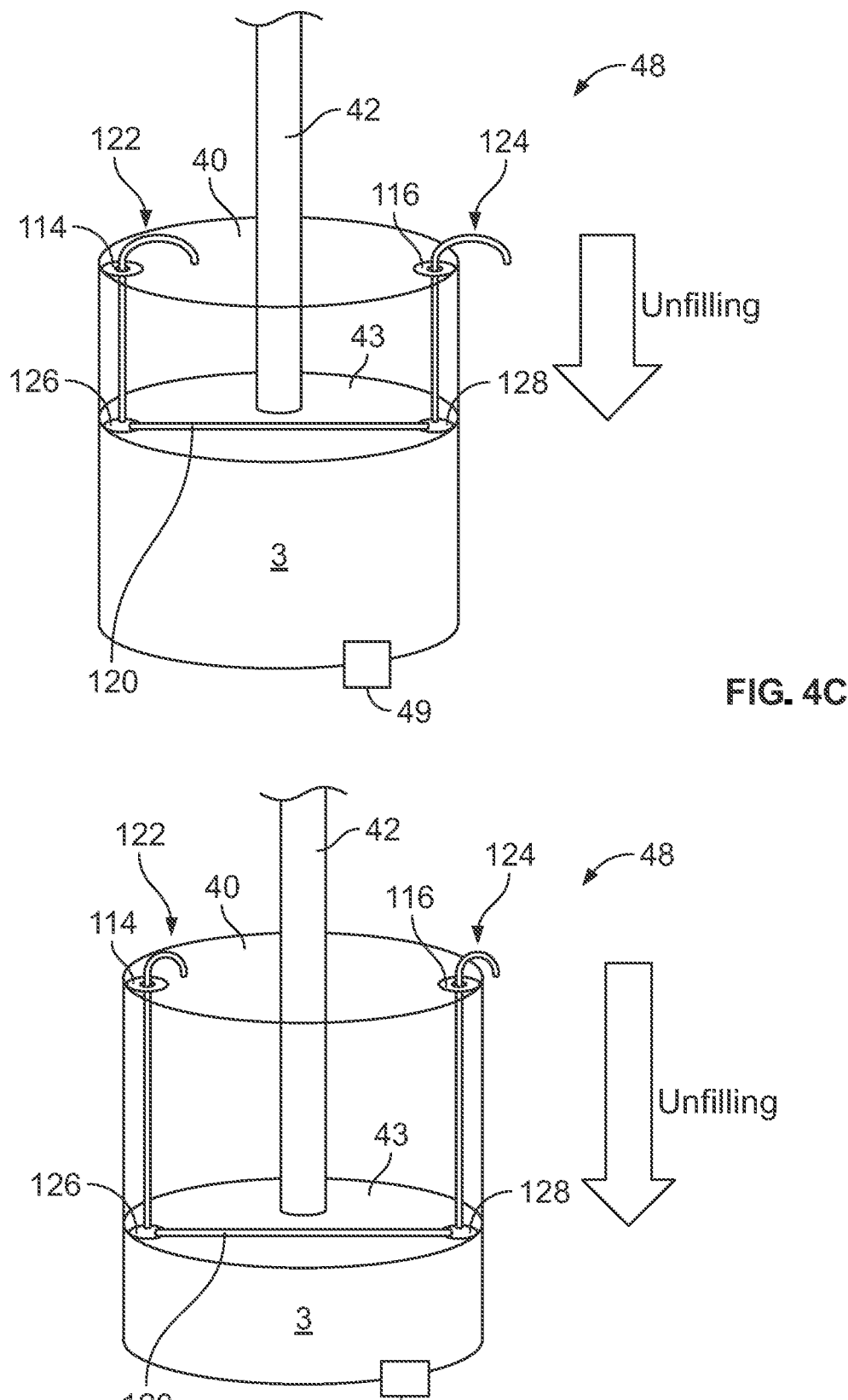
Figure 4E:
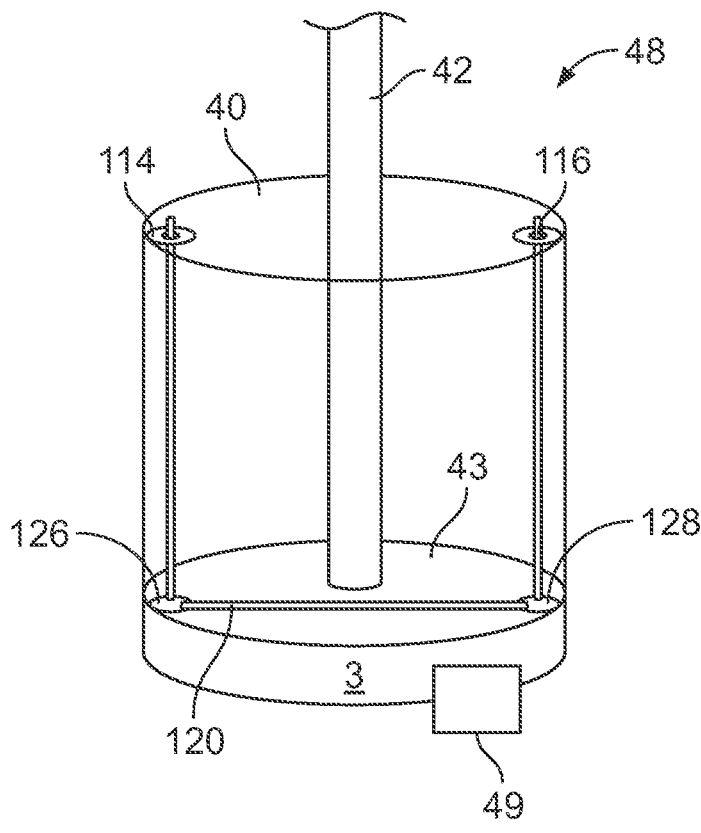

FIGS. 4A-4C illustrated a progression of the reservoir 48 of a wearable drug delivery device as it is filled with increasing levels of a liquid drug 3. In the progression shown in FIGS. 4A-4C, FIG. 4C has the greatest amount of the liquid 3. The amount of the liquid drug 3 in the reservoir 8 shown in FIG. 4B may be greater than the amount shown in FIG. 4A and less than the amount shown in FIG. 4C. As shown in FIG. 4C, as the liquid drug 3 level in the reservoir 48 increases, the length of the first loose end 122 and the second loose end 124 may increase. FIGS. 4C-4E show a progression of the liquid drug 3 level as it is expelled from the reservoir 48. The liquid may be expelled by the plunger 41 being depressed into the reservoir 48 to expel the liquid drug 3 from the reservoir 48. The amount of the liquid drug 3 in reservoir 48 shown in FIGS. 4D and 4E is progress less than the amount of the liquid drug 3 shown in FIG. 4C.

FIGS. 5A-5E illustrate various views of an exemplary embodiment of a sensor arrangement for a reservoir 58.

Figure 5A:
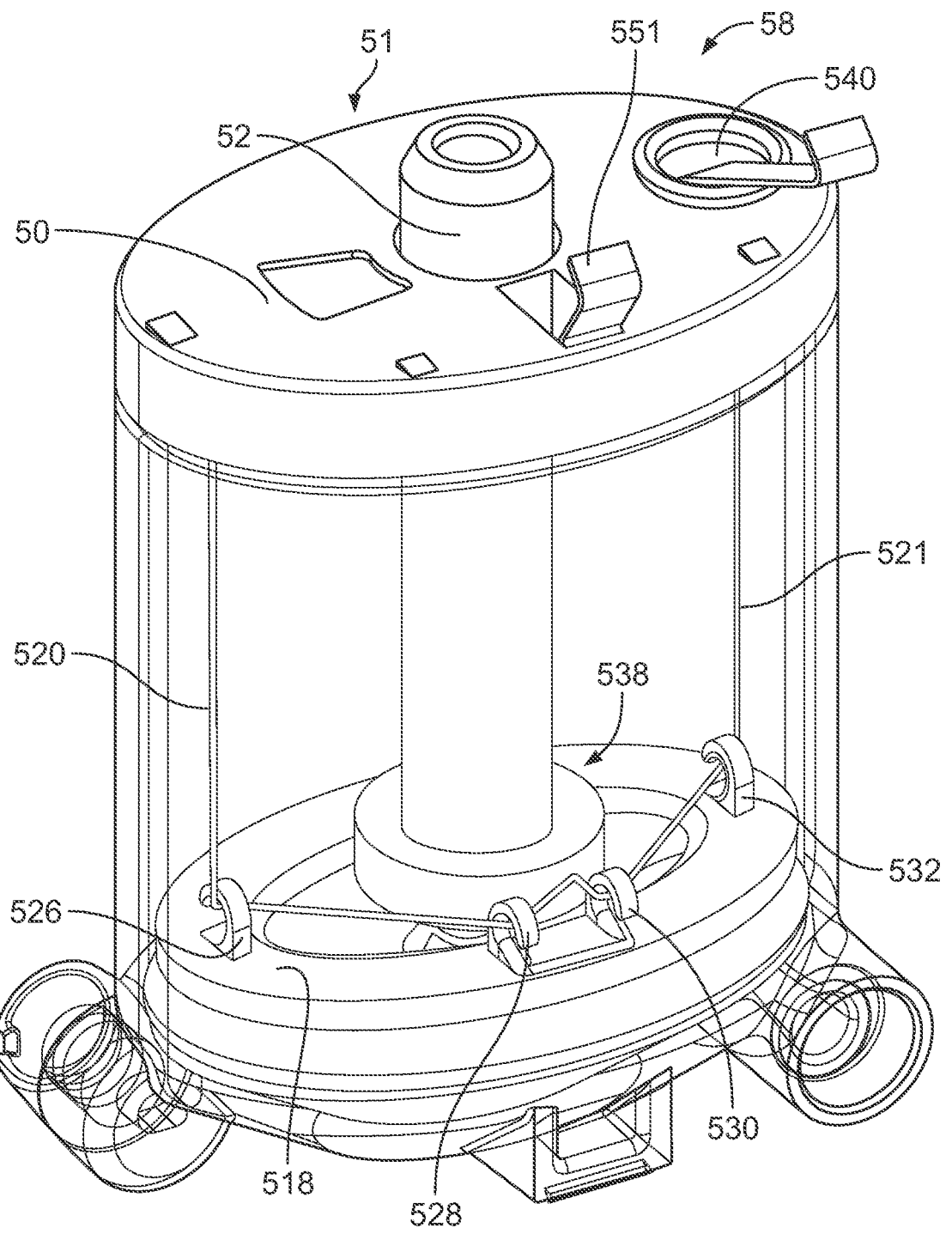
FIGS. 5A-5E illustrate various views of an exemplary embodiment of an empty reservoir of a wearable drug delivery device.

As shown in FIG. 5A, the reservoir 58 is shown in a state of substantially empty or zero liquid drug level. The reservoir 58 may have a first conductive strip 520 extending from a first electrical to a first aligning member 526 and on to a second aligning member 528 and to a tensiometer 538. In some embodiments, a protuberance 551 extending from a reservoir cover 50 is a first electrical contact. The reservoir may have a second conductive strip 521 extending from the tensiometer 538 to a third aligning member 530, and subsequently to a fourth aligning member 532, and upwards to a second electrical contact (not shown). In some embodiments, the electrical contact is connected to a tensioner 540. In some embodiments, the electrical contact is located beneath the reservoir cover 50.

In some embodiments, first conductive strip 520 and the second conductive strip 521 are a single component. In some embodiments, first conductive strip 520 and the second conductive strip 521 are separate components. In some embodiments, the resistance is measured between the first electrical contact and the second electrical contact.

In the example illustrated in FIG. 5A, the first aligning member 526, the second aligning member 528, the third aligning member 530, and the fourth aligning member 532 may all be fixedly disposed on a surface of the plunger seal end 518. The first aligning member 526 and the fourth aligning member 532 may be disposed on the outer ends of the surface of the plunger seal end 518, while the second aligning member 528 and the third aligning member 530 may be disposed closer together on an inner end of the surface of the plunger seal end 518. As shown, the first aligning member 526 and the fourth aligning member 532 may be disposed on either side of the plunger shaft 52. In some embodiments, the second aligning member 528 and the third aligning member 530 are made of a conductive material. In some embodiments, the first aligning member 526 and the fourth aligning member 532 are made of a non-conductive material.

In some embodiments, the reservoir 58 may include one or more tensioners 540. The tensioner 540 may hold the second conductive strip 521 in a preset state of minimal tension as it traverses through each of the alignment members. The tensioner 540 may, for example, be a small spring on a wheel configured to apply tension to a portion of the second conductive strip 521 by pressing the wheel against the second conductive strip 521. Of course, other forms of applying tension to the second conductive strip 521 known to one skilled in the art are considered. In some embodiments, the tensioner 540 is located inside of the reservoir 58. In some embodiments, the tensioner 540 is located external to the reservoir 58. In some embodiments, the tensioner 540 abuts the inner or outer surface of the reservoir 58.

In some embodiments, at least one of the first aligning member 526, the second aligning member 528, the third aligning member 530, or the fourth aligning member 532 is a hook configured to hold at least one of the first conductive strip 520 and the second conductive strip 521. In another embodiment, at least one of the first aligning member 526, the second aligning member 528, the third aligning member 530, or the fourth aligning member 532 is a loop configured to hold at least one of the first conductive strip 520 and the second conductive strip 521. Alternatively, at least one of the first aligning member 526, second aligning member 528, the third aligning member 530, or the fourth aligning member 532 is generally a spring washer, a U-bolt, an eye bolt, a hook, a loop, a washer, a loop clamp, a routing clamp, a standoff clamp, a carabiner, a rope thimble, a clevis-end plug-lock, an eye-end plug lock, a swivel-hook-end plug lock, a feed through end fitting, or any other fitting capable of aligning at least one of the first conductive strip 520 and the second conductive strip 521. The respective aligning members 526, 528, 530 and 532 may formed (e.g., molded or by welding) into plunger seal end 518 as an integral part of the surface of the plunger seal end 518. As further shown in FIG. 5A, the aligning members 526 and 532 have open faces that open in the direction opposite from (or away from) the other aligning members 528 and 530. In an example, the radius of the open face of aligning member 526 permits the first conductive strip 520 to exit the aligning member 526 at an angle from aligning member to engage an open face of the second alignment member 528. In some embodiments, aligning members 530 and 532 are configured similarly in structure and layout to aligning members 526 and 528.

In some embodiments, the reservoir 58 has a tensiometer 538 disposed around the plunger shaft 52. In some embodiments, the tensiometer 538 connects with the first conductive strip 520 and the second conductive strip 521 at the plunger seal end 518. In some embodiments, the tensiometer 538 acts as a potentiometer to provide a variable electrical resistance. In an operational example, at least one of the first conductive strip 520 and the second conductive strip 521 may apply a different level of tension on the tensiometer 538 when the reservoir 58 is empty versus when the reservoir 58 is full, or even partially filled.

Figure 5B:
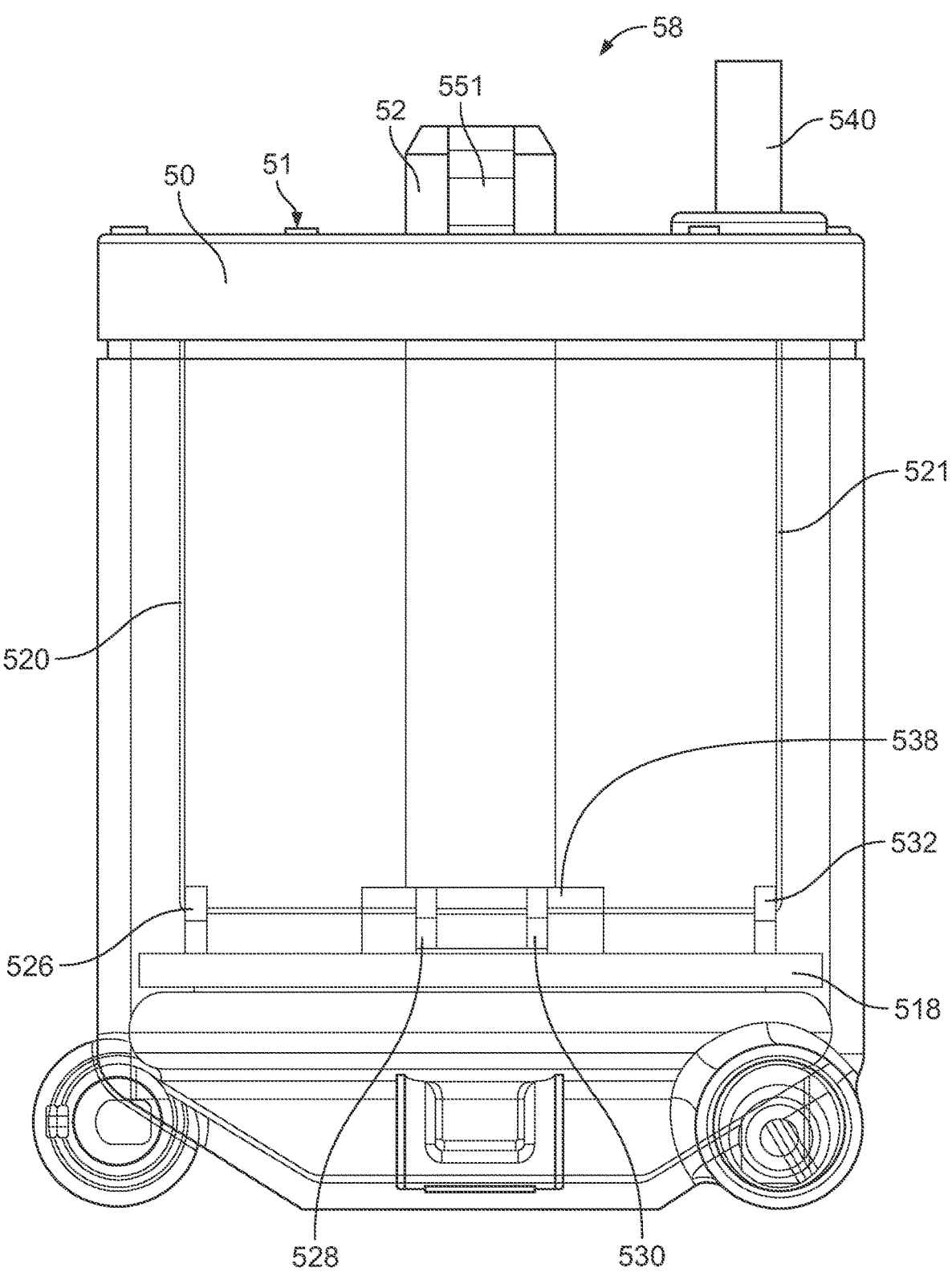

As shown in FIG. 5B, a reservoir 58 is shown in a state of substantially full liquid drug level. When the reservoir 58 is full of liquid, the plunger seal end 8 is located adjacent to a reservoir plunger end 51. For example, when the reservoir 58 is empty, at least one of the first conductive strip 520 and the second conductive strip 521 do not cause a turn or rotation of the tensiometer 538. For example, FIG. 5C illustrates how the turns of the tensiometer coil or spring are evenly spaced apart and the connection between the turns and the first conductive strip 520 is closest to the third alignment member 530.

Figures 5C, 5D:
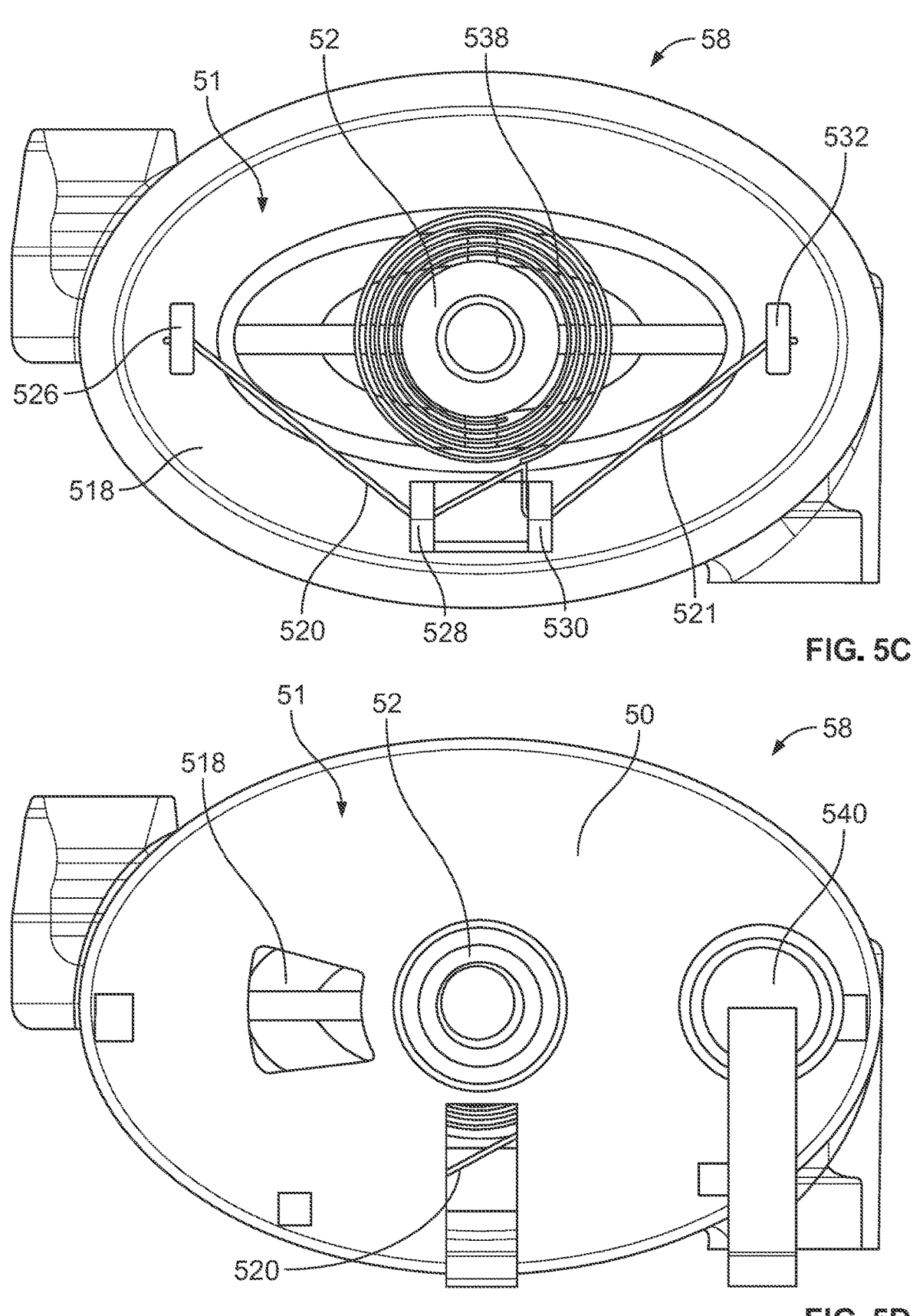

FIG. 5D illustrates an example of a reservoir from a view facing the reservoir cover 50. When the plunger seal end 518 moves closer to the plunger end 51 or reservoir cover 50, such as when the device is filling with liquid, the spring of the tensiometer 538 is configured to pull a greater portion of the first conductive strip 520 and the second conductive strip 521 around the circumference of the plunger shaft (see the example shown in FIG. 6C). As the reservoir 58 fills the connection between the first conductive strip 520 and the tensiometer 538 rotates around the tensiometer spring from a location adjacent to the third alignment member and into a location between the second alignment member 528 and the third alignment member 530. Accordingly, the potential (i.e., resistance of the potentiometer) of the tensiometer 538 changes.

In the example, the measured electrical resistance may be correlated or correspond to a liquid level in the reservoir 58. Alternatively, or additionally, the measured electrical resistance is used to calculate a liquid level in the reservoir 58.

In the example of FIG. 5C, at least a portion of the tensiometer 538 is disposed between the second aligning member 528 and the third aligning member 530. In some embodiments, at least one of the first conductive strip 520 and the second conductive strip 521 is at least partially wrapped around the plunger shaft 52. Alternatively, at least one of the first conductive strip 520 and the second conductive strip 521 may be wrapped several times around the plunger shaft 52. In some embodiments, the increased length of at least one of the first conductive strip 520 and the second conductive strip 521 resulting from wrapping it around the plunger shaft 52 provides a more accurate determined resistance, determined liquid level, or combinations thereof.

Figure 5E:
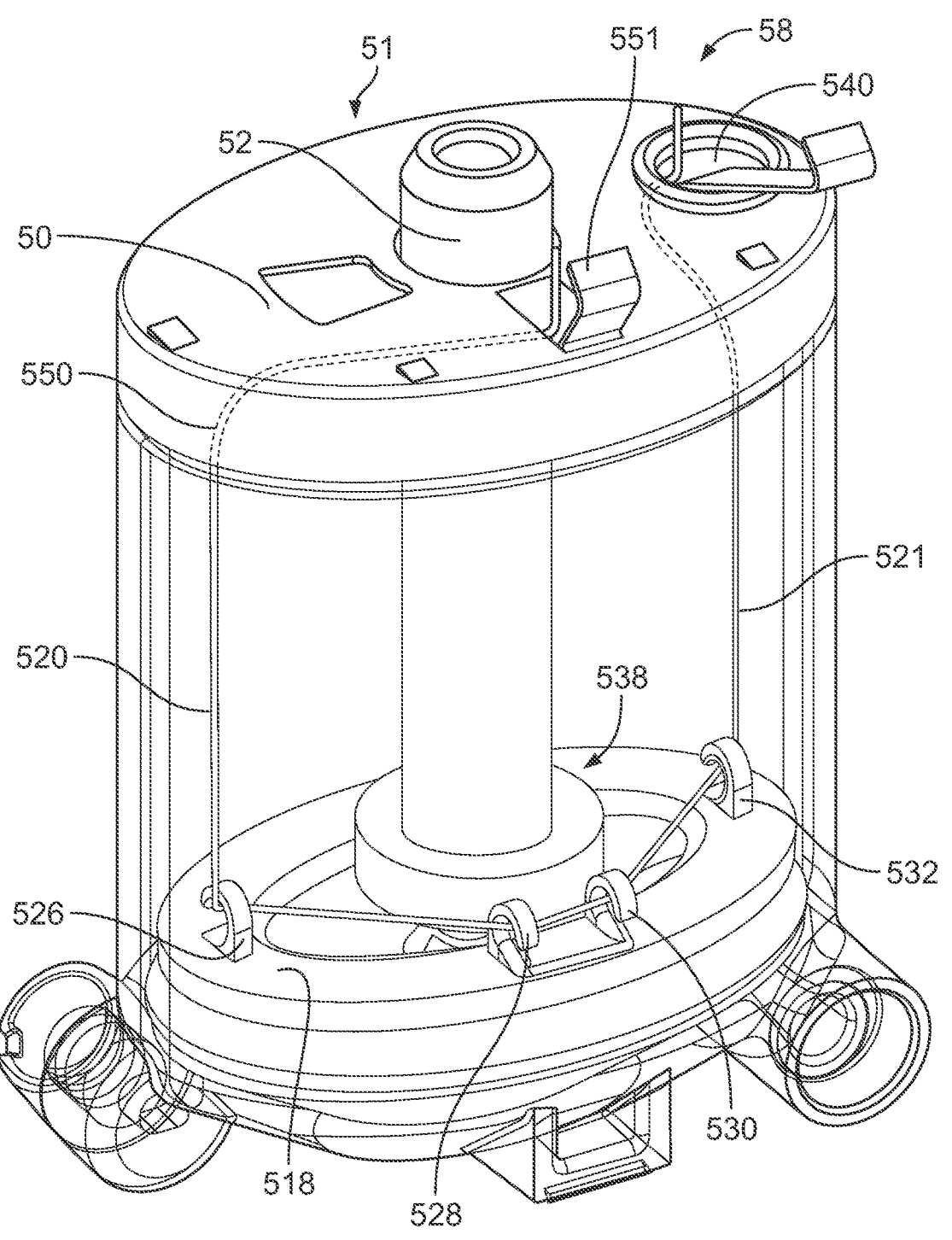

FIG. 5E illustrates an example of an electrical current path 550 which passes through at least a portion of the reservoir 58. The electrical current may flow from the tensioner 540 through to the second conductive strip 521, to the third aligning member 530, to the second aligning member 528, through the first conductive strip 520, and to a protrusion 551 connected to the reservoir cover 50. In some embodiments, the tensiometer 538 is made of a non-conductive material. In some embodiments, the tensiometer 538 created discontinuity between the first conductive strip 520 and the second conductive strip 521.

Figure 6A:
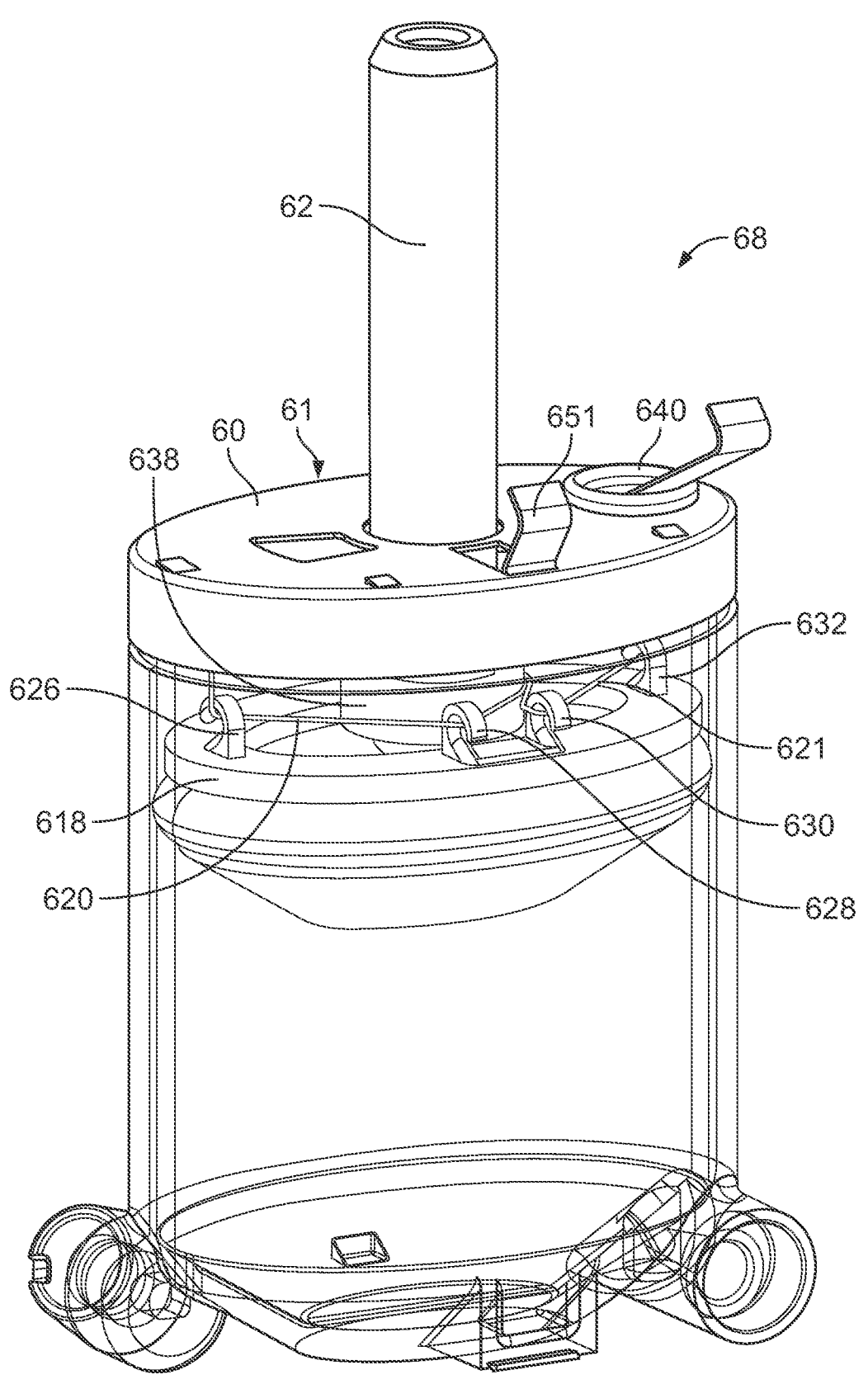
FIGS. 6A-6E illustrate various views of an exemplary embodiment of a filled reservoir of a wearable drug delivery device.

FIGS. 6A-6E illustrate various views of an exemplary embodiment of a reservoir 68 at least partially filled with a liquid. As shown in FIG. 6A, the reservoir 68 may include a first alignment member 626, a second alignment member 628, a third alignment member 630, and a fourth alignment 632. The reservoir may include a tensioner 640. FIG. 6A shows an example where the reservoir 68 is over half full of the liquid drug 3. The first alignment member 626, the second alignment member 628, the third alignment member 630, and the fourth alignment 632 are similar in structure and function to the first alignment member 526, the second alignment member 528, the third alignment member 530, and the fourth alignment 532 described in the example of FIGS. 5A-5E.

Figure 6B:
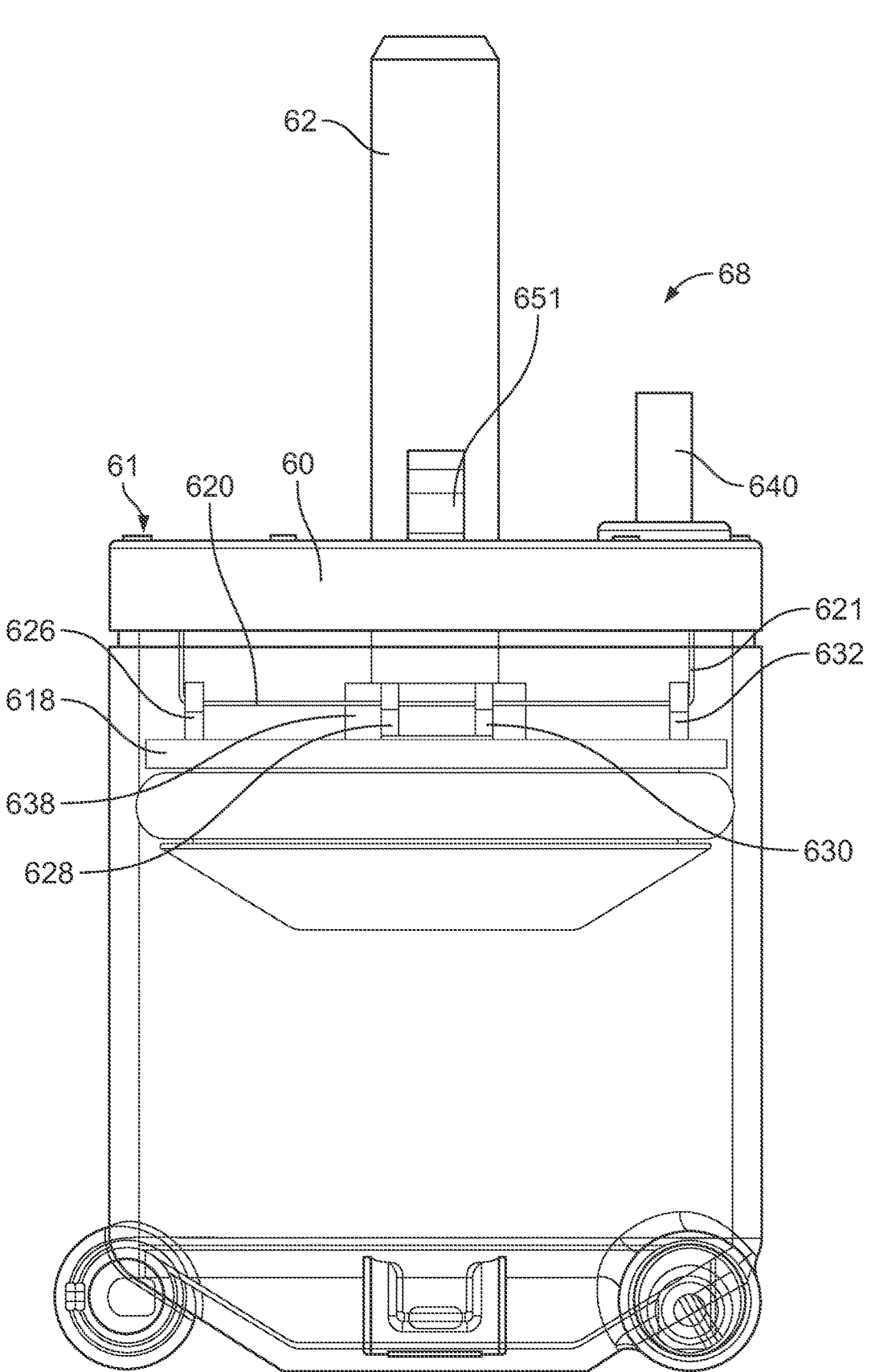
Figures 6C, 6D:
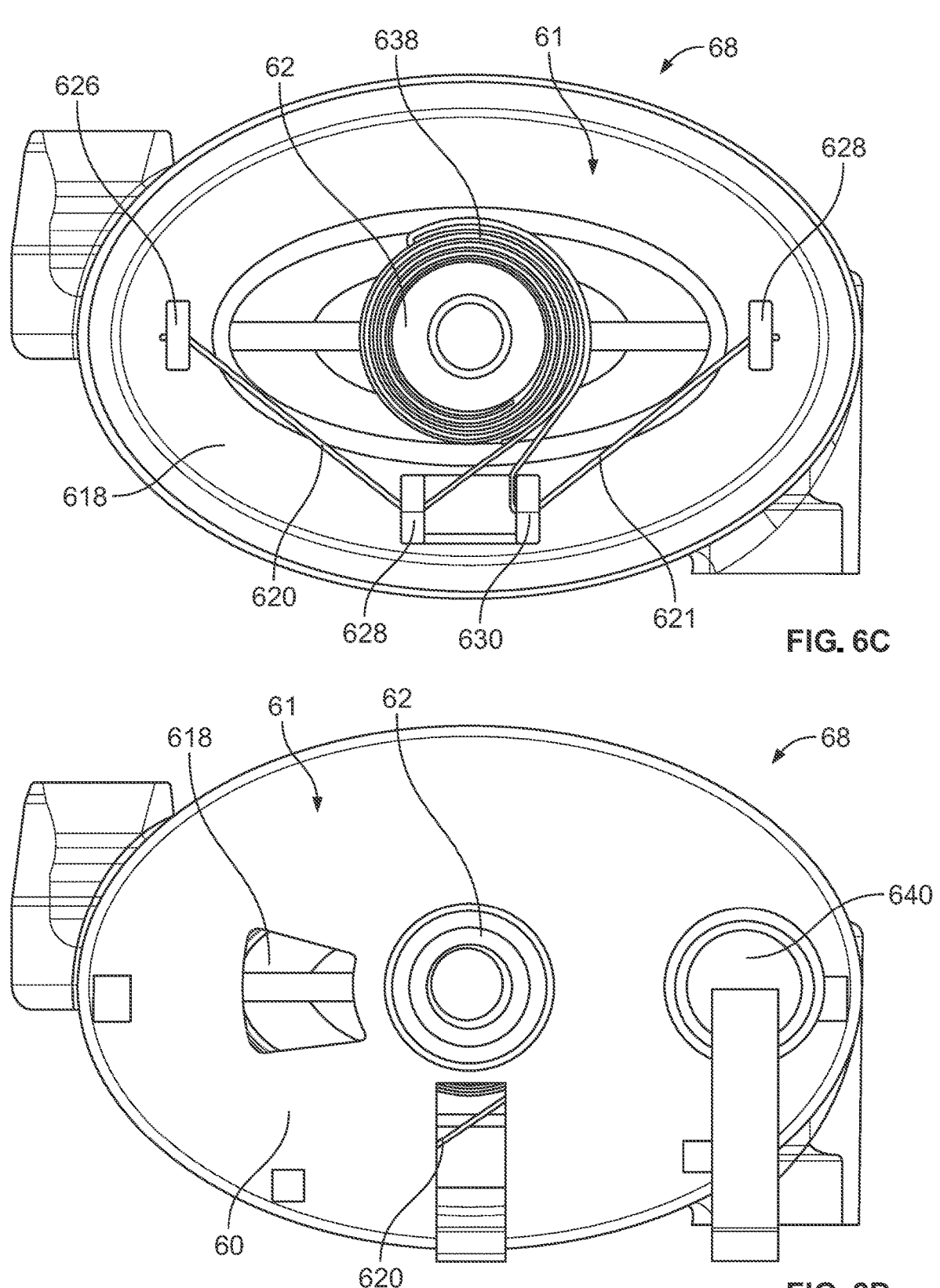

As shown in FIG. 6B, for example, the plunger seal end 618 may move closer to the plunger end 61 because the lower portion of the chamber is filled with liquid. In some embodiments, as the plunger seal end 618 moves closer to the plunger end 61 tension decreases in the first conductive strip 620 between the first electrical contact (not shown) and the first aligning member 626. In some embodiments, reduction in tension of the first conductive strip 620 is picked up by the tensiometer 638. In some embodiments, the first conductive strip 620 at least partially winds around plunger shaft 62 in the tensiometer 638 as shown, for example in FIG. 6C. In some embodiments, the winding of at least one of the first conductive strip 620 and the second conductive strip 621 around tensiometer 638 causes the tensiometer 638 to at least partially rotate around the plunger shaft 62. In some embodiments, the rotation of the tensiometer 638 results in a determined electrical variable that is different from the determined variable of the reservoir 68 at a different liquid level. In some embodiments, the rotation of the tensiometer 638 is used to determine an electrical resistance. In some embodiments, the determined electrical resistance is correlated with or used to determine a liquid level in the reservoir 68. FIG. 6D illustrates an example of a reservoir from a view facing the reservoir cover 60.

Figure 6E:
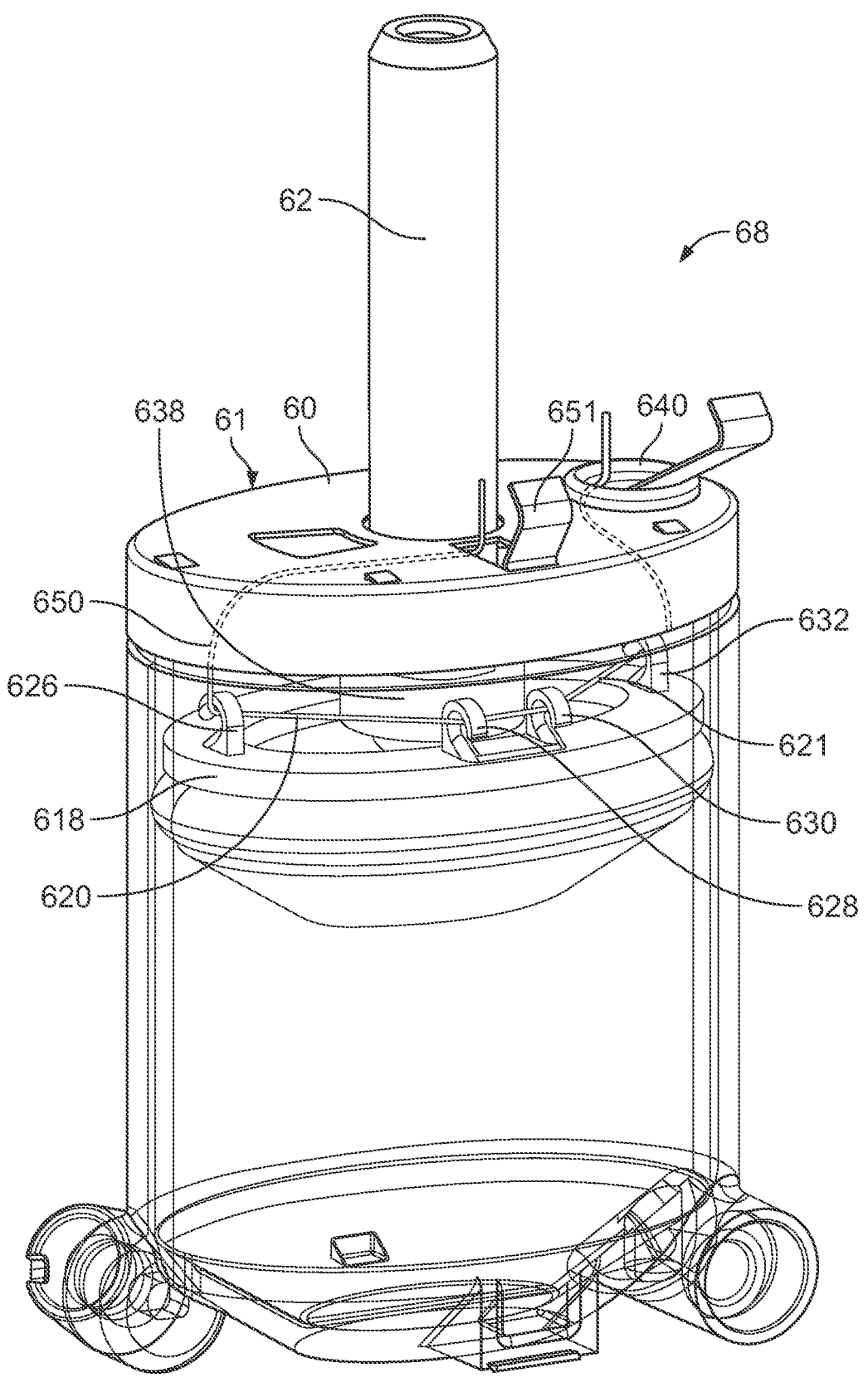

FIG. 6E illustrates an example of an electrical current path 650 which passes through at least a portion of the reservoir 68. The electrical current may flow from the tensioner 640 through to the second conductive strip 621, to the third aligning member 630, to the second aligning member 668, through the first conductive strip 620, and to a protrusion 651 connected to the reservoir cover 60. In some embodiments, the tensiometer 638 is made of a non-conductive material. In some embodiments, the tensiometer 638 created discontinuity between the first conductive strip 620 and the second conductive strip 621.

Figure 7A:
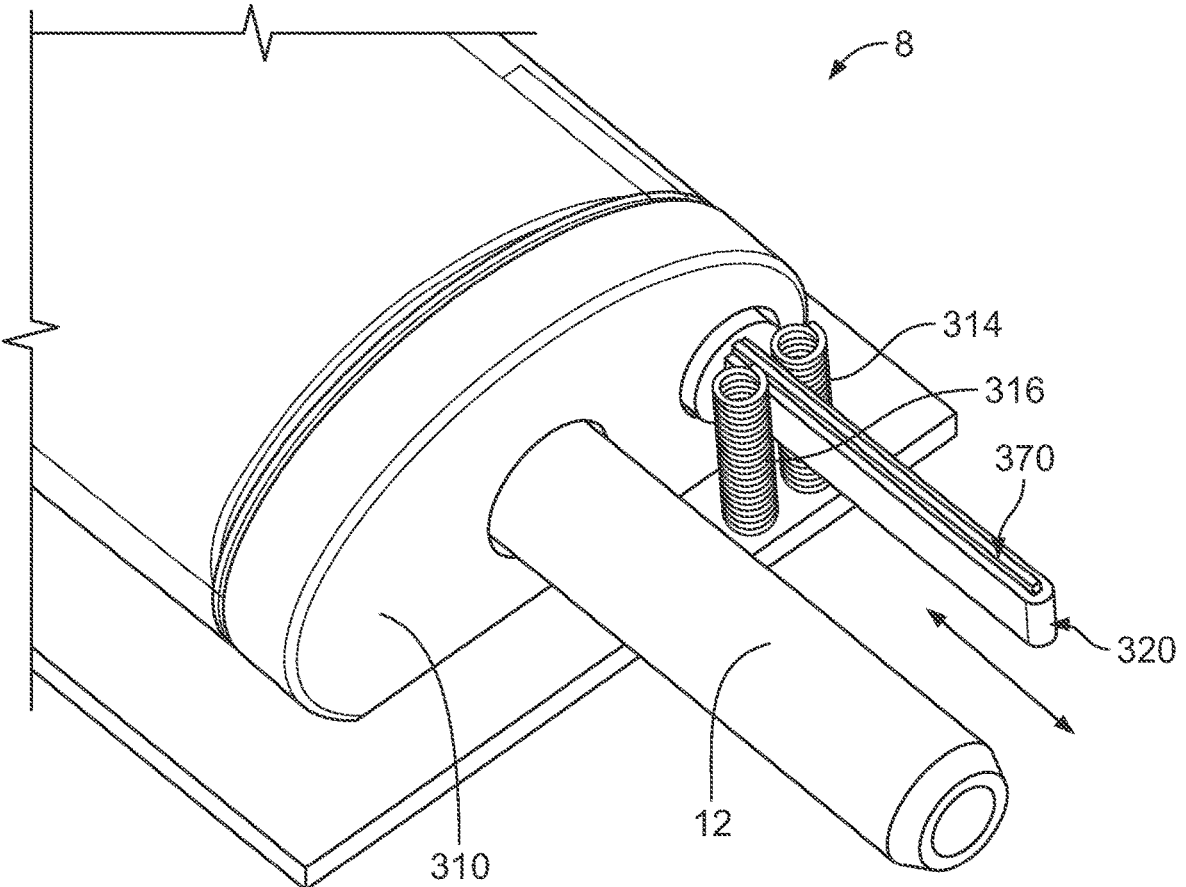
FIGS. 7A and 7B illustrate an exemplary embodiment of a reservoir of a wearable drug delivery device with a sensor for determining a liquid level of the reservoir.
Figure 7B:
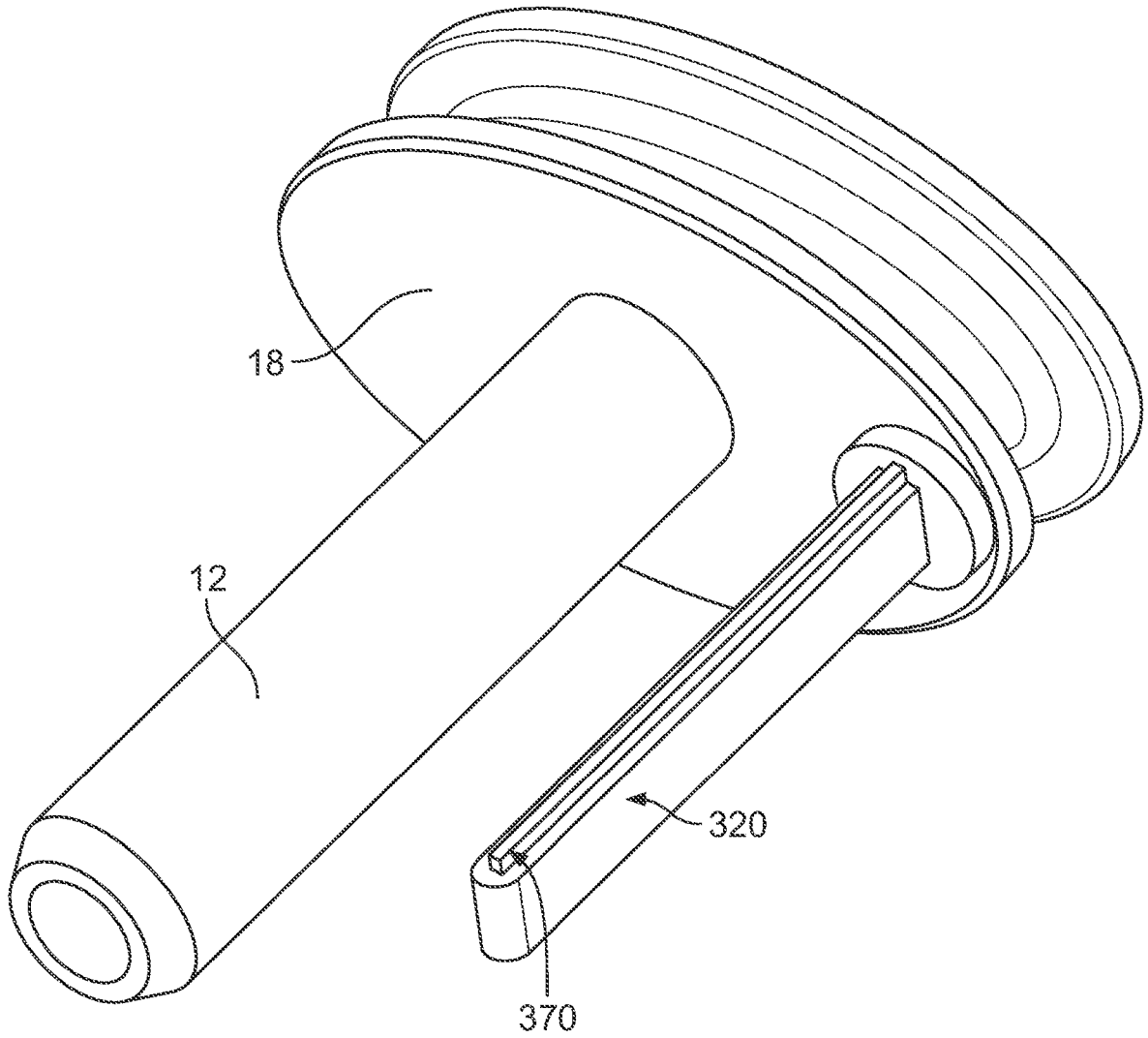

FIGS. 7A and 7B illustrate an exemplary embodiment of a reservoir of a wearable drug delivery device with a sensor for determining a liquid level of the reservoir. For example, FIG. 7A illustrates an embodiment of a reservoir 8 comprising a plunger end 310, a plunger shaft 12, a first electrical contact 314, a second electrical contact 316, a fill rod or conductive strip 320, and an insulator strip 370. In some embodiments, an electrical resistance is determined by detecting an electrical variable between a first electrical contact 314 through a conductive strip 320 and to a second electrical contact 316. In some embodiments, the electrical variable corresponds to or is used to determine a liquid level in the wearable drug delivery device 8. In some embodiments, at least one of the first electrical contact 314 and the second electrical contact 316 is a spring. The first electrical contact 314 and the second electrical contact 316 may both be springs or flexible conductive members that are able to bend out of the way when a conductive strip 320 is moved in between them, while still maintaining contact with conductive strip 320. In some embodiments, electrical contacts 314, 316 may be touching or directly electrically connected prior to a conductive strip 320 being moved in between them, such that in the initial state there is effectively zero resistance between electrical contacts 314, 316. In alternative embodiments, electrical contacts 314, 316 may not be touching or not directly electrically connected prior to a conductive strip 320 being moved in between them, such that in the initial state there is effectively infinite resistance between electrical contacts 314, 316.

In some embodiments, the conductive strip 320 is configured to slide past the first electrical contact 314 and the second electrical contact 316 while touching the first electrical contact 314 and the second electrical contact 316. As illustrated in FIG. 7B, the conductive strip 320 may be coupled to a plunger seal end 18. The conductive strip 320 may slide further out of the reservoir 8 as the plunger moves in the reservoir and liquid is added to the wearable drug delivery device 8. The conductive strip 320 may slide further into the reservoir 8 when liquid is expelled from the wearable drug delivery device 8. The conductive strip 320 may be coupled to a plunger seal end 18 (see e.g. FIG. 7B). In some embodiments the conductive strip 320 is bent in a "U" shape with an optional insulator strip 370 disposed in the interior or in the concave surface of conductive strip 320 so as to prevent the two sides of the conductive strip 320 from directly contacting each other at a position away from the "U" shaped end. In some embodiments the conductive strip 320 is bent in half with an insulator strip 370 disposed between a first half and a second half. The insulator strip 370 may prevent the inner surface of the first half of the conductive strip 320 from touching the inner surface of the second half of the conductive strip 320. The insulator strip 370 may keep the first half of the conductive strip 320 electrically isolated from the second half of the conductive strip 320. In some embodiments, the insulator strip 370 may simply be air. Except for at the fold at the U-shaped end, the sides of the conductive strip 320 are kept electrically isolated from each other, and resistance or other electrical properties between electrical contacts 314, 316 can be measured along this conductive strip 320. The resistance along the fill rod or conductive strip 320 may be measured at the open end of the folded strip by two stationary contacts, such as electrical contacts 314 and 316, each contacting an alternate side of the conductive strip 320.

As the fill rod moves between the electrical contacts 314, 316, the length of the conductive path, between the contacts, changes. This results in a continually changing resistance. The resistance can be correlated with the location of the pump plunger and the fill volume may be determined based on the location of the plunger. Since the volume of the reservoir would be known, the location of the plunger can be used to determine the volume of liquid drug in the reservoir.

Again, as the conductive strip 320 moves past the first electrical contact 314 and the second electrical contact 316, making contact with both of them, an electrical property, such as resistance, may be measured. In some embodiments, a processor will compare the determined electrical variable or resistance to a known threshold electrical variable or resistance. In some embodiments, when the determined variable or resistance exceeds a threshold variable or resistance, the reservoir may enter a startup or activate mode, or may cause a signal to be generated to output to a remote device data pertaining to the fill level of the reservoir. For example, when the determined variable or resistance is above or below a threshold variable or resistance, the reservoir may enter a startup or activate mode, and this threshold variable or resistance may correspond to a particular volume of drug inside the reservoir, such as 50 Units of liquid drug, for example. Other thresholds and corresponding volumes of liquid drug may be used, such as 1 Unit, 10 Units, 25 Units, 50 Units, 85 Units, 100 Units, 200 Units, or 300 Units for example. A lower value (such as 1 Unit) may correspond to a low resistance value and may indicate that liquid drug has just started to be inserted into the reservoir, and the conductive strip 320 has just started to make electrical contact with electrical contacts 314, 316. A higher value (such as 200 Units or 300 Units) may correspond to a high resistance value and may indicate that the reservoir is now completely full of liquid drug. Every variation in between is possible and, as explained above, different resistance values between electrical contacts 314, 316 may correspond to a precise location of the plunger inside the reservoir, and hence a precise volume of liquid drug inside the reservoir.

The sensor may be configured to calibrate itself. The sensor may calibrate to register a fully extended plunger (inside the reservoir) as an empty or baseline resistance value. In some embodiments, the determined resistance is compared to a lookup table with known resistance values corresponding to known fluid volumes for the wearable drug delivery device 8. The lookup table may be stored in memory on the wearable drug delivery device. In some embodiments, the determined resistance is used in an equation to calculate a fluid volume for the wearable drug delivery device 8. In some embodiments the resistance is correlated with the location of the plunger and the liquid level of the wearable drug delivery device 8. These determinations and these calculations can be made directly on the wearable medical device and output to a user device to indicate to the user whether the wearable medical device is activated or not and how much liquid drug is inside the reservoir of the wearable medical device. The position of the plunger and/or the amount of liquid drug inside the reservoir may be output to a user device on a cyclical basis (e.g., every 5 minutes), or any time the volume of liquid drug inside the reservoir changes, or any time the volume of liquid drug inside the reservoir changes by a threshold amount (e.g., 1 Unit). In this manner, the user may be continually informed of the state of the wearable medical device and how much liquid drug remains inside the reservoir.

Figure 8:
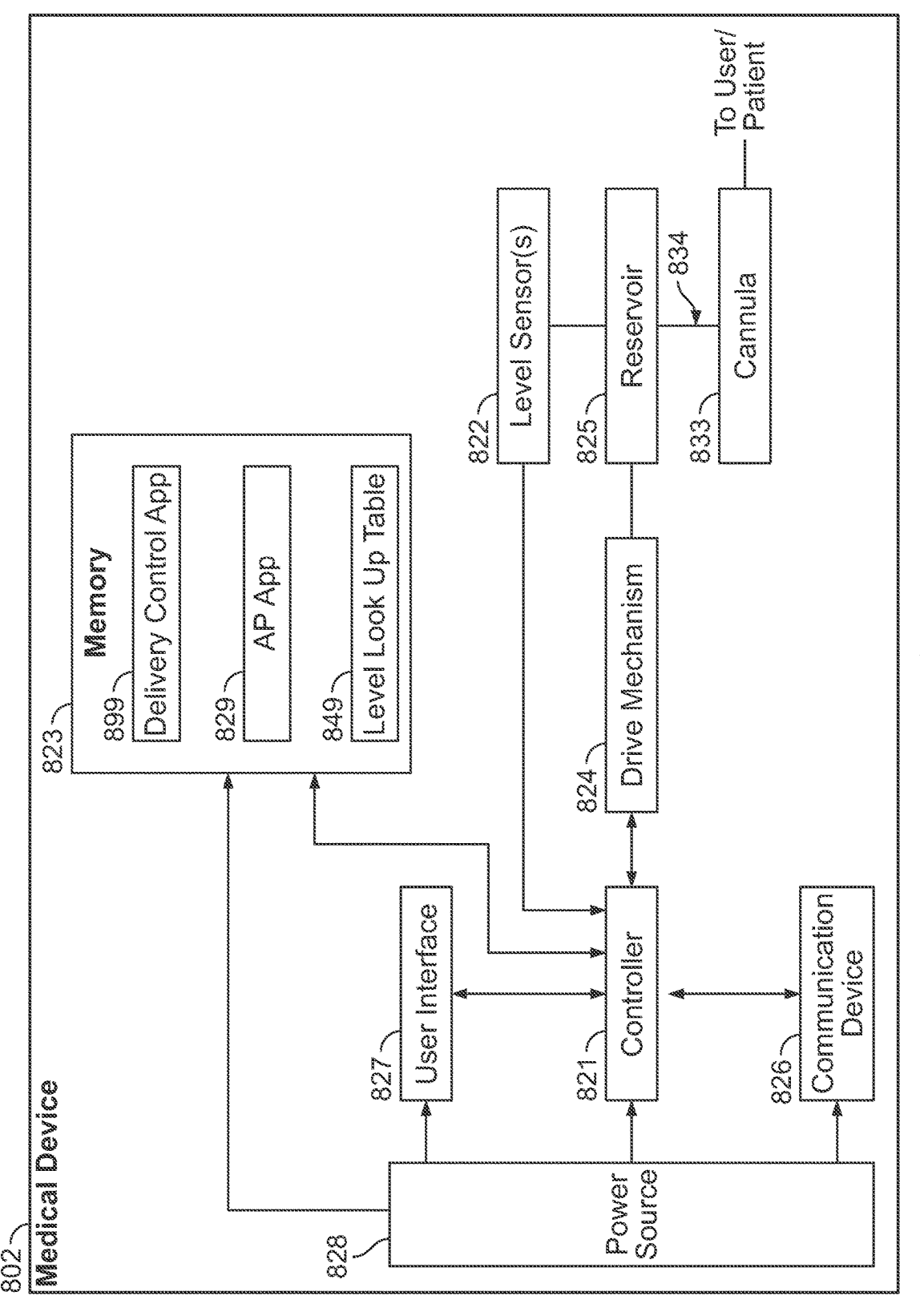
FIG. 8 illustrates a schematic diagram of a drug delivery system according to embodiments of the present disclosure.

FIG. 8 illustrates a simplified block diagram of an example drug delivery device. The drug delivery device system 800 may include a medical device 802, a controller 821, a memory 823, an AP application 829 and delivery control application 899 stored in the memory 823, a drive mechanism 824, a communication device 826, a level sensor(s) 822, a user interface 827, and a power source 828. The memory 823 may be operable to store programming code and applications including a delivery control application 899, the AP application 829 and data, and level look up table 849. The delivery control application 899 and the AP application 829 may optionally be stored on other devices. The level look up table 849 may include different electrical characteristics of level sensor(s) 822 that correspond to a specific level (i.e., volume of liquid drug, number of units of a liquid drug, decimal or fractional indication of level, such as 0.6 or ½, or the like) of liquid drug in the reservoir 825. The controller 821 may be operable to access the level look up table 849 and compare electrical characteristics received from the level sensor(s) 822 to the data in the level look up table 849 to determine or identify a level of liquid drug in the reservoir 825. Alternatively, the controller 821 may be operable to calculate (for example, by using logic or software or a combination of both which implements Ohm's law) a level of the liquid drug in the reservoir 825. The communication device 826 may be operable to, in response to commands from the controller 821, transmit the level of liquid drug in the reservoir 825 to an external device, such as a personal diabetes management device, for presentation to a user.

The AP application 829 may be operable to perform various functions related to open loop operations, such as determination of a total daily setting for a drug or combination of drugs, such as a total daily insulin setting or the like. In an example, the AP application 829 configured to provide automatic delivery of insulin, via the delivery control application 899, based on an analyte sensor input, such as signals received from an analyte sensor, such as a continuous blood glucose monitor, or the like. The delivery control application 899 may, for example, be operable to interpret or apply signals provided by the AP application 829 to the drive mechanism 824 and/or the user interface 827.

The controller 821 may be coupled to the drive mechanism 824 and the memory 823. The controller 821 may include logic circuits, a clock, a counter or timer as well as other processing circuitry, and be operable to execute programming code and the applications stored in the memory 823 including the delivery control application 899. A communication device 826 may be communicatively coupled to the controller 821 and may be operable to wirelessly communicate with an external device, such as a personal diabetes management device, a smart device such as a smartphone and/or a smartwatch, or the like.

The drive mechanism 824 may be operable to deliver a drug, like insulin, at a fixed or variable rate. For example, an AP application or AID algorithm executing on a personal diabetes management device or a smart phone may determine or be informed that a user's total daily insulin (e.g., bolus and/or basal deliveries) is 48 units per 24 hours, which may translate to an exemplary physiological basal dosage rate of 1 unit per hour (48/24/2 (assuming a 1:1 basal/bolus ratio)) that may be determined according to a diabetes treatment plan. Of course, the drive mechanism 824 may be operable to deliver insulin at rates different from the example physiological dosage rate of 8 unit per hour. In an example, the system 800 may be attached to the body of a user, such as a patient or diabetic via, for example, by an adhesive, (e.g., directly attached to the skin of the user) and may deliver any therapeutic agent, including any drug or medicine, such as insulin, morphine, or the like, to the user. In an example, a surface of the system 800 may include an adhesive (not shown) to facilitate attachment to a user. The system 800 may, for example, be worn on a belt or in a pocket of the user and the liquid drug may be delivered to the user via tubing to an infusion site on the user.

In various examples, the system 800 may be an automatic, wearable drug delivery device. For example, the system 800 may include a reservoir 825 configured to hold a liquid drug (such as insulin), a needle and/or cannula 833 for delivering the drug into the body of the user (which may be done subcutaneously, intraperitoneally, or intravenously), and a drive mechanism 824, or other drive mechanism, for transferring the drug from the reservoir 825, through a needle or cannula 833, and into the user.

The drive mechanism 824 may be fluidly coupled to reservoir 825, and communicatively coupled to the medical device controller 821. The drive mechanism 824 may be coupled to the reservoir 825 and operable to output the liquid drug from the reservoir 825 via a fluid delivery path and out of the cannula 833. The drive mechanism 824 may have mechanical parameters and specifications, such as a pump resolution, which indicate mechanical capabilities of the drive mechanism. The drive mechanism 824 may also have electrical connections to control circuitry (not shown) that is operable to control operation of the drive mechanism 824. The pump resolution is a fixed amount of insulin the drive mechanism 824 delivers in a drive mechanism pulse, which is an actuation of the drive mechanism for a preset time period. Actuation may be when power from the power source 828 is applied to the control circuitry coupled to the drive mechanism 824 and the drive mechanism 824 operates to pump a fixed amount of insulin in a preset amount of time from the reservoir 825. Alternatively, the drive mechanism 824 may be substantially mechanical in structure and operation and utilize mechanical energy storage devices, such as springs or other biasing members to operate the drive mechanism 824. A level sensor(s) 822 may be coupled to elements of the reservoir 825, such as described with reference to FIGS. 1-7, or the like. The level sensor(s) 122 may be a circuit that either has a high potential or ground potential, or other electrical characteristic that is monitored by the controller 821.

The cannula 833 of FIG. 8 may be coupled to the reservoir 825 via a fluid delivery path 834. The cannula 833 may be operable to output the liquid drug to a user when the cannula 833 is inserted in the user.

The system 800 may also include a power source 828, such as a battery, a supercapacitor, a piezoelectric device, or the like, that is operable to supply electrical power to the drive mechanism 824 and/or other components (such as the controller 821, memory 823, and the communication device 826) of the system 800.

The controller 821 may be implemented in hardware, software, or any combination thereof. In various examples, the controller 821 can be implemented as dedicated hardware (e.g., as an application specific integrated circuit (ASIC)). The controller 821 may be a constituent part of the system 800, can be implemented in software as a computational model, or can be implemented external to the system 800 (i.e., remotely). The controller 821 may be configured to communicate with one or more other sensors (not shown).

A reservoir 825, may be included in a drug delivery device to store a liquid drug (e.g., insulin). For example, the reservoir 825 may be filled, or partially filled, with a liquid drug or a liquid drug solution. In one example, a liquid drug solution is a mixture of the liquid drug and added preservatives. The reservoir may store the liquid drug until all of the liquid drug has been dispensed (e.g., into a patient via a cannula). As such, the liquid drug (or solution) may remain in the reservoir for a period of time (e.g., 1 day, 3 days, 1 week, 2 weeks, etc.).

The medical device 802 may be a wearable drug delivery device that is worn on the body of the user. For example, an adhesive may couple the medical device 802 to the skin of a user's body. The medical device 802 may be a multi-part device. For example, the medical device 802 as a wearable drug delivery device may have a first part and a second part that couple or connect together. The first part and/or second part may fit into or slide into a tray or cradle that is adhered to the user's body, and the first part and/or second part may be removable from the tray. If using a first part and a second part, the first part may comprise reusable components (e.g., electronic circuitry, processor, memory, a drive mechanism, and potentially a rechargeable battery), and the second part may comprise disposable components (e.g., a reservoir, a needle and/or cannula, a disposable battery, and other portions or components that come into contact with the liquid drug or medicament). Moreover, the first part and the second part may contain their own housing or may combine together to form a single housing. The wearable drug delivery device 802 may be directly coupled to a user (e.g., directly attached to a body part and/or skin of the user via an adhesive, directly, via the tray, or the like). In an example, a surface of the wearable drug delivery device 802 or a tray into which the wearable drug delivery device 802 couples may include an adhesive to facilitate attachment to the skin of a user.

While the medical device 802 is described with reference to delivery of insulin and the use of an AID algorithm, the medical device 802 may be operable to implement a drug delivery regimen via a medication delivery algorithm using a number of different liquid or therapeutic drugs. A liquid drug may be or include any drug in liquid form capable of being administered by a drug delivery device via a subcutaneous cannula, including, for example, insulin, glucagon-like peptide-1 (GLP-1), pramlintide, glucagon, co-formulations of two or more of GLP-1, pramlintide, and insulin; as well as pain relief drugs, such as opioids or narcotics (e.g., morphine, or the like), methadone, arthritis drugs, hormones, such as estrogen and testosterone, blood pressure medicines, chemotherapy drugs, fertility drugs, or the like.

Figure 9A:
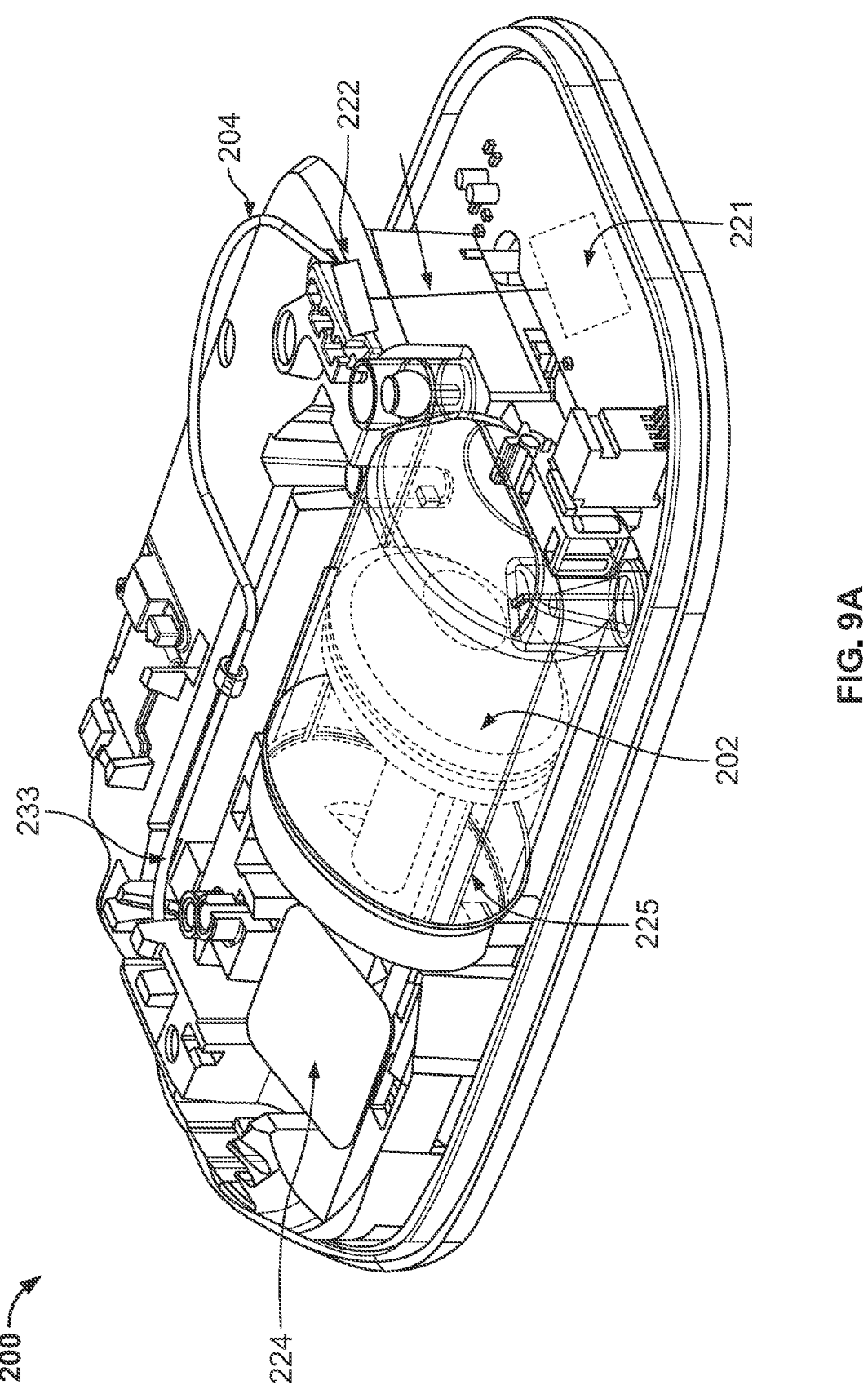
FIG. 9A illustrates a perspective view of a drug delivery system according to embodiments of the present disclosure.

As shown in FIG. 9A, the system 200 may include a plunger 202 positioned within the reservoir 225. An end portion or stem of the plunger 202 can extend outside of the reservoir 225. The pump mechanism 224 may, under control of the controller 221, be operable to cause the plunger 202 to expel the fluid, such as a liquid drug (not shown) from the reservoir 225 and into a fluid component 204 and cannula 233 by advancing into the reservoir 225. In various examples, a pressure sensor, such as that shown at 222, may be integrated anywhere along the overall fluid delivery path of the system 200, which includes the reservoir 225, the fluid delivery path component 204, and the cannula 233.

The controller 221 may be implemented in hardware, software, or any combination thereof. In various examples, the controller 221 can be implemented as dedicated hardware (e.g., as an application specific integrated circuit (ASIC)). The controller 221 may be a constituent part of the system 200, can be implemented in software as a computational model, or can be implemented external to the system 200 (e.g., remotely). The controller 221 may be configured to communicate with one or more sensors, such as level sensor(s) 822 of FIG. 8.

As described above, a reservoir, such as 225, may be included in a drug delivery device to store a liquid drug (e.g., insulin). For example, the reservoir 225 may be filled, or partially filled, with a liquid drug or a liquid drug solution. In one example, a liquid drug solution is a mixture of the liquid drug and added preservatives. The reservoir may store the liquid drug until all of the liquid drug has been dispensed (e.g., into a patient via a cannula). As such, the liquid drug (or solution) may remain in the reservoir for a period of time (e.g., 1 day, 3 days, 1 week, 2 weeks, etc.).

Figure 9B:
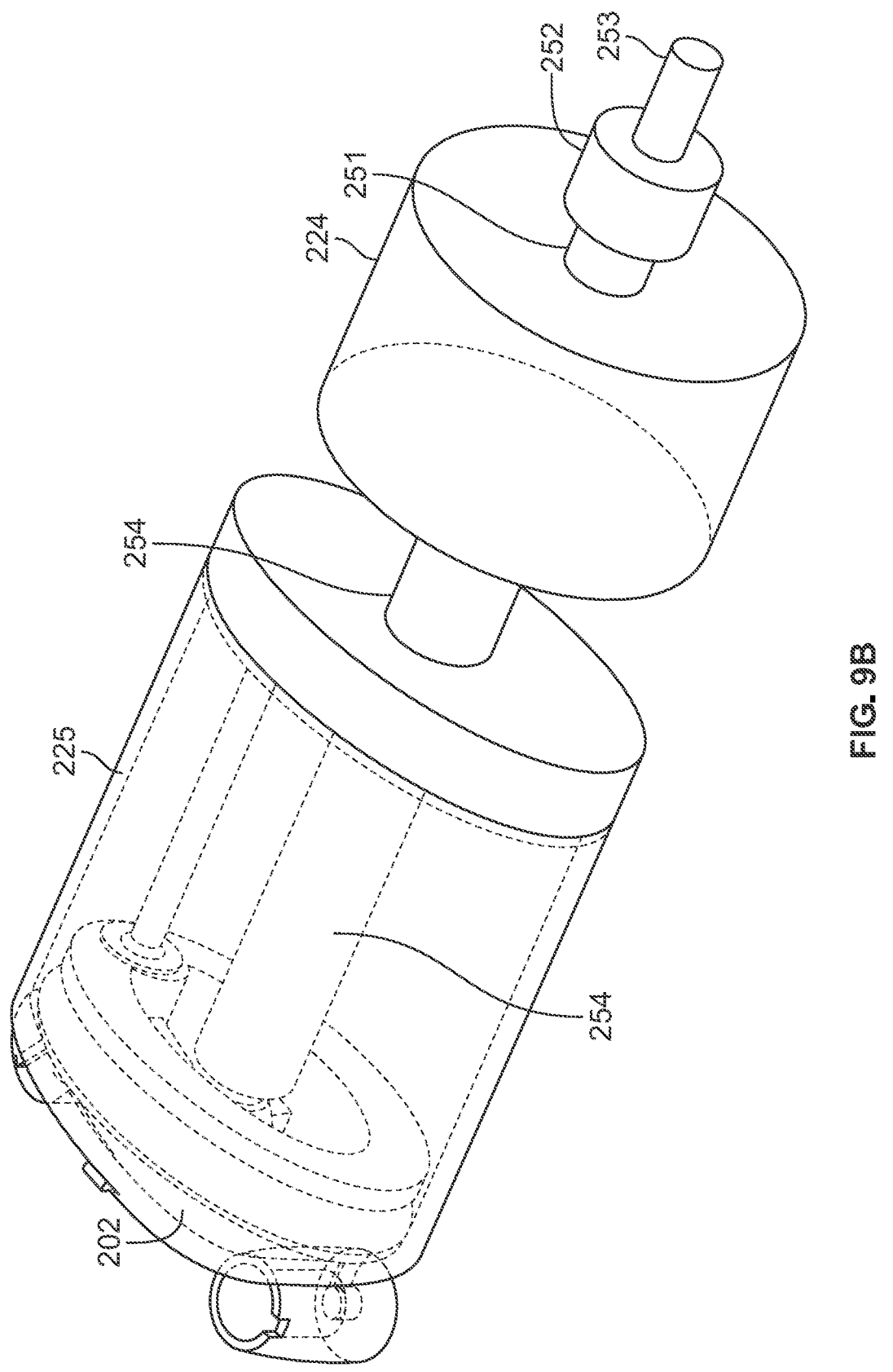
FIG. 9B illustrates a detailed perspective view of a portion of an example of a drug delivery system of FIG. 9A according to embodiments of the present disclosure.
Figure 9C:
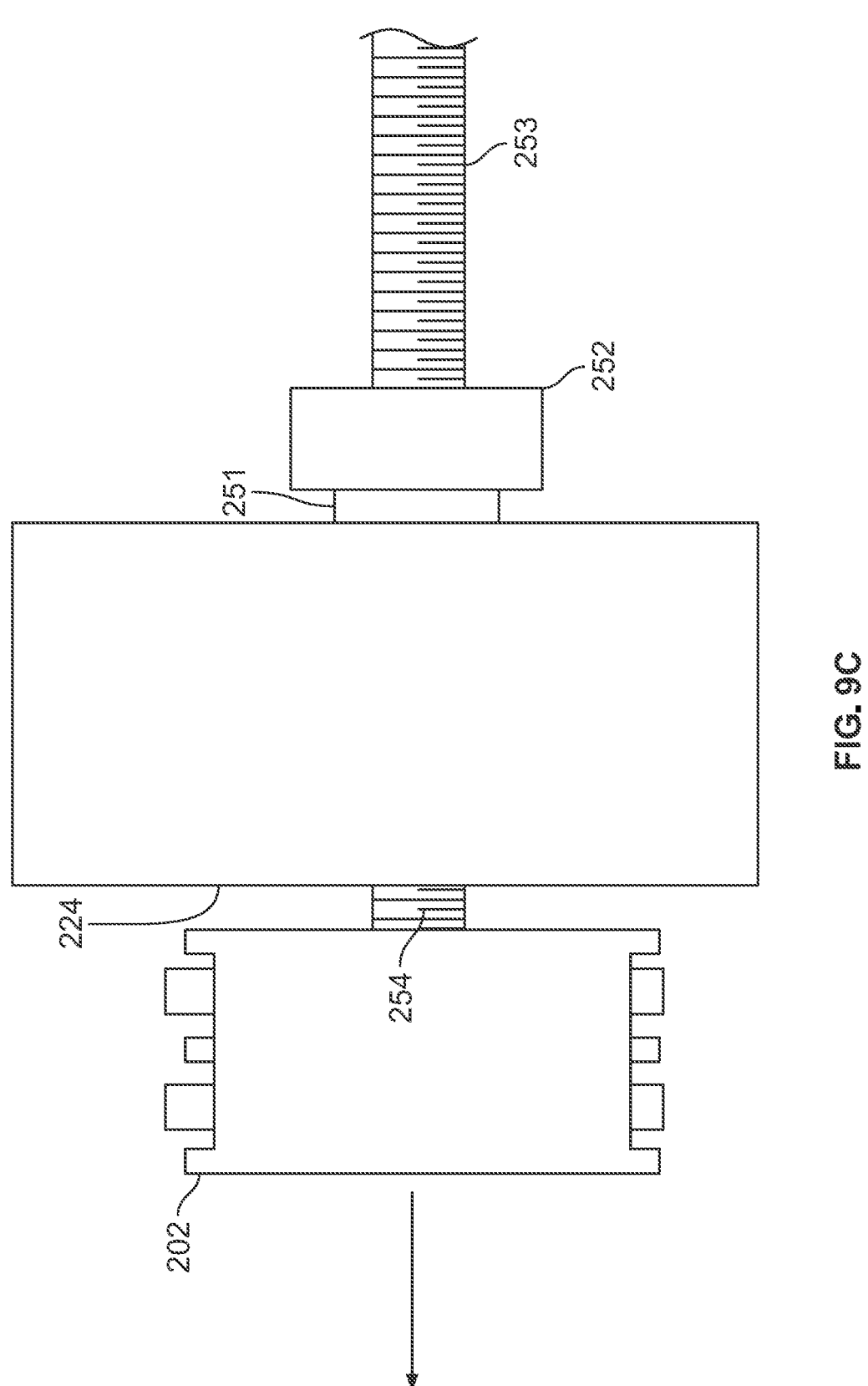
FIG. 9C illustrates a top view of an example of a drive mechanism of a drug delivery system of FIG. 9A according to embodiments of the present disclosure.

FIG. 9B illustrates an example of a reservoir coupled to the drive mechanism 224 in more detail than the view of FIG. 9A. Likewise, FIG. 9C illustrates a perspective view of the drive mechanism 250. As disclosed in later examples, the drive mechanism 224 (shown in more detail in later examples) may include co-axial ratchet wheels, drive arms, sensor contacts and an actuator. The co-axial ratchet wheels may be coupled to a plunger 202 via an elongated shaft 254. At a high level, the ratchet wheels of the drive mechanism 224 are engaged by the drive arms in response to a force applied by the actuator to incrementally advance the plunger 202 and the elongated shaft 254 into the reservoir 225. The elongated shaft 245 advances the plunger 202 to dispense the liquid drug out of the reservoir 225. In one example, a drive mechanism coupling 251 is operable to rotate a drive element 252 in response to forces applied to either the first ratchet wheel or the second ratchet wheel of the drive mechanism 224. The drive element 252 may include (or may be otherwise coupled to) a lead screw 253 that is coupled to the plunger 202 (e.g., via the elongated shaft 254). The drive element 252 is operable to rotate causing the lead screw 253 to advance the elongated shaft 254 and the plunger 202 within the reservoir 225 to expel the liquid drug from reservoir 225.

Figure 10:
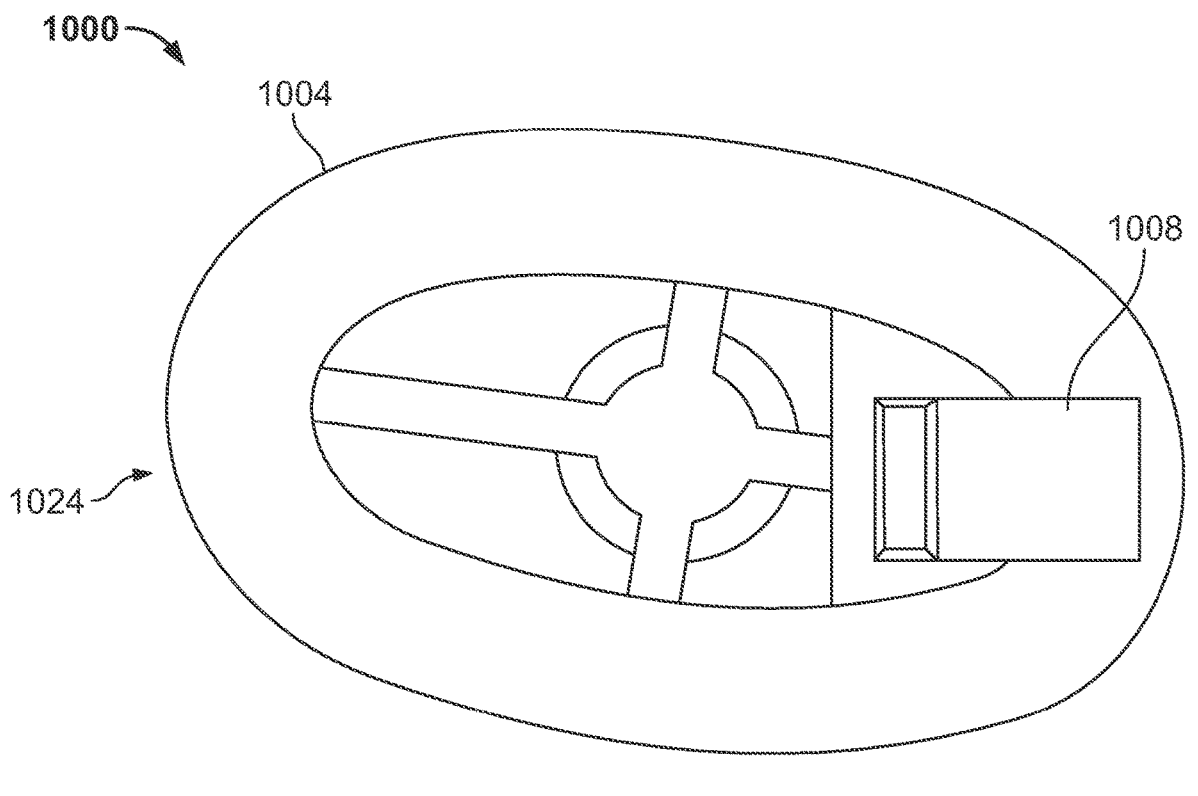
FIG. 10 illustrates an exemplary embodiment of a system for a fluid gauge of a wearable medical device.

Referring now to FIG. 10, a system 1000 for a fluid gauge of a wearable medical device is shown. System 1000 may include plunger end 1004. The plunger end 1004 may be as described above with reference to FIG. 5C. In some embodiments, the plunger end 1004 may be made from a sheet metal, such as, but not limited to, copper, aluminum, steel, and the like. The plunger end 1004 may be shaped circular, ovular, rectangular, and/or other shapes, without limitation. In some embodiments, the plunger end 1004 may have a length of about 1.5 inches. In some embodiments, the plunger end 1004 may have a length of about 0.6 inches to about 0.7 inches. In other embodiments, the plunger end 1004 may have a length greater than or less than about 1.5 inches. The plunger end 1004 may have a thickness of about 2 mm, in some embodiments. In other embodiments, the plunger end 1004 may have a thickness of greater than or less than about 2 mm, without limitation.

The plunger end 1004 may have markings 1024. The markings 1024 may be configured to connect to one or more components of a wearable medical device, such as a plunger, rod, lock, and/or other component. The markings 1024 may be about 0.5 mm deep into a surface of the plunger end 1004. In other embodiments, the markings 1024 may be greater than or less than about 0.5 mm deep into a width of the plunger end 1004. The markings 1024 may be shaped as, without limitation, a cross, circle, square, rectangle, and/or other shape. In some embodiments, the markings 1024 may be a combination of shapes. As a non-limiting example, the markings 1024 may include a cross indented into the plunger end 1004 and a circle having four arcs intersecting the cross. In some embodiments, the markings 1024 may include a combination of raised and indented structures. For instance, the markings 1024 may include an indented cross having a circular middle portion and four raised arcs, each arc connecting two lines of the cross.

Still referring to FIG. 10, the plunger end 1004 may include tab 1008. The tab 1008 may be an indented structure located at a side of the plunger end 1004. For instance, and without limitation, the tab 1008 may be located at a top, bottom, left, or right side of the plunger end 1004. The tab 1008 may be machined or welded into the plunger end 1004. In some embodiments, the tab 1008 may be ultrasonically machined to the plunger end 1004. The tab 1008 may be configured to connect to or otherwise couple with one or more rods. For instance, the tab 1008 may be configured to connect with rod 1012. The rod 1012 may be made from, without limitation, steel, aluminum, copper, and the like. The rod 1012 may have a thickness of about 0.5 mm, greater than about 0.5 mm, or less than about 0.5 mm, without limitation. In some embodiments, the rod 1012 may be about 4 cm long, greater than 4 cm long, or less than 4 cm long, without limitation. In some embodiments, the rod 1012 may have a length of about 2 mm. In some embodiments, the rod 1012 may be tapered. A tapering of the rod 1012 may cause an uneven distribution of weight of the rod 1012. For instance, and without limitation, a left side of the rod 1012 may be lighter and/or smaller than a right side of the rod 1012, which may be heavier, or vice versa. A tapering of the rod 1012 may cause the rod 1012 to become increasingly wider/taller from a left side of the rod 1012 to a right side of the rod 1012, or vice versa.

In some embodiments, the rod 1012 may include one or more bends. In some embodiments, the rod 1012 may include first bend 1028 and/or second bend 1032. The first bend 1028 may be located at an end of the rod 1012, such as, without limitation, a left or right end of the rod 1012. In some embodiments, the first bend 1028 may bend a portion of the rod 1012 at an angle. Angles of the first bend 1028 may include about 15 to 90 degrees, without limitation. In some embodiments, angles of the first bend 1028 may be greater than 90 degrees or less than 15 degrees, without limitation. The rod 1012 may have second bend 1032 which may be located adjacent to the first bend 1028. In some embodiments the second bend 1032 may have an angle opposite the first bend 1028. For instance, the first bend 1028 may have an angle of 90 degrees and the second bend 1032 may have an angle of −90 degrees with respect to an x-axis. The first bend 1028 and the second bend 1032 may form a "Z" like shape. The first bend 1028 may be located about 3 mm from a right end of the rod 1012, greater than about 3 mm from a right end of the rod 1012, or less than about 3 mm from a right end of the rod 1012, without limitation. The second bend 1032 may be located at an end of the first bend 1028. For instance, the second bend 1032 may be located about 2 mm from the first bend 1028, greater than about 2 mm, or less than about 2 mm, without limitation.

The first bend 1028 and the second bend 1032 may offset a positioning of the rod 1012 relative to the plunger end 1004. For instance, the first bend 1028 and the second bend 1032 may allow the rod 1012 to be offset by about 4 mm from a center of the plunger end 1004. In other embodiments, the first bend 1028 and the second bend 1032 may allow for an offset of the rod 1012 of greater than or less than about 4 mm from a center portion of the plunger end 1004. By offsetting the rod 1012 from a central position of the plunger end 1004, the first bend 1028 and the second bend 1032 may allow the rod 1012 to avoid other components of a wearable medical device, such as, but not limited to O-ring glands, reservoirs, and the like.

The rod 1012 may be configured to interact with first spring 1016 and/or second spring 1020. In some embodiments, the rod 1012 may be configured to interact with both the first spring 1016 and the second spring 1020. The first spring 1016 and the second spring 1020 may be made of any suitable material, such as, but not limed to, copper, aluminum, steel, and the like. In some embodiments, the first spring 1016 and the second spring 1020 may be positioned at a side of the rod 1012, such as a right side of the rod 1012 next to the second bend 1032. In other embodiments, the first spring 1016 and the second spring 1020 may be positioned at various lengths and/or sides of the rod 1012, such as, but not limited to, centrally of the rod 1012, a left side of the rod 1012, and the like. In some embodiments, the first spring 1016 may be positioned about 2 mm from the second spring 1020. In other embodiments, the first spring 1016 may be positioned greater than or less than about 2 mm from the second spring 1020. The first spring 1016 may have a length of about 5 mm, greater than 5 mm, or less than 5 mm, without limitation. The second spring 1020 may have a length different from that of the first spring 1016. In other embodiments, the first spring 1016 and the second spring 1020 have a same length.

Figure 11:
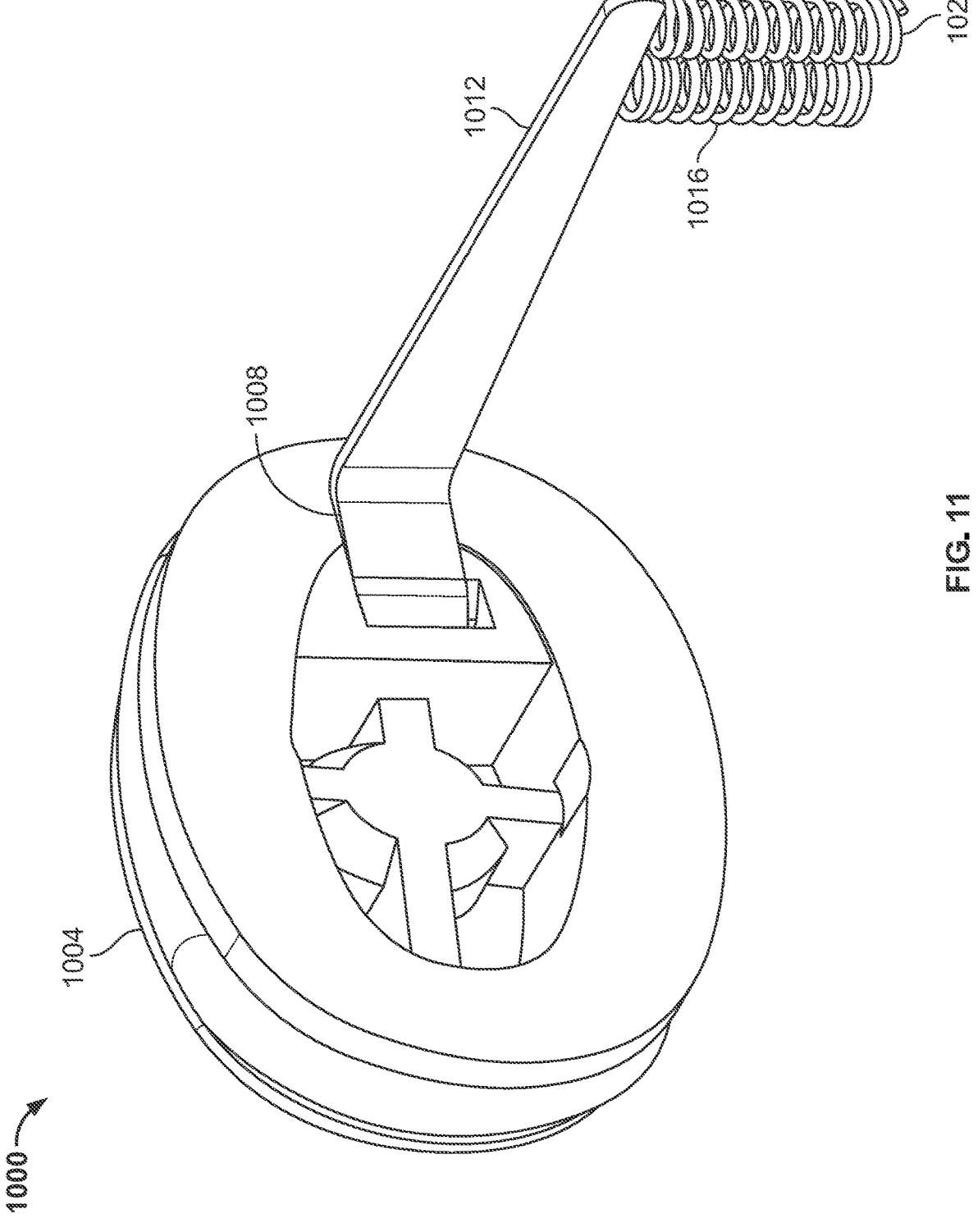
FIG. 11 illustrates a perspective view of the system shown in FIG. 10.

Referring now to FIG. 11, a perspective view of the system 1000 of FIG. 10 is shown. The rod 1012, first spring 1016, second spring 1020, plunger end 1004, and tab 1008 may be as described above with reference to FIG. 10. The tab 1008 may hold and/or secure one or more bent ends of the rod 1012. For instance, the first bend 1028 and/or the second bend 1032 as described above with reference to FIG. 10. The tab 1008 may be located at a top, left, right, or bottom position of the plunger end 1004. The rod 1012 may be positioned at a top, bottom, left, or right position of the plunger end 1004, connected by the tab 1008. The first spring 1016 and/or the second spring 1020 may be positioned at a distal end of the rod 1012. For instance, the first spring 1016 and/or the second spring 1020 may be positioned at a point of the rod 1012 farthest from the plunger end 1004. In some embodiments, three or more springs may be used and/or connected to the rod 1012.

Figures 12A, 12B, 12C:
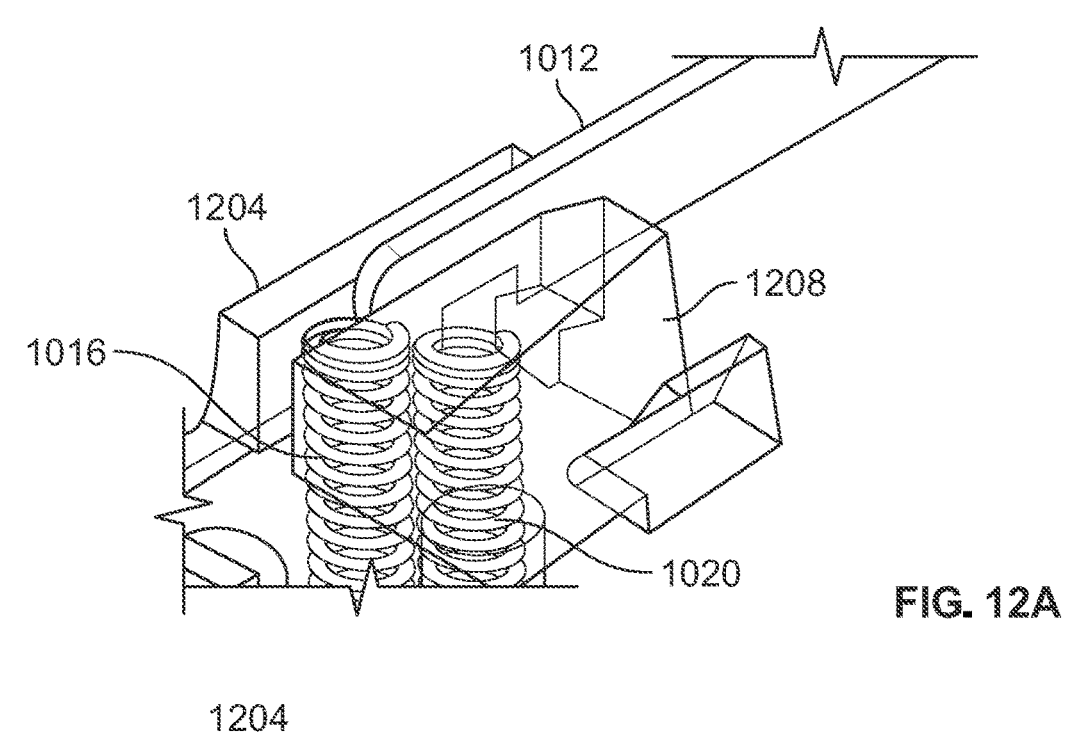
FIGS. 12A-C illustrate various view of the system of FIG. 10.

Referring now to FIG. 12A, a side view of the rod 1012, first spring 1016, and second spring 1020 in channels 1204 and 1208 is shown. The rod 1012, first spring 1016, and second spring 1020 may be as described above with reference to FIG. 10. The rod 1012 may be configured to enter between the first channel 1204 and the second channel 1208. The first channel 1204 and the second channel 1208 may form a pocket, which the rod 1012 may pass through. The first channel 1204 and/or the second channel 1208 may be made from, without limitation, plastic, rubber, and the like. In some embodiments, the first channel 1204 and/or the second channel 1208 may have a thickness of about, without limitation, 4 mm, greater than 4 mm, less than 4 mm, and the like. A pocket formed by the first channel 1204 and the second channel 1208 may be about 3 mm wide, greater than 3 mm wide, or less than 3 mm wide, without limitation.

The first spring 1016 and/or the second spring 1020 may be positioned within a pocket between the first channel 1204 and the second channel 1208. The first spring 1016 may be placed adjacent to the second spring 1020. In some embodiments, the first spring 1060 and the second spring 1020 may be located at an end of a pocket formed by the first channel 1204 and the second channel 1208. For instance, and without limitation, the first spring 1016 and/or the second spring 1020 may be located at a left, right, or other end of a pocket formed by the first channel 1204 and the second channel 1208. The first spring 1016 and/or the second spring 1020 may be configured to compress from contact with the rod 1012. The first spring 1016 and/or the second spring 1020 may compress about, without limitation, 2 mm, greater than 2 mm, or less than 2 mm. The first spring 1016 and/or the second spring 1012 may have a spring constant of about, without limitation 5 N/M, greater than 5 N/M, or less than 5 N/M, without limitation.

In some embodiments, the first spring 1016 and/or the second spring 1020 may be conductive. For instance, the first spring 1016 and/or the second spring 1020 may have a conductivity of about $5.96 \times 107\ \sigma$ (S/m), without limitation. The rod 1012 may be conductive and configured to provide an electrical connection between the first spring 1016 and the second spring 1020. In some embodiments, the first spring 1016 may have a positive voltage supply and the second spring 1020 may act as a ground, or vice versa. The first spring 1016 and/or the second spring 1020 may be connected to a sensing element, such as any sensing element and/or sensor as described throughout this disclosure, without limitation. Sensing elements may include, without limitation, voltmeter, potentiometers, ohmmeters, ammeters, and the like. In some embodiments, a compression of first spring 1016 and/or second spring 1020 may change a resistivity of the first spring 1016 and/or the second spring 1020. For instance, and without limitation, the second spring 1020 may act as a potentiometer, with a changing voltage due to changing compressions. A compression of the first spring 1016 and/or the second spring 1020 may decrease a resistance of the first spring 1016 and/or the second spring 1020, which may increase a voltage and/or current of either or both of the first spring 1016 and the second spring 1020. A change in resistivity may correspond to a change in voltage and/or current of the first spring 1016 and/or the second spring 1020. A sensing element may be electrically connected to the first spring 1016 and/or the second spring 1020. A sensing element may be configured to receive voltage and/or current values of the first spring 1016 and/or the second spring 1020 and determine a change in contact pressure of the rod 1012 and/or a change of an amount of a liquid drug dispensed. A change in contact pressure of the rod 1012 may correspond to a change an amount of a liquid drug dispensed by a plunger connected to the plunger end 1004. In some embodiments, as a plunger dispenses a liquid drug, the rod 1012 may move in a forward direction along with the plunger. The rod 1012 may be connected to the plunger and may increase a contact pressure of the first spring 1016 and/or the second spring 1020 as a liquid drug is expelled from a reservoir. A sensing element may be configured to determine an amount of liquid drug dispensed based on changes in voltage and/or current of the first spring 1016 and/or the second spring 1020. As a non-limiting example, a change of a voltage of 50 mV may correspond to 1 mL of liquid drug expelled from a reservoir. A sensing element and/or processor of a wearable medical device may be configured to determine an amount of liquid drug remaining in a reservoir based on a change in voltage and/or current of the first spring 1016 and/or the second spring 1020. For instance, and without limitation, a sensing element and/or processor may determine that a voltage of 1.8 V across the second spring 1020 corresponds to 5 mL remaining in a reservoir of a wearable medical device.

Still referring to FIG. 12A, in some embodiments, the rod 1012 may be electrically charged at an initial stage of drug delivery. The rod 1012, as a plunger is moved, may increase contact with the first spring 1016 and/or the second spring 1020, which may cause a change in voltage and/or current at the first spring 1016 and/or the second spring 1020. A sensing element may be configured to determine an amount of liquid drug dispensed based on a change in voltage and/or current of the first spring 1016 and/or the second spring 1020. In some embodiments, the rod 1012 may be electrically charged and may contact the first spring 1016 and/or the second spring 1020.

A sensing element and/or processor may determine a wakeup mode for a wearable medical device based on a contact of the electrically charged rod 1012 with the first spring 1016 and/or the second spring 1020. A sensing element may determine a wakeup mode for a wearable medical device based on changes in voltage and/or current of the first spring 1016 and/or the second spring 1020 with a non-electrically charged rod 1012, such as described above, without limitation. In some embodiments, the rod 1012 may initially be positioned away from the first spring 1016 and/or the second spring 1020. The rod 1012 may contact the first spring 1016 and/or the second spring 1020, which may be sensed by a sensing element connected to the first spring 1016 and/or the second spring 1020. A sensing element and/or processor of a wearable medical device may cause the wearable medical device to enter a wakeup mode. A wakeup mode may include an initialization or startup of a wearable medical device. A sensing element may communicate data sensed to a processor of a wearable medical device which may initiate a wakeup mode of the wearable medical device.

Referring now to FIG. 12B, a top view of the rod 1012 in a pocket is illustrated. The rod 1012, first spring 1016, second spring 1020, first channel 1204, and second channel 1208 may be as described above with reference to FIG. 12A. The rod 1012 may enter through a pocket formed by the first channel 1204 and the second channel 1208, which may cause a compression of the first spring 1016 and/or the second spring 1020.

Referring now to FIG. 12C, a side view of the rod 1012 entering a pocket is shown. The rod 1012, first spring 1016, second spring 1020, first channel 1204, and second channel 1208 may be as described above with reference to FIG. 12A. The second spring 1020 may be compressed by the rod 1012 while the first spring 1016 may be uncompressed due to the rod 1012 not reaching the first spring 1016 within a pocket formed by the first channel 1204 and the second channel 1208. In some embodiments, both the first spring 1016 and the second spring 1020 may be compressed by the rod 1012.

Figure 13:
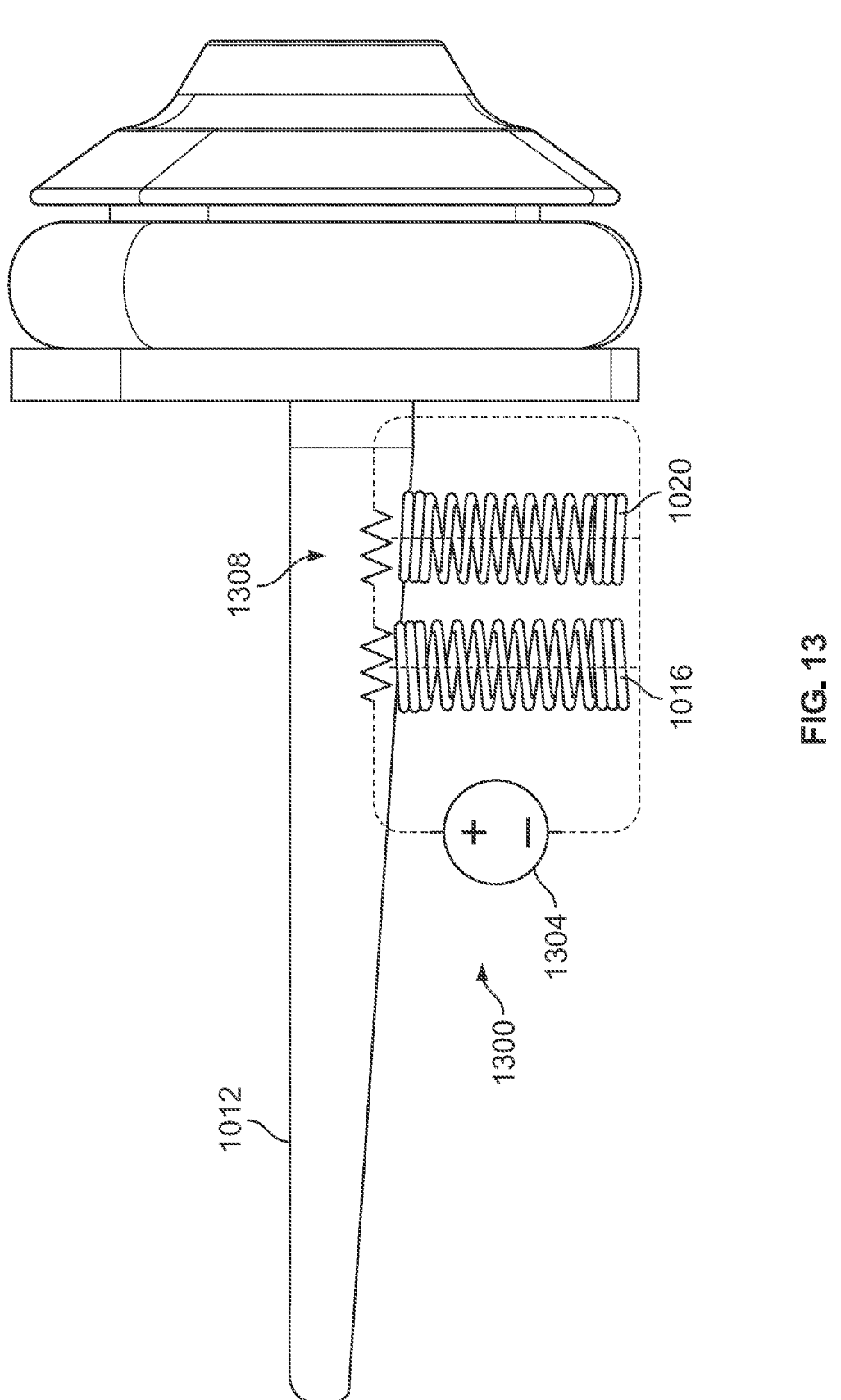
FIG. 13 illustrates a circuit schematic overlayed with the system of FIG. 10.

FIG. 13 shows an illustration of a circuit schematic 1300 overlayed with the system of FIG. 10. The circuit 1300 may include voltage source 1304. The voltage source 1304 may be provided by a battery or other electric power source of a wearable medical device. In some embodiments, the first spring 1016 may be directly connected to the voltage source 1304. In some embodiments, the voltage source 1304 may include a voltage of about 4.5 V. In other embodiments, the voltage source 1304 may be greater than or less than about 4.5 V, without limitation. The first spring 1016 may act as the voltage source 1304, in some embodiments, The second spring 1020 may act as a potentiometer 1308. For instance, a resistance of the second spring 1020 may decrease when the second spring 1020 is compressed and may increase when the second spring 1020 is decompressed. The rod 1012 may act as a circuit wire/line. The rod 1012 may connect the first spring 1016 to the second spring 1020. For instance, in an initial stage, the rod 1012 may not initially may contact between the first spring 1016 and the second spring 1020 and may contact with the first spring 1016 and the second spring 1020 upon a movement of a plunger connected to the rod 1012. The rod 1012 may be tapered. A tapering of the rod 1012 may allow for increased contact pressure on the second spring 1020 as the rod 1012 moves with a plunger due to a heavier distribution of weight on a side of the rod 1012. In some embodiments, a tapering of the rod 1012 may allow for increased contact pressure on the second spring 1020 due to an increased displacement of the second spring 1020. A sensing element (not shown) may be connected to the circuit 1300 and/or a processor of a wearable medical device. A sensing element may be configured to detect changes in voltages across the second spring 1020 and determine one or more parameters such as, but not limited to, amount of liquid drug dispensed, amount of liquid drug remaining, and the like. In some embodiments, the second spring 1020 may act as the voltage source 1304 and the first spring 1016 may act as the potentiometer 1308.

Figure 14:
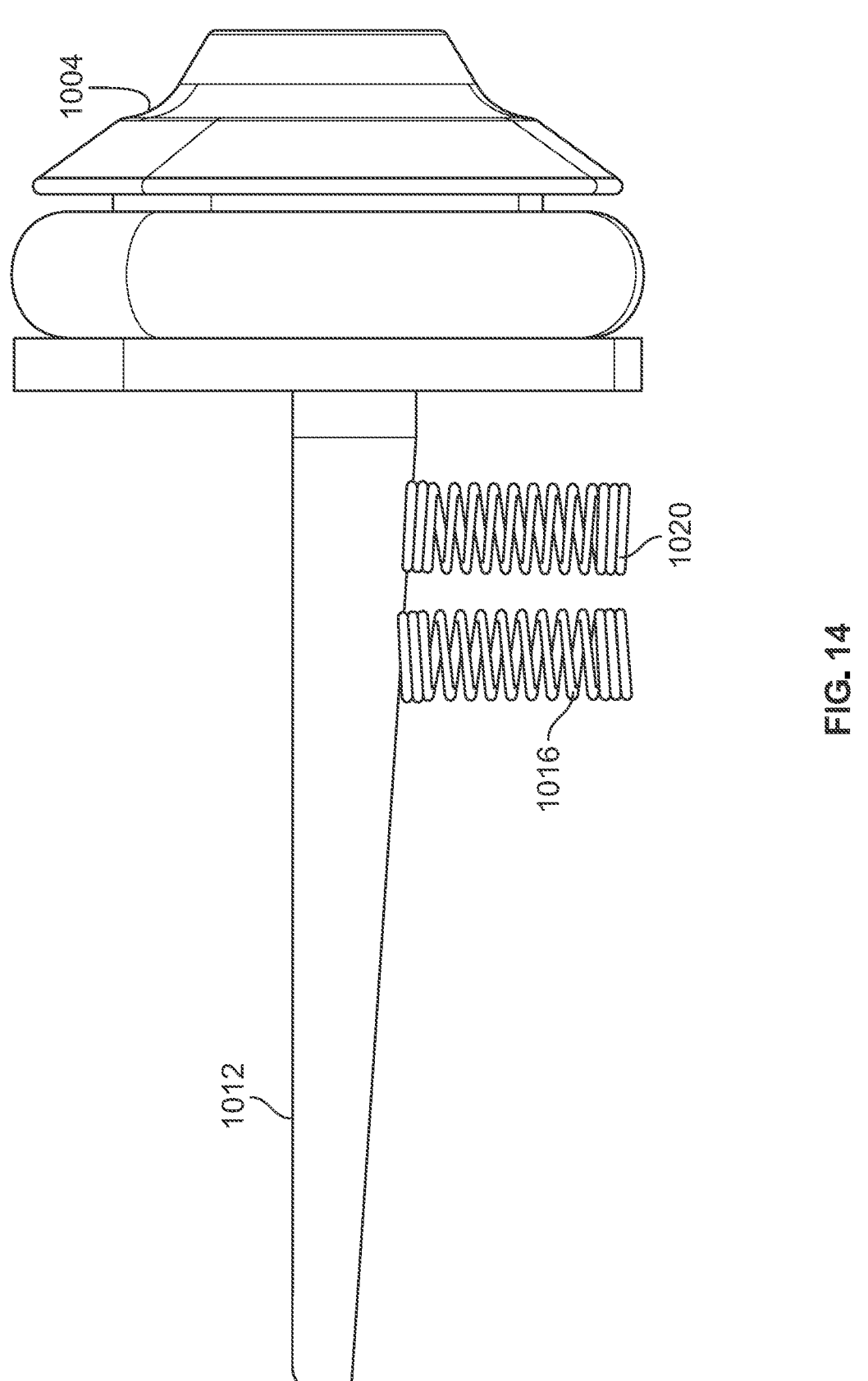
FIG. 14 illustrates a side view of the system of FIG. 10.

FIG. 14 illustrates a left side view of the system of FIG. 10. The plunger end 1004, rod 1012, first spring 1016, and second spring 1020 may be as described above with reference to FIG. 10. The first spring 1016 and/or the second spring 1020 may be positioned closer to the plunger end 1004. In some embodiments, the first spring 1016 and/or the second spring 1020 may be positioned at a base of the rod 1012 which may be larger than a distal end of the rod 1012 due to a tapering of the rod 1012. As a non-limiting example, the first spring 1016 and/or the second spring 1020 may be positioned beneath a large base of a tapering of the rod 1012, which may be adjacent to the plunger end 1004.

Figure 15:
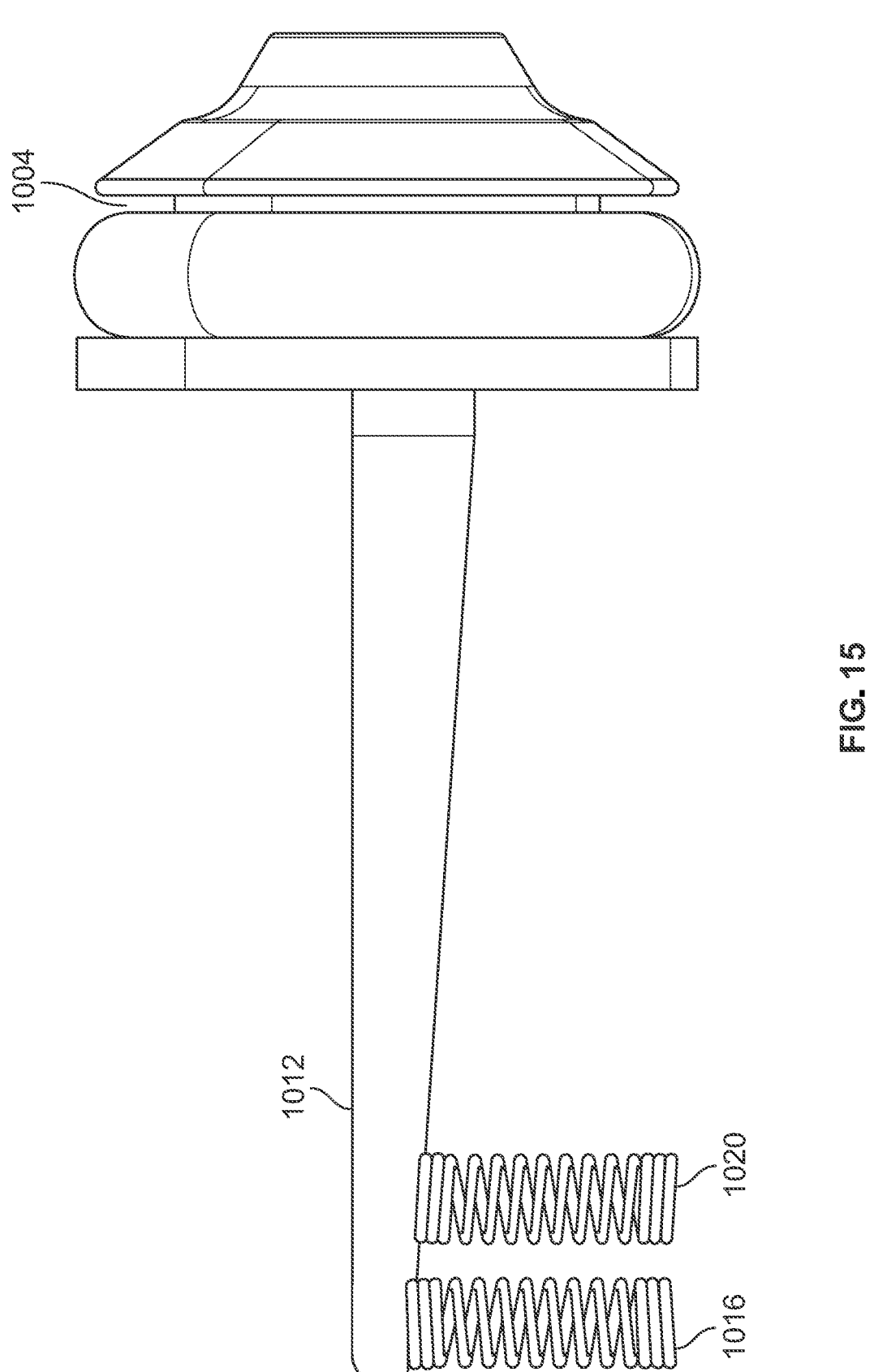
FIG. 15 illustrates another side view of an embodiment of a system for a fluid gauge of a wearable medical device.

FIG. 15 illustrates another exemplary embodiment of the system of FIG. 10. The plunger end 1004, rod 1012, first spring 1016, and second spring 1020 may be as described above with reference to FIG. 10. The first spring 1016 and/or the second spring 1020 may be positioned at a distal end of the rod 1012. For instance, the rod 1012 may be tapered and the first spring 1016 and/or the second spring 1020 may be positioned at a smaller left end of a tapering of the rod 1012 relative to a larger based end on a right of the rod 1012. The first spring 1016 and/or the second spring 1020 may be positioned away from the plunger end 1004.

Figure 16:
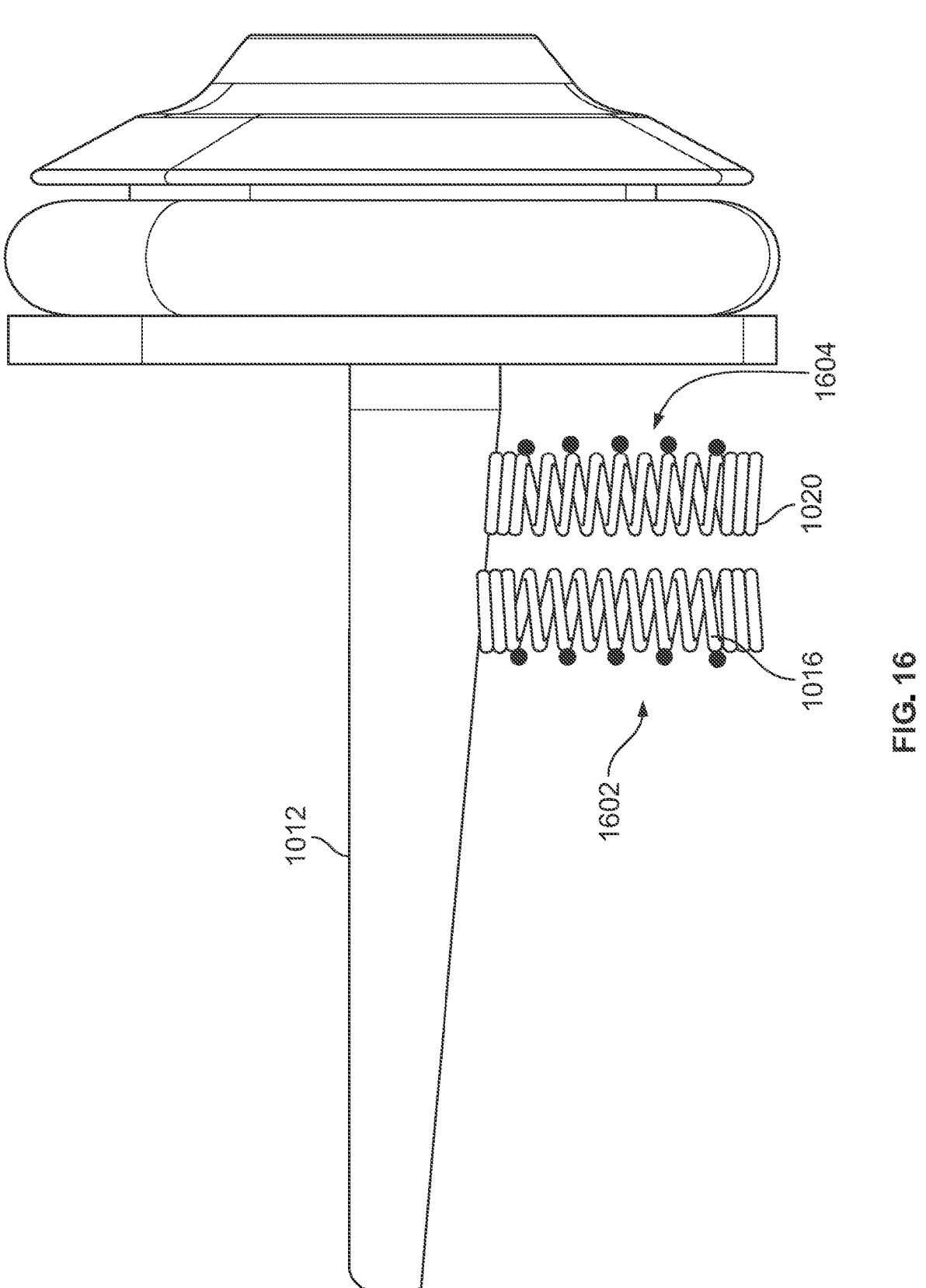
FIG. 16 illustrates another embodiment of a side view of a system for a fluid gauge of a wearable medical device.

FIG. 16 shows another exemplary embodiment of a fluid gauge system for a wearable medical device. In some embodiments, the first spring 1016 and/or the second spring 1020 may have first electrical contacts 1602 and/or second electric contacts 1604. The first electric contacts 1602 and/or second electric contacts 1604 may include a circular, rectangular, or other shaped material. The first electric contacts 1602 and/or the second electric contacts 1604 may be made of a conductive material such as, but not limited to, copper, aluminum, iron, and the like. In some embodiments the first spring 1016 may include the first electric contacts 1602 aligned on a left, right, or other side of coil of the first spring 1016. In some embodiments, the first electric contacts 1602 may be aligned on both a left and right side of the first spring 1016. The second spring 1020 may include the second electric contacts 1604. The second electric contacts 1604 may be the same as that of the first electric contacts 1602. The second spring 1020 may have the second electric contacts 1604 on a left, right, or other side of the second spring 1020. In some embodiments, the second spring 1020 may have the electric contacts 1604 on both sides of the second spring 1020. The first electric contacts 1602 and/or the second electric contacts 1604 may be placed on every other turn of coil of the first spring 1016 and/or the second spring 1020, respectively. In other embodiments, the first electric contacts 1602 and/or the second electric contacts 1604 may be placed apart by two or more coils of spring of the first spring 1016 and/or the second spring 1020. The electric contacts 1602 and/or 1604 may be placed on very coil of spring of the first spring 1016 and/or the second spring 1020. In some embodiments, the electric contacts 1602 and/or 1604 may have two or more contacts. In other embodiments, the electric contacts 1602 and/1604 may include a single contact. The electric contacts 1602 and/or 1604 along one or more sides of the first spring 1016 and/or the second spring 1020 may touch one another as the first spring 1016 and/or the second spring 1020 is compressed from the rod 1012. One or more electrical contacts of the electric contacts 1602 and/or 1604 may act as a short connection for the first spring 1016 and/or the second spring 1020. For instance, the second spring 1020 may be compressed, which may cause two or more of the second electric contacts 1604 to touch, causing a short connection. A processor in communication with a sensing element may determine an amount of liquid drug dispensed based on a change in voltage and/or current of the first spring 1016 and/or the second spring 1020.

Figure 17:
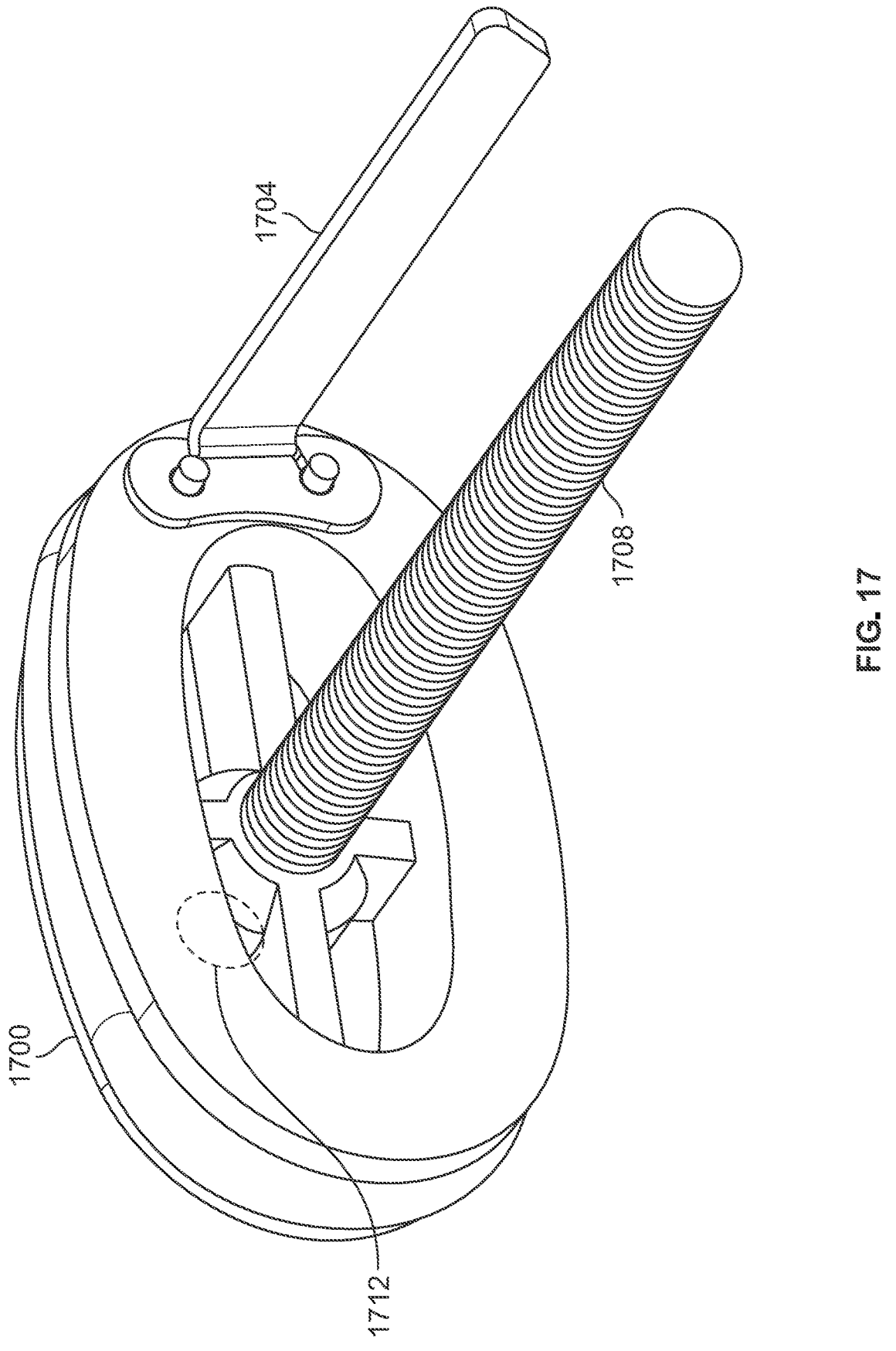
FIG. 17 illustrates an embodiment of a plunger end with a flange.

Referring now to FIG. 17, an embodiment of a plunger end with a flange is illustrated. The plunger end 1700 may include rod 1704, which may be the same as the rod 1012 described above with reference to FIG. 10. In some embodiments, the plunger end 1700 may include flange 1708. The flange 1708 may include a pipe or other structure. In some embodiments, the flange 1708 may be a circular shaped rod. The flange 1708 may be threaded. In some embodiments, the flange 1708 may have one or more holes 1712 at a base of the flange 1708. The hole 1712 of the flange 1708 may be configured to act as a heat stake for one or more posts on a back of a plunger. The rod 1012 may include one or more springs, such as the first spring 1016 and/or the second spring 1020 as described above with reference to FIG. 10. In some embodiments, a nut, such as a rotating nut, may be threaded onto the flange 1708. A nut may advance a position of a plunger in a reservoir which may cause an expulsion of one or more fluids. A screw may be insert-molded with a plunger which may allow for a rigid connection to couple a motion of the plunger with a leadscrew.

Figure 18B:
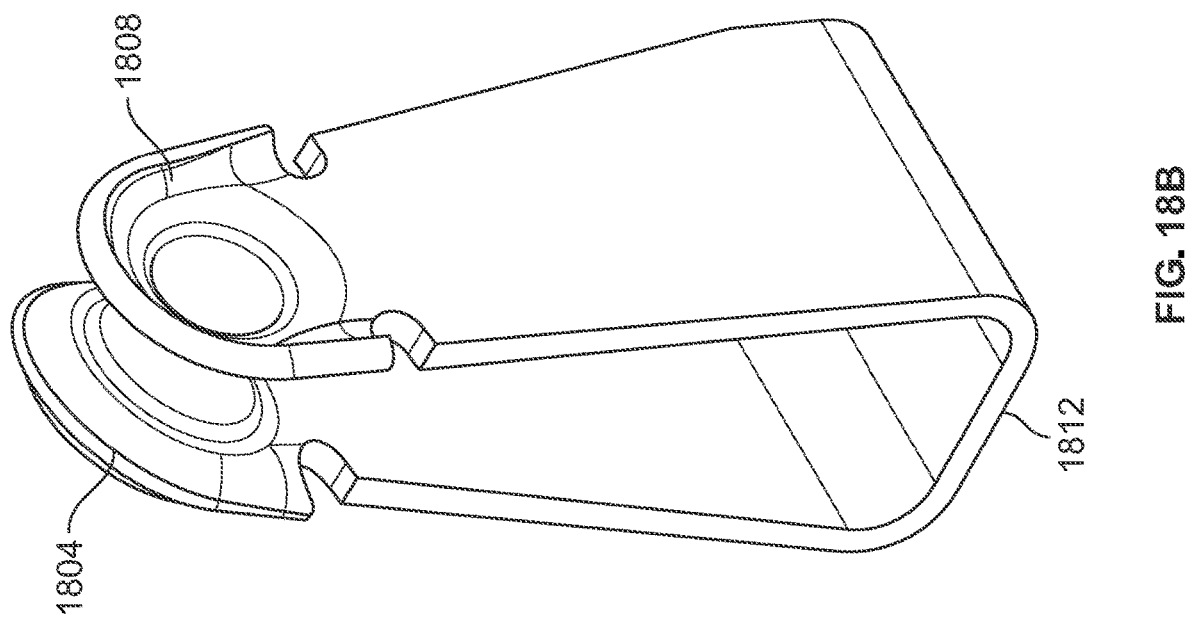
FIGS. 18A-B illustrate an embodiment of springs for a fluid gauge system.
Figure 18A:
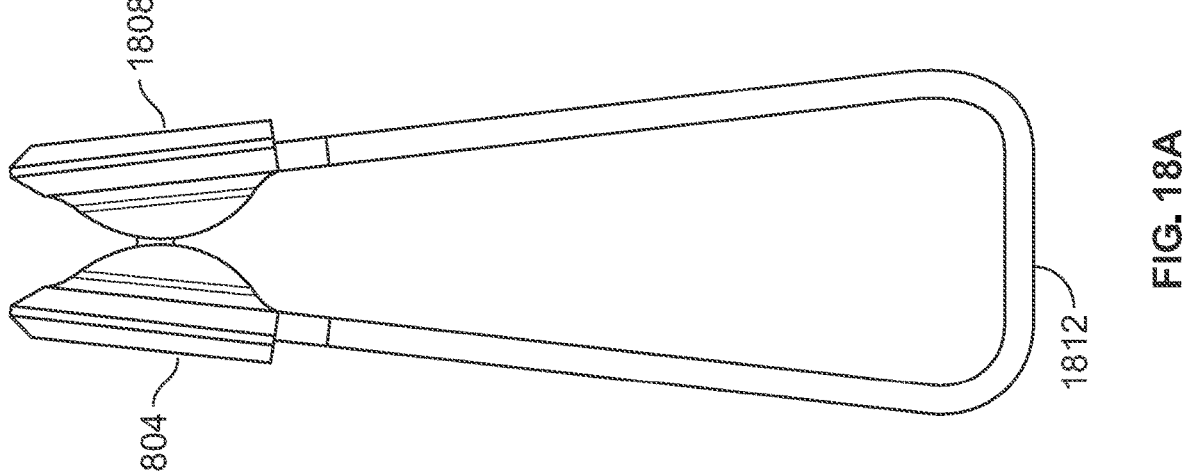

Referring now to FIG. 18, an embodiment of springs for a fluid gauge system of a wearable medical device is presented. The springs may include first contact 1804, second contact 1808, and/or connecting portion 1812. The connecting portion 1812 may form a "U" like or other shape. In some embodiments, the connecting portion 1812 may connected the first contact 1804 with the second contact 1808. The first contact 1804 and/or the second contact 1808 may be shape as, but no limited to, circles, ovals, squares, rectangles, and the like. In some embodiments, the first contact 1804 and/or the second contact 1808 may extend outward from a portion of the connecting portion 1812. For instance, the first contact 1804 and/or the second contact 1808 may include convex circular structures that may form a dome-like or other surface, without limitation. The first contact 1804 may have a diameter of about 1 mm. In other embodiments, the first contact 1804 may have a diameter greater than or less than about 1 mm. The first contact 1804 may extend from the connecting portion 812 by about 0.5 mm. In other embodiments, the first contact 1804 may extend from the connecting portion 812 by more than or less than about 0.5 mm. The second contact 1808 may be the same as the first contact 1804. In other embodiments, the second contact 1808 may have differing dimensions such as, but not limited to, diameters, circumferences, heights, and the like.

The first contact 1804 and/or the second contact 1808 may be touching in an initial stage, such as before a dispensing of a liquid drug by a plunger of a wearable medical device. The connecting portion 1812 may be bent at one or more ends by about, but not limited to, 95, 100, 115, and/or other degrees. One or more bends in the connecting portion 1812 may cause the first contact 1804 and/or the second contact 1808 to press against each other. For instance, the first contact 1804 and/or the second contact 1808 may be pressed against one another in an initial stage. In some embodiments, the first contact 1804 and/or the second contact 1808 may be conductive. For instance, the first contact 1804 and/or the second contact 1808 may be made of, but not limited to, copper, iron, aluminum, and the like. The connecting portion 812 may be flexible, allowing the first contact 1804 and/or the second contact 1808 to be pulled and/or pushed apart. In some embodiments, the metal beam spring 1800 may be positioned in place of the first spring 1016 and/or the second spring 1020 with reference to FIG. 10 above, without limitation. A rod, such as rod 1012 described above with reference to FIG. 10, may push between the first contact 1804 and/or the second contact 1808. A rod, such as rod 1012, may form an electric connection between the first contact 1804, the second contact 1808, and/or the connecting portion 1812. A sensing element may be connected to a rod and/or the metal beam springs 1800. A sensing element may be configured to detect differences in voltage/current of the first contact 1804 and/or the second contact 1808 and my correlate changes to an amount of liquid drug dispensed by a plunger. For instance, a rod may be tapered, such as rod 1012 described above with reference to FIG. 10, and may increase resistance as a smaller end of the rod moves between the first contact 1804 and the second contact 1808 towards the wider end of the rod.

In some embodiments, the first contact 1804 and/or the second contact 1808 may initially be separated and may form an electric connection with one another through a rod sliding through the first contact 1804 and the second contact 1808. The first contact 1804 and the second contact 1808 may be separate tabs, in an embodiment, without the connecting portion 1812. For instance, and without limitation, the first contact 1804 and the second contact 1808 may be separately soldered to a circuit board of a wearable medical device. In some embodiments, the metal beam springs 1800 may provide for a more secure grasp of one or more automated manufacturing tools, such as robotic arms or other grasping devices.

Figure 19:
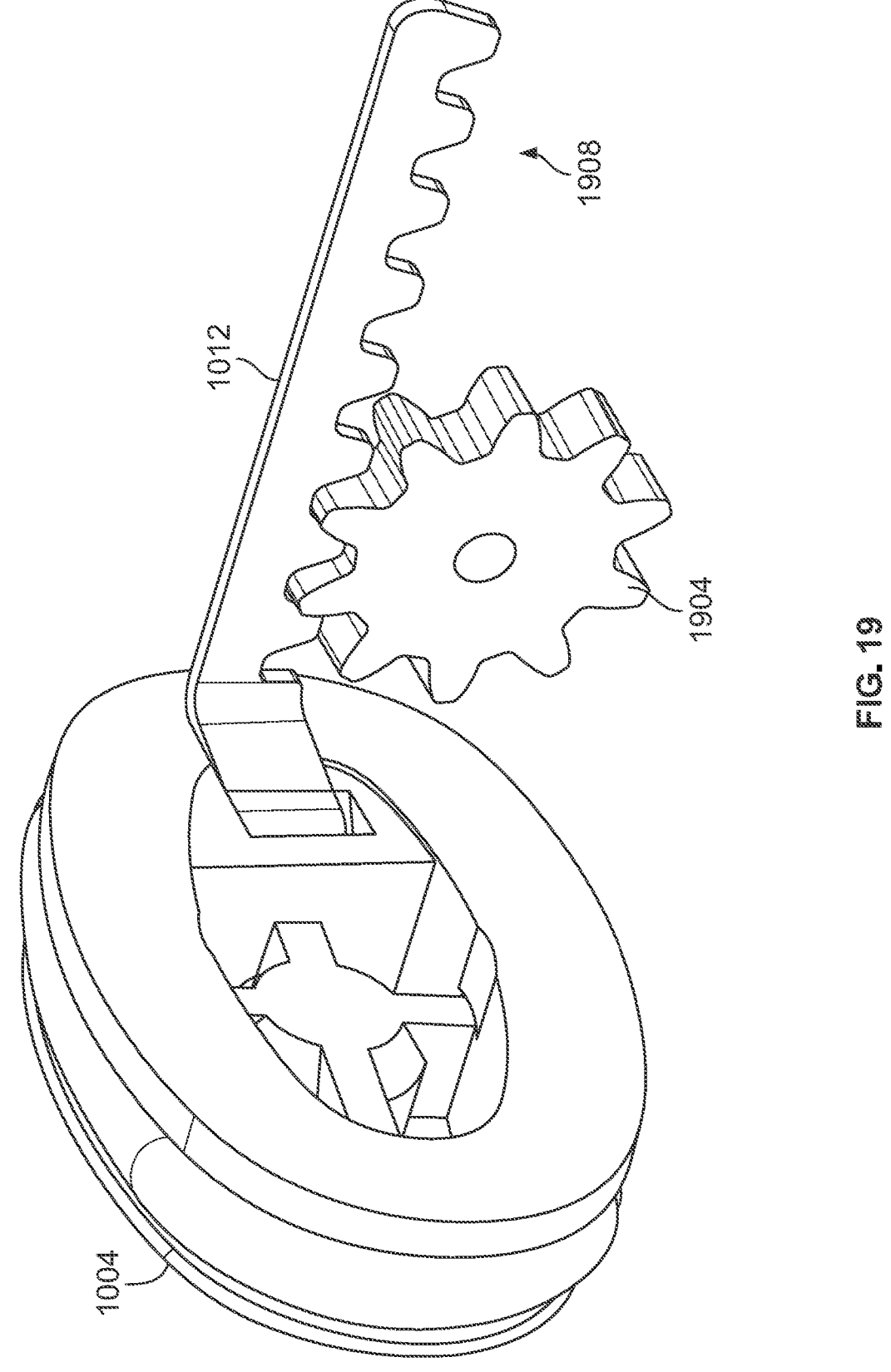
FIG. 19 illustrates a gear system for a fluid gauge for a wearable medical device.

Referring now to FIG. 19, an embodiment of a gear system for a fluid gauge for a wearable medical device is shown. The gear system 1900 may include rod 1012 and/or plunger end 1004 as described above with reference to FIG. 10. In some embodiments, the rod 1012 may have teeth 1908. The teeth 1908 may run along a bottom side of the rod 1012, without limitation. In some embodiments, the teeth 1908 may include 7 teeth, less than 7 teeth, or more than 7 teeth. Each tooth of the teeth 1908 may be configured to interface with one or more protrusions of gear 1904. The gear 1904 may include a spur, helical, skew, and/or other gear. In some embodiments, the gear 1904 may be configured to rotate in a direction, such as clockwise, counterclockwise, and the like. The gear 1904 may rotate due to a torque applied by one or more teeth of the teeth 1908. In some embodiments, the gear 1904 and the teeth 1908 may have a plurality of teeth and teeth cutouts, which may allow for precise movements of the rod 1012. As a non-limiting example, the gear 1904 and the teeth 1908 may include 50 or more teeth-hole pairings. In some embodiments, a plurality of gears, such as two or more gears, may be implemented. For instance, a second smaller gear may be connected to the gear 1904. A smaller gear connected to the gear 1904 may allow for more rotation, which may provide for increased rotational data generation through a sensing element.

A sensing element may be configured to detect a rotation of the gear 1904. For instance, an encoder may be used within system 1900. An encoder may include, without limitation, a rotary, linear, position, and/or optical encoders. In some embodiments, a rotary potentiometer may be used. A sensing element of system 1900 may be configured to determine a quantity of degrees rotated of the gear 1904, a difference between a current position of the gear 1904 and a previous position of the gear 1904, and/or other rotational data. For instance, and without limitation, a rotary encoder may be configured to detect every 15 degrees of rotation. A sensing element and/or processor may be connected to an encoder and may correlate a degree of rotation to an amount of liquid drug dispensed. For instance, and without limitation, every 10 degrees of rotation may correspond to an amount of liquid drug dispensed of about 0.1 ml. In some embodiments, a sensing element and/or processor may be configured to wake up or otherwise initialize a wearable medical device based on received rotational data generated by the gear 1904.

Figure 20:
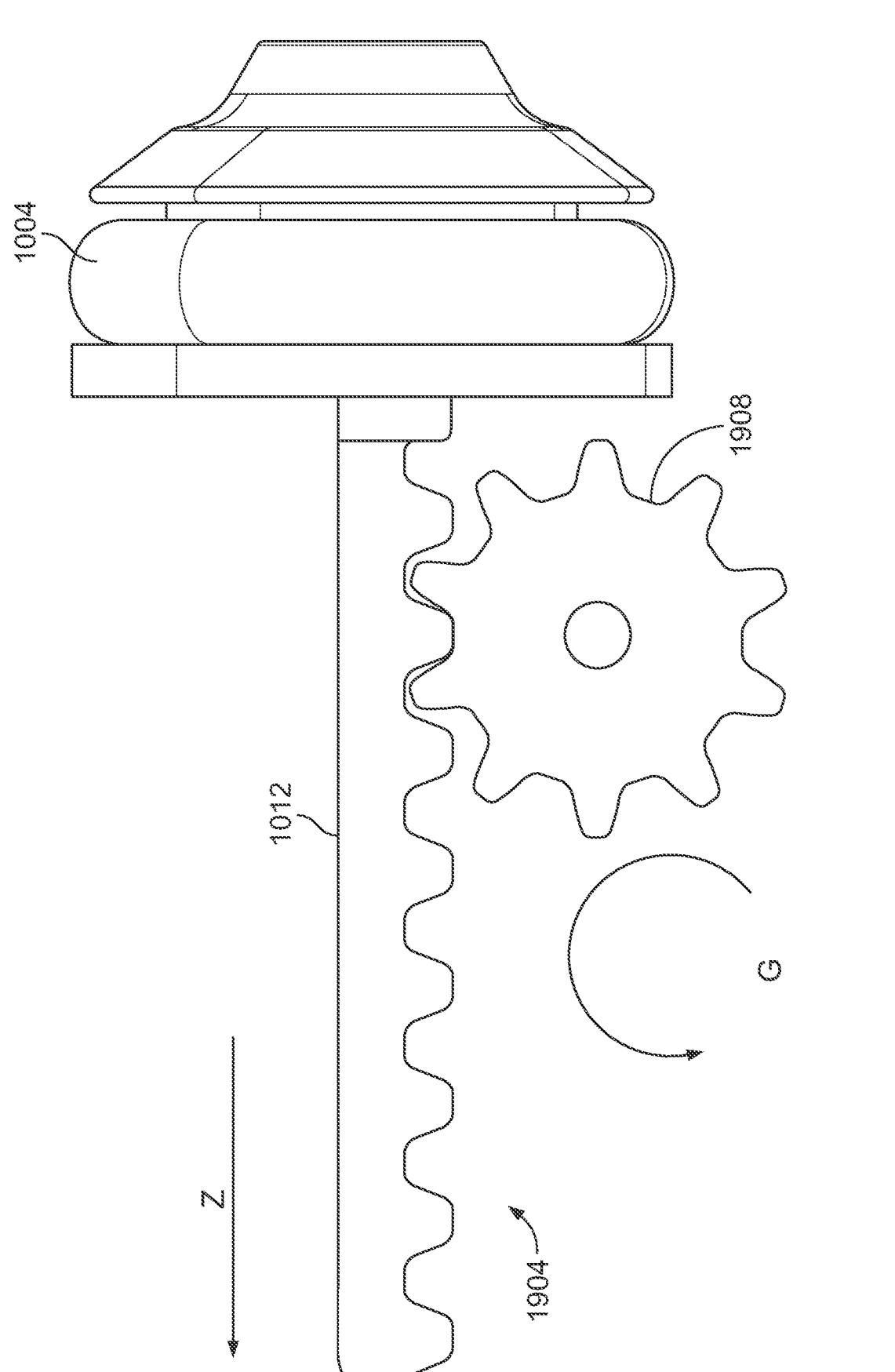
FIG. 20 illustrates a side view of the gear system of FIG. 19.

Referring now to FIG. 20, a side view of the gear system of FIG. 19 is presented. The gear system 2000 may include plunger end 1004, rod 1012, teeth 1908, and/or gear 1904, as described above with reference to FIG. 19, without limitation. The rod 1012 may be configured to move in direction Z. One or more teeth of the teeth 1908 may move in direction Z and may interface with gear 1904, which may cause gear 1904 to rotate in direction G. As the gear 1904 rotates in direction G, an encoder may be configured to detect one or more degrees of rotation of the gear 1904. A sensing element and/or processor may be configured to receive data from an encoder and correlate a degree of rotation to an amount of liquid drug dispensed. For instance, a and/or processor may determine that every 15 degrees of rotation corresponds to about 2 ml of liquid drug dispensed.

In at least one embodiment, a drive mechanism is provided that may include a pair of co-axial ratchet wheels (i.e., first and second ratchet wheels) that are driven by a first driving arm and a second driving arm. In some examples, a sensor contact arrangement coupled to the first and second ratchet wheels allows the drive mechanism to be responsive to the travel of the respective ratchet arms in various implementations and configurations. In this context, a co-axial arrangement refers to an arrangement where the first and second rachet wheels rotate around the same axis or a common axis.

Some examples of the disclosed device may be implemented, for example, using a storage medium, a computer-readable medium, or an article of manufacture which may store an instruction or a set of instructions that, if executed by a machine (i.e., processor or microcontroller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A system for determining a position of a plunger in a drug delivery device comprising a drive mechanism configured to allow the plunger to move in a first direction while a liquid drug is being inserted into a reservoir and drive the plunger in a second direction to deliver the liquid drug to a patient, the system comprising:

sensor circuitry;

a first electrical contact;

a second electrical contact, wherein the first electrical contact and the second electrical contact are coupled to the sensor circuitry; and a conductive element in electrical communication with the first electrical contact and the second electrical contact;

wherein the sensor circuitry is in electrical communication with the first electrical contact and the second electrical contact and is operable to:

receive a voltage or current value for at least one of the first electrical contact or the second electrical contact, the voltage or current value indicative of an electrical resistance between the first electrical contact and the second electrical contact;

determine a position of the plunger in the drug delivery device based on a mapping of the voltage, current value, or electrical resistance between the first electrical contact and the second electrical contact to a state or position of the plunger;

compare the position of the plunger to a predetermined threshold value indicating that the reservoir has reached at least a partially-filled state; and when the position of the plunger passes the predetermined threshold value, set the drug delivery device into a wakeup mode via the first electrical contact and the second electrical contact, wherein the wakeup mode initializes or starts up the drug delivery device.

2. The system of claim 1, wherein the conductive element is a rod.

3. The system of claim 2, wherein the conductive element is operable to move with the plunger in the drug delivery device.

4. The system of claim 1, wherein the conductive element is configured to slide past both the first electrical contact and the second electrical contact, increasing or decreasing the electrical resistance between the first electrical contact and the second electrical contact depending on the direction of movement of the conductive element.

5. The system of claim 1, wherein the sensor circuitry is operable to determine a decreased amount of a level of a liquid drug based on a decrease in the electrical resistance between the first electrical contact and the second electrical contact.

6. The system of claim 1, wherein the sensor circuitry is operable to determine an increased amount of a level of a liquid drug based on an increase in the electrical resistance between the first electrical contact and the second electrical contact.

7. The system of claim 1, wherein the sensor circuitry is operable to determine a level of a liquid drug in a reservoir of the drug delivery device based on the position of the plunger.

8. The system of claim 1, wherein the conductive element is electrically charged prior to it contacting the first and/or second electrical contacts.

9. The system of claim 1, wherein the sensor circuitry is further operable to wake up the drug delivery device based on the electrical resistance between the first electrical contact and the second electrical contact.

10. The system of claim 1, wherein the sensor circuitry is further operable to wake up the drug delivery device based on the electrical resistance between the first electrical contact and the second electrical contact exceeding a threshold value.

11. A method of determining a position of a plunger in a drug delivery device, comprising a drive mechanism configured to allow the plunger to move in a first direction while a liquid drug is being inserted into a reservoir and drive the plunger in a second direction to deliver the liquid drug to a patient, the method comprising:

contacting, by a conductive element, a first electrical contact and a second electrical contact;

receiving, by sensor circuitry in communication with the first electrical contact and the second electrical contact, a voltage or current value for at least one of the first electrical contact or the second electrical contact, the voltage or current value indicative of an electrical resistance between the first electrical contact and the second electrical contact;

determining, by the sensor circuitry, the position of the plunger in the drug delivery device based on a mapping of the voltage, current value, or electrical resistance between the first electrical contact and the second electrical contact to a state or position of the plunger;

comparing the position of the plunger to a predetermined threshold value indicating that the reservoir has reached at least a partially-filled state; and when the position of the plunger passes the predetermined threshold value, setting the drug delivery device into a wakeup mode via the first electrical contact and the second electrical contact, wherein the wakeup mode initializes or starts up the drug delivery device.

12. The method of claim 11, further comprising determining, by the sensor circuitry, a level of a liquid drug in the drug delivery device based on the position of the plunger in the drug delivery device.

13. The method of claim 12, wherein the conductive element is operable to move with the plunger in the drug delivery device.

14. The method of claim 11, further comprising moving the conductive element past both the first electrical contact and the second electrical contact, thereby increasing or decreasing the electrical resistance between the first electrical contact and the second electrical contact depending on the direction of movement of the conductive element.

15. The method of claim 11, further comprising determining, by the sensor circuitry, a decreased amount of a level of a liquid drug based on a decrease in the electrical resistance between the first electrical contact and the second electrical contact.

16. The method of claim 11, further comprising determining, by the sensor circuitry, an increased amount of a level of a liquid drug based on an increase in the electrical resistance between the first electrical contact and the second electrical contact.

17. The method of claim 11, further comprising determining, by the sensor circuitry, an amount of a liquid drug in a reservoir of the drug delivery device and outputting data indicative of the amount of the liquid drug to a user of the drug delivery device.

18. The method of claim 11, further comprising electrically charging the conductive element prior to the contacting the first and/or second electrical contacts.

19. The method of claim 11, further comprising waking up, by the sensor circuitry, the drug delivery device based on the electrical resistance between the first electrical contact and the second electrical contact.

20. The method of claim 19, further comprising comparing, by the sensor circuitry, the electrical resistance to a threshold value; and waking up the drug delivery device if the electrical resistance surpasses the threshold.

* * * * *